United States Patent
Townsend et al.

(10) Patent No.: US 6,582,965 B1
(45) Date of Patent: *Jun. 24, 2003

(54) **METHOD FOR *DE NOVO* PEPTIDE SEQUENCE DETERMINATION**

(75) Inventors: Robert Reid Townsend, Oxford (GB); Raj Bhikhu Parekh, Oxon (GB); Sally Barbara Prime, Oxford (GB); Nick Sinclair Wedd, Oxford (GB)

(73) Assignee: Oxford GlycoSciences (UK) Ltd, Abingdon (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/877,605

(22) Filed: Jun. 18, 1997

(30) Foreign Application Priority Data

May 22, 1997 (GB) .............................................. 9710582

(51) Int. Cl.⁷ ........................ G01N 33/00; B01D 59/44; H01J 49/00
(52) U.S. Cl. .......................... 436/89; 436/90; 250/282; 435/DIG. 20
(58) Field of Search ....................... 436/89, 96; 703/11, 703/12; 250/282; 435/DIG. 20

(56) References Cited

U.S. PATENT DOCUMENTS

| | | | |
|---|---|---|---|
| 4,224,031 A | 9/1980 | Mee et al. ..................... 23/230 |
| 4,701,419 A | 10/1987 | Morris ......................... 436/89 |
| 4,820,648 A | 4/1989 | Caprioli et al. ................ 436/89 |
| 5,003,059 A | 3/1991 | Brennan ....................... 536/27 |
| 5,010,175 A | * 4/1991 | Rutter et al. ................. 530/334 |
| 5,045,694 A | 9/1991 | Beavis et al. ................. 250/287 |
| 5,103,093 A | 4/1992 | Sakairi et al. ................ 250/288 |
| 5,135,870 A | 8/1992 | Williams et al. ............. 436/173 |
| 5,221,518 A | 6/1993 | Mills .......................... 422/62 |
| 5,240,859 A | 8/1993 | Aebersold ..................... 436/89 |
| 5,246,865 A | 9/1993 | Stolowitz ..................... 436/89 |
| 5,288,644 A | 2/1994 | Beavis et al. ................. 436/94 |
| 5,427,744 A | 6/1995 | Parekh et al. ................ 422/116 |
| 5,432,093 A | 7/1995 | Bailey et al. ................. 436/89 |
| 5,453,247 A | 9/1995 | Beavis et al. ............. 422/68.1 |
| 5,470,753 A | 11/1995 | Sepetov et al. ............... 436/89 |
| 5,510,240 A | 4/1996 | Lam et al. ................... 435/7.1 |
| 5,521,097 A | 5/1996 | Uchida et al. ................ 436/86 |
| 5,527,675 A | 6/1996 | Coull et al. ..................... 435/6 |
| 5,534,440 A | 7/1996 | Aebersold .................... 436/89 |
| 5,538,897 A | 7/1996 | Yates, III et al. ............. 436/89 |
| 5,547,835 A | 8/1996 | Käster ........................... 435/6 |
| 5,565,171 A | 10/1996 | Dovichi et al. ............. 422/68.1 |
| 5,580,733 A | 12/1996 | Levis et al. ..................... 435/6 |
| 5,668,373 A | * 9/1997 | Robbat, Jr. et al. ..... 250/339.12 |
| 5,672,869 A | * 9/1997 | Windig et al. .............. 250/282 |

FOREIGN PATENT DOCUMENTS

WO     WO 98/52129     11/1998

OTHER PUBLICATIONS

US 5,382,513, 1/1995, Lam et al. (withdrawn)
Karl Klauser, Description, Instructions, and Tips for MS–Tag, http:\\rafael.ucsf.edu/instruct/tagman.html, revised Mar. 13, 1997, date of origin unknown.
Hamm et al., Peptide Sequencing Program, CABIOS 2 1985, pp. 115–118.
Sakurai et al., PAAS 3: A Computer Program to Determine Probable Sequence of Peptides from Mass Spectrometric Data, Biomed. Mass Spectrom 11 1984, pp. 396–399.
Fernandez–de–Cossio et al., 1998, "Automated Interpretation of High energy collision induced dissociation spectra of singly protonated peptides by 'seqMS', a software aid for De Novo sequencing by tandem mass spectrometry", Rapid. Commun. Mass. Spectrom. 12:1867–1878.
Hamm et al., 1986, "Peptide sequencing program", Comput Appl Biosci. 2(2):115–8.
Hunt et al., 1986, "Protein Sequencing by tandem mass spectrometry", Proc. Natl. Acad. Sci USA 83:6233–6237.
James et al., 1993, "Protein identification by mass profile fingerprinting", Biochem Biophys Res Commun. 195(1):58–64.
Jensen et al., 1997, "Identification of the components of simple protein mixtures by high accuracy peptide mass mapping and database searching", Anal. Chem. 69:4741–4750.

(List continued on next page.)

*Primary Examiner*—Andrew Wang
*Assistant Examiner*—Tomas H F Friend
(74) *Attorney, Agent, or Firm*—Pennie & Edmonds LLP

(57) ABSTRACT

The present invention relates to a method for generating a library of peptides based on a peptide of a predetermined molecular mass and to a method of determining the amino acid sequence of the peptide from the library. A set of amino acids that can be present in the peptide are defined, and an allowed library of all possible sequences of the amino acids in the set having a total mass equal to the predetermined molecular mass, allowing for water lost in forming peptide bonds and for protonation, is generated. The allowed library may be generated by first generating a set of all combinations of amino acids having a total mass equal to the predetermined molecular mass of the peptide and then calculating all linear permutations of all amino acids in each such combination. Generally, the molecular mass is determined using a mass spectrometer. A theoretical fragmentation spectrum for every amino acid sequence in the allowed set may also be calculated for use in determining the amino acid sequence of the peptide. The fragmentation spectra may be of any type known in the art, such as a mass spectrum or a protease or chemical fragmentation spectrum. The theoretical fragmentation spectra calculated for each member of the allowed peptide library may be compared to an experimental fragmentation spectrum for the unknown peptide to determine the amino acid sequence of the unknown peptide.

17 Claims, 11 Drawing Sheets

OTHER PUBLICATIONS

Pappin et al., 1993, "Rapid identification of proteins by peptide–mass fingerprinting", Current Biology 3:327–332.

Sepetov et al., 1993, "The use of hydrogen deuterium exchange to facilitate peptide sequencing by electrospray tandem mass spectrometry", Rapid Commun. Mass Spectrom. 7:58–62.

Shevchenko et al., 1991, "Rapid 'de novo' peptide sequencing by a combination of nanoelectrospray, isotopic labeling and a quadrople/time of flight mass spectrometer", Rapid. Commun. Mass Spectrom. 11:1015–1024.

Wilm et al., "Simplified "de novo" sequencing with quadrupole or quadrupole TOF instruments for finding homologous proteins or for cloning".

Yates et al., 1997, "Protein Sequencing by Tandem Mass Spectrometry", UMI Dissertation Services.

Shevchenko et al., "Rapid 'de Novo' Peptide Sequencing by a Combination of Nanoelectrospray, Isotopic Labeling and a Quadrupole/Time–of–flight Mass Spectometry," Rapid Communications in Mass Spectrometry, vol. 11, 1015–1024 (1997).

Tayloret al., "Sequence Database Searches via de Novo Peptide Sequencing by Tandem Mass Spectrometry," Rapid Communications in Mass Spectrometry, vol. 11, 1067–1075 (1997).

Scarberry et al., "Peptide Sequence Determination from High–Energy Collision–Induced Dissociation Spectra Using Articifical Neural Networks," J Am Soc Mass Spectrom 1995, 6, 947–961.

Sakurai et al., 1984, A Computer Program to Determine Probable Sequence of Peptides from Mass Spectrometric Data, *Biomed Mass Spec. 11*:396.

Ward et al., "Proteins and Peptides, Isolation for Sequence Analysis of", Mol. Biol. Biotech., 767–771, ed. Meyers.

Keen et al., "Protein Sequenceing Techniques", Mol. Biol. Biotech., 771–773, ed. Meyers.

Williams et al., "Protein Analysis by Integrated Sample Preparation, Chemistry, and Mass Slpectrometry", Mol. Biol. Biotech., 731–737, ed. Meyers.

Jonscher et al., "Matrix–assisted Laser Desorption Ionization/Quadrupole Ion Trap Mass Spectrometry of Peptides", 1997, J. Biol. Chem. 272:3/1735–1741.

Jonscher et al., "The Quadrupole Ion Trap Mass Spectrometer—A Small Solution to a Big Challenger", 1997, Anal. Biochem. 244:1–15.

McCormack et al., "Direct Analysis and Identification of Proteins in Mixtures by LC/MS/MS and Database Searching at the Low–Femtomole Level", 1997 Anal. Chem. 69:767–776.

Yates et al., "Search of Sequence Database with Uninterpreted High–Energy Collision–Induced Dissociation Spectra of Peptides", 1996, J Am Soc Mass Spectrom, 1996, 7:1089–1098.

Jonscher et al., "Mixture Analysis Using a Quadrupole Mass Filter/Quadrupole Ion Trap Mass Spectrometer", 1996, Anal. Chem. 68:659–667.

Hayden et al., "Analysis of Naturally Processed Peptides Eluted From HLA DRB1*0402 and *0404", 1996, J. Neurosci. Res. 45:795–802.

Figeys et al. "Protein identification by solid phase microextraction–capillary zone electrophoresis–microelectrospray–tandem mass spectrometry", 1996, Nature Biotech. 14: 1579–1583.

Yates et al., "Mining Genomes with MS", 1996, Anal. Chem. News & Features 534A–540A.

Link et al., "Analyzing complex biological systems using micro–LC–ESI–MS–MS", 1996, American Laboratory 27–30.

Yates et al., "Future Prospects for the Analysis of Complex Biological Systems Using Micro–column Liquid Chromatography–Electrospray Tandem Mass Spectrometry", 1996, Analyst 121:65R–76R.

Griffin et al., "Direct Database Searching with MALDI–PSD Spectra of Peptides", 1995, Rapid Comm. in Mass Spectrom. 9:1546–1551.

Yates et al., "Method to Correlate Tandem Mass Spectra of Modified Peptides to Amino Acid Sequences in the Protein Database", 1995, Anal. Chem. 67:1426–1436.

Yates, et al., "Mining Genomes: Correlating Tandem Mass Spectra of Modified and Unmodified Peptides to Sequences in Nucleotide Databases", 1995, Anal. Chem. 67:3202–3210.

McCormack et al., "Localization of the Disulfide Bond Involved in Post–translational Processing of Glycosylasparaginase and Disrupted by a Mutation in the Finnish–type Aspartylglycosaminuria", 1995, J. Biol. Chem. 270:7/3212–3215.

McCormack et al., "Peptide Sequence Analysis of Quadrupole Mass Spectrometers", 1994, Methods 6:274–283.

Eng et al., "An Approach to Correlate Tandem Mass Spectral Data of Peptides with Amino Acid Sequences in a Protein Database", 1994, J Am Soc Mass Spectrom 5:976–989.

Yates et al., "Peptide Mass Maps: A Highly Informative Approach to Protein Identification", 1993, Anal. Biochem. 214:397–408.

Currie et al., "Analysis of Oligodeoxynucleotides by Negative–Ion Matrix–Assisted Laser Desorption Mass Spectrometry", 1993, J Am Soc Mass Spectrom 4:955–963.

Jonscher et al., "Matrix–assisted Laser Desorption of Peptides and Proteins on a Quadrupole Ion Trap Mass Spectrometer", 1993, Rapid Comm. Mass Spectrom. 7:20–26.

Griffin et al., "Structural analysis of proteins by capillary HPLC electrospray tandem mass spectrometry", 1991, Intl. J Mass Spectrom & Ion Proc 111:131–149.

Yates et al., "Proteolytic Fragments of the Nicotinic Acetylcholine Receptor Identified by Mass Spectrometry: Implications for Receptor Topography", 1989, Biochemistry 28:9184–9191.

Hunt et al., "Amino Acid Sequence Analysis of Two Mouse Calbindin–$D_{9k}$ Isoforms by Tandem Mass Spectrometry", J. Biol. Chem. 264:11/6580–6586.

Krishnamurthy et al., "Structural characterization of toxic cyclic peptides from blue–green algae by tandem mass spectrometry", 1989, Proc. Natl. Acad. Sci. USA 86:770–774.

Hunt et al., "Peptide Sequence Analysis by Laser Photodissociation Fourier Transform Mass Spectrometry", 1987, J. Chem. Soc., Commun. 548–550.

Hunt et al., "Tandem quadrupole Fourier–transform mass spectrometry of oligopeptides and small proteins", 1987, Proc. Natl. Acad. Sci. USA 84:620–623.

Hunt et al., "Tandem Quadrupole–Fourier Transform Mass Spectrometry of Oligopeptides", 1985, Anal. Chem. 57:2728–2733.

Yates et al., "Mixed Gas Chemical Ionization Mass Spectrometry of Peptide Derivatives", Biomed. Mass Spectrom. 10:10/567–571.

\* cited by examiner

SEQUENCE LISTING

```
<160> NUMBER OF SEQ ID NOS:  353

<210> SEQ ID NO 1
<211> LENGTH: 5
<212> TYPE: PRT
<213> ORGANISM: Artificial Sequence
<220> FEATURE:
<223> OTHER INFORMATION: Peptide X Library

<400> SEQUENCE: 1

Tyr Ile His Trp Arg
1               5

<210> SEQ ID NO 2
<211> LENGTH: 5
<212> TYPE: PRT
<213> ORGANISM: Artificial Sequence
<220> FEATURE:
<223> OTHER INFORMATION: Peptide X Library

<400> SEQUENCE: 2

Ile Tyr His Trp Arg
1               5

<210> SEQ ID NO 3
<211> LENGTH: 5
<212> TYPE: PRT
<213> ORGANISM: Artificial Sequence
<220> FEATURE:
<223> OTHER INFORMATION: Peptide X Library

<400> SEQUENCE: 3

Tyr His Ile Trp Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Peptide X Library

<400> SEQUENCE: 4

His Tyr Ile Trp Arg
1               5

<210> SEQ ID NO 5
<211> LENGTH: 5
```

```
<212> TYPE: PRT
<213> ORGANISM: Artificial Sequence
<220> FEATURE:
<223> OTHER INFORMATION: Peptide X Library

<400> SEQUENCE: 5

Ile His Tyr Trp Arg
 1               5

<210> SEQ ID NO 6
<211> LENGTH: 5
<212> TYPE: PRT
<213> ORGANISM: Artificial Sequence
<220> FEATURE:
<223> OTHER INFORMATION: Peptide X Library

<400> SEQUENCE: 6

His Ile Tyr Trp Arg
 1               5

<210> SEQ ID NO 7
<211> LENGTH: 5
<212> TYPE: PRT
<213> ORGANISM: Artificial Sequence
<220> FEATURE:
<223> OTHER INFORMATION: Peptide X Library

<400> SEQUENCE: 7

Tyr Ile Trp His Arg
 1               5

<210> SEQ ID NO 8
<211> LENGTH: 5
<212> TYPE: PRT
<213> ORGANISM: Artificial Sequence
<220> FEATURE:
<223> OTHER INFORMATION: Peptide X Library

<400> SEQUENCE: 8

Ile Tyr Trp His Arg
 1               5

<210> SEQ ID NO 9
<211> LENGTH: 5
<212> TYPE: PRT
<213> ORGANISM: Artificial Sequence
<220> FEATURE:
<223> OTHER INFORMATION: Peptide X Library

<400> SEQUENCE: 9

Tyr Trp Ile His Arg
 1               5

<210> SEQ ID NO 10
<211> LENGTH: 5
<212> TYPE: PRT
<213> ORGANISM: Artificial Sequence
<220> FEATURE:
<223> OTHER INFORMATION: Peptide X Library

<400> SEQUENCE: 10

Trp Tyr Ile His Arg
 1               5

<210> SEQ ID NO 11
<211> LENGTH: 5
<212> TYPE: PRT
```

```
<213> ORGANISM: Artificial Sequence
<220> FEATURE:
<223> OTHER INFORMATION: Peptide X Library

<400> SEQUENCE: 11

Ile Trp Tyr His Arg
 1               5

<210> SEQ ID NO 12
<211> LENGTH: 5
<212> TYPE: PRT
<213> ORGANISM: Artificial Sequence
<220> FEATURE:
<223> OTHER INFORMATION: Peptide X Library

<400> SEQUENCE: 12

Trp Ile Tyr His Arg
 1               5

<210> SEQ ID NO 13
<211> LENGTH: 5
<212> TYPE: PRT
<213> ORGANISM: Artificial Sequence
<220> FEATURE:
<223> OTHER INFORMATION: Peptide X Library

<400> SEQUENCE: 13

Tyr His Trp Ile Arg
 1               5

<210> SEQ ID NO 14
<211> LENGTH: 5
<212> TYPE: PRT
<213> ORGANISM: Artificial Sequence
<220> FEATURE:
<223> OTHER INFORMATION: Peptide X Library

<400> SEQUENCE: 14

His Tyr Trp Ile Arg
 1               5

<210> SEQ ID NO 15
<211> LENGTH: 5
<212> TYPE: PRT
<213> ORGANISM: Artificial Sequence
<220> FEATURE:
<223> OTHER INFORMATION: Peptide X Library

<400> SEQUENCE: 15

Tyr Trp His Ile Arg
 1               5

<210> SEQ ID NO 16
<211> LENGTH: 5
<212> TYPE: PRT
<213> ORGANISM: Artificial Sequence
<220> FEATURE:
<223> OTHER INFORMATION: Peptide X Library

<400> SEQUENCE: 16

Trp Tyr His Ile Arg
 1               5

<210> SEQ ID NO 17
<211> LENGTH: 5
<212> TYPE: PRT
<213> ORGANISM: Artificial Sequence
```

```
<220> FEATURE:
<223> OTHER INFORMATION: Peptide X Library

<400> SEQUENCE: 17

His Trp Tyr Ile Arg
1               5

<210> SEQ ID NO 18
<211> LENGTH: 5
<212> TYPE: PRT
<213> ORGANISM: Artificial Sequence
<220> FEATURE:
<223> OTHER INFORMATION: Peptide X Library

<400> SEQUENCE: 18

Trp His Tyr Ile Arg
1               5

<210> SEQ ID NO 19
<211> LENGTH: 5
<212> TYPE: PRT
<213> ORGANISM: Artificial Sequence
<220> FEATURE:
<223> OTHER INFORMATION: Peptide X Library

<400> SEQUENCE: 19

Ile His Trp Tyr Arg
1               5

<210> SEQ ID NO 20
<211> LENGTH: 5
<212> TYPE: PRT
<213> ORGANISM: Artificial Sequence
<220> FEATURE:
<223> OTHER INFORMATION: Peptide X Library

<400> SEQUENCE: 20

His Ile Trp Tyr Arg
1               5

<210> SEQ ID NO 21
<211> LENGTH: 5
<212> TYPE: PRT
<213> ORGANISM: Artificial Sequence
<220> FEATURE:
<223> OTHER INFORMATION: Peptide X Library

<400> SEQUENCE: 21

Ile Trp His Tyr Arg
1               5

<210> SEQ ID NO 22
<211> LENGTH: 5
<212> TYPE: PRT
<213> ORGANISM: Artificial Sequence
<220> FEATURE:
<223> OTHER INFORMATION: Peptide X Library

<400> SEQUENCE: 22

Trp Ile His Tyr Arg
1               5

<210> SEQ ID NO 23
<211> LENGTH: 5
<212> TYPE: PRT
<213> ORGANISM: Artificial Sequence
<220> FEATURE:
```

```
<223> OTHER INFORMATION: Peptide X Library

<400> SEQUENCE: 23

His Trp Ile Tyr Arg
 1               5

<210> SEQ ID NO 24
<211> LENGTH: 5
<212> TYPE: PRT
<213> ORGANISM: Artificial Sequence
<220> FEATURE:
<223> OTHER INFORMATION: Peptide X Library

<400> SEQUENCE: 24

Trp His Ile Tyr Arg
 1               5

<210> SEQ ID NO 25
<211> LENGTH: 6
<212> TYPE: PRT
<213> ORGANISM: Artificial Sequence
<220> FEATURE:
<223> OTHER INFORMATION: Peptide X Library

<400> SEQUENCE: 25

Tyr Ile His Glu Gly Arg
 1               5

<210> SEQ ID NO 26
<211> LENGTH: 6
<212> TYPE: PRT
<213> ORGANISM: Artificial Sequence
<220> FEATURE:
<223> OTHER INFORMATION: Peptide X Library

<400> SEQUENCE: 26

Ile Tyr His Glu Gly Arg
 1               5

<210> SEQ ID NO 27
<211> LENGTH: 6
<212> TYPE: PRT
<213> ORGANISM: Artificial Sequence
<220> FEATURE:
<223> OTHER INFORMATION: Peptide X Library

<400> SEQUENCE: 27

Tyr His Ile Glu Gly Arg
 1               5

<210> SEQ ID NO 28
<211> LENGTH: 6
<212> TYPE: PRT
<213> ORGANISM: Artificial Sequence
<220> FEATURE:
<223> OTHER INFORMATION: Peptide X Library

<400> SEQUENCE: 28

His Tyr Ile Glu Gly Arg
 1               5

<210> SEQ ID NO 29
<211> LENGTH: 6
<212> TYPE: PRT
<213> ORGANISM: Artificial Sequence
<220> FEATURE:
<223> OTHER INFORMATION: Peptide X Library
```

<400> SEQUENCE: 29

Ile His Tyr Glu Gly Arg
1               5

<210> SEQ ID NO 30
<211> LENGTH: 6
<212> TYPE: PRT
<213> ORGANISM: Artificial Sequence
<220> FEATURE:
<223> OTHER INFORMATION: Peptide X Library

<400> SEQUENCE: 30

His Ile Tyr Glu Gly Arg
1               5

<210> SEQ ID NO 31
<211> LENGTH: 6
<212> TYPE: PRT
<213> ORGANISM: Artificial Sequence
<220> FEATURE:
<223> OTHER INFORMATION: Peptide X Library

<400> SEQUENCE: 31

Tyr Ile Glu His Gly Arg
1               5

<210> SEQ ID NO 32
<211> LENGTH: 6
<212> TYPE: PRT
<213> ORGANISM: Artificial Sequence
<220> FEATURE:
<223> OTHER INFORMATION: Peptide X Library

<400> SEQUENCE: 32

Ile Tyr Glu His Gly Arg
1               5

<210> SEQ ID NO 33
<211> LENGTH: 6
<212> TYPE: PRT
<213> ORGANISM: Artificial Sequence
<220> FEATURE:
<223> OTHER INFORMATION: Peptide X Library

<400> SEQUENCE: 33

Tyr Glu Ile His Gly Arg
1               5

<210> SEQ ID NO 34
<211> LENGTH: 6
<212> TYPE: PRT
<213> ORGANISM: Artificial Sequence
<220> FEATURE:
<223> OTHER INFORMATION: Peptide X Library

<400> SEQUENCE: 34

Glu Tyr Ile His Gly Arg
1               5

<210> SEQ ID NO 35
<211> LENGTH: 6
<212> TYPE: PRT
<213> ORGANISM: Artificial Sequence
<220> FEATURE:
<223> OTHER INFORMATION: Peptide X Library

```
<400> SEQUENCE: 35

Ile Glu Tyr His Gly Arg
1               5

<210> SEQ ID NO 36
<211> LENGTH: 6
<212> TYPE: PRT
<213> ORGANISM: Artificial Sequence
<220> FEATURE:
<223> OTHER INFORMATION: Peptide X Library

<400> SEQUENCE: 36

Glu Ile Tyr His Gly Arg
1               5

<210> SEQ ID NO 37
<211> LENGTH: 6
<212> TYPE: PRT
<213> ORGANISM: Artificial Sequence
<220> FEATURE:
<223> OTHER INFORMATION: Peptide X Library

<400> SEQUENCE: 37

Tyr His Glu Ile Gly Arg
1               5

<210> SEQ ID NO 38
<211> LENGTH: 6
<212> TYPE: PRT
<213> ORGANISM: Artificial Sequence
<220> FEATURE:
<223> OTHER INFORMATION: Peptide X Library

<400> SEQUENCE: 38

His Tyr Glu Ile Gly Arg
1               5

<210> SEQ ID NO 39
<211> LENGTH: 6
<212> TYPE: PRT
<213> ORGANISM: Artificial Sequence
<220> FEATURE:
<223> OTHER INFORMATION: Peptide X Library

<400> SEQUENCE: 39

Tyr Glu His Ile Gly Arg
1               5

<210> SEQ ID NO 40
<211> LENGTH: 6
<212> TYPE: PRT
<213> ORGANISM: Artificial Sequence
<220> FEATURE:
<223> OTHER INFORMATION: Peptide X Library

<400> SEQUENCE: 40

Glu Tyr His Ile Gly Arg
1               5

<210> SEQ ID NO 41
<211> LENGTH: 6
<212> TYPE: PRT
<213> ORGANISM: Artificial Sequence
<220> FEATURE:
<223> OTHER INFORMATION: Peptide X Library

<400> SEQUENCE: 41
```

His Glu Tyr Ile Gly Arg
1               5

<210> SEQ ID NO 42
<211> LENGTH: 6
<212> TYPE: PRT
<213> ORGANISM: Artificial Sequence
<220> FEATURE:
<223> OTHER INFORMATION: Peptide X Library

<400> SEQUENCE: 42

Glu His Tyr Ile Gly Arg
1               5

<210> SEQ ID NO 43
<211> LENGTH: 6
<212> TYPE: PRT
<213> ORGANISM: Artificial Sequence
<220> FEATURE:
<223> OTHER INFORMATION: Peptide X Library

<400> SEQUENCE: 43

Ile His Glu Tyr Gly Arg
1               5

<210> SEQ ID NO 44
<211> LENGTH: 6
<212> TYPE: PRT
<213> ORGANISM: Artificial Sequence
<220> FEATURE:
<223> OTHER INFORMATION: Peptide X Library

<400> SEQUENCE: 44

His Ile Glu Tyr Gly Arg
1               5

<210> SEQ ID NO 45
<211> LENGTH: 6
<212> TYPE: PRT
<213> ORGANISM: Artificial Sequence
<220> FEATURE:
<223> OTHER INFORMATION: Peptide X Library

<400> SEQUENCE: 45

Ile Glu His Tyr Gly Arg
1               5

<210> SEQ ID NO 46
<211> LENGTH: 6
<212> TYPE: PRT
<213> ORGANISM: Artificial Sequence
<220> FEATURE:
<223> OTHER INFORMATION: Peptide X Library

<400> SEQUENCE: 46

Glu Ile His Tyr Gly Arg
1               5

<210> SEQ ID NO 47
<211> LENGTH: 6
<212> TYPE: PRT
<213> ORGANISM: Artificial Sequence
<220> FEATURE:
<223> OTHER INFORMATION: Peptide X Library

<400> SEQUENCE: 47

```
His Glu Ile Tyr Gly Arg
 1               5

<210> SEQ ID NO 48
<211> LENGTH: 6
<212> TYPE: PRT
<213> ORGANISM: Artificial Sequence
<220> FEATURE:
<223> OTHER INFORMATION: Peptide X Library

<400> SEQUENCE: 48

Glu His Ile Tyr Gly Arg
 1               5

<210> SEQ ID NO 49
<211> LENGTH: 6
<212> TYPE: PRT
<213> ORGANISM: Artificial Sequence
<220> FEATURE:
<223> OTHER INFORMATION: Peptide X Library

<400> SEQUENCE: 49

Tyr Ile His Gly Glu Arg
 1               5

<210> SEQ ID NO 50
<211> LENGTH: 6
<212> TYPE: PRT
<213> ORGANISM: Artificial Sequence
<220> FEATURE:
<223> OTHER INFORMATION: Peptide X Library

<400> SEQUENCE: 50

Ile Tyr His Gly Glu Arg
 1               5

<210> SEQ ID NO 51
<211> LENGTH: 6
<212> TYPE: PRT
<213> ORGANISM: Artificial Sequence
<220> FEATURE:
<223> OTHER INFORMATION: Peptide X Library

<400> SEQUENCE: 51

Tyr His Ile Gly Glu Arg
 1               5

<210> SEQ ID NO 52
<211> LENGTH: 6
<212> TYPE: PRT
<213> ORGANISM: Artificial Sequence
<220> FEATURE:
<223> OTHER INFORMATION: Peptide X Library

<400> SEQUENCE: 52

His Tyr Ile Gly Glu Arg
 1               5

<210> SEQ ID NO 53
<211> LENGTH: 6
<212> TYPE: PRT
<213> ORGANISM: Artificial Sequence
<220> FEATURE:
<223> OTHER INFORMATION: Peptide X Library

<400> SEQUENCE: 53

Ile His Tyr Gly Glu Arg
```

```
1               5

<210> SEQ ID NO 54
<211> LENGTH: 6
<212> TYPE: PRT
<213> ORGANISM: Artificial Sequence
<220> FEATURE:
<223> OTHER INFORMATION: Peptide X Library
<223> OTHER INFORMATION: Peptide X Library

<400> SEQUENCE: 54

His Ile Tyr Gly Glu Arg
1               5

<210> SEQ ID NO 55
<211> LENGTH: 6
<212> TYPE: PRT
<213> ORGANISM: Artificial Sequence
<220> FEATURE:
<223> OTHER INFORMATION: Peptide X Library

<400> SEQUENCE: 55

Tyr Ile Gly His Glu Arg
1               5

<210> SEQ ID NO 56
<211> LENGTH: 6
<212> TYPE: PRT
<213> ORGANISM: Artificial Sequence
<220> FEATURE:
<223> OTHER INFORMATION: Peptide X Library

<400> SEQUENCE: 56

Ile Tyr Gly His Glu Arg
1               5

<210> SEQ ID NO 57
<211> LENGTH: 6
<212> TYPE: PRT
<213> ORGANISM: Artificial Sequence
<220> FEATURE:
<223> OTHER INFORMATION: Peptide X Library

<400> SEQUENCE: 57

Tyr Gly Ile His Glu Arg
1               5

<210> SEQ ID NO 58
<211> LENGTH: 6
<212> TYPE: PRT
<213> ORGANISM: Artificial Sequence
<220> FEATURE:
<223> OTHER INFORMATION: Peptide X Library

<400> SEQUENCE: 58

Gly Tyr Ile His Glu Arg
1               5

<210> SEQ ID NO 59
<211> LENGTH: 6
<212> TYPE: PRT
<213> ORGANISM: Artificial Sequence
<220> FEATURE:
<223> OTHER INFORMATION: Peptide X Library

<400> SEQUENCE: 59

Ile Gly Tyr His Glu Arg
```

```
                      1               5
```

<210> SEQ ID NO 60
<211> LENGTH: 6
<212> TYPE: PRT
<213> ORGANISM: Artificial Sequence
<220> FEATURE:
<223> OTHER INFORMATION: Peptide X Library

<400> SEQUENCE: 60

```
Gly Ile Tyr His Glu Arg
 1               5
```

<210> SEQ ID NO 61
<211> LENGTH: 6
<212> TYPE: PRT
<213> ORGANISM: Artificial Sequence
<220> FEATURE:
<223> OTHER INFORMATION: Peptide X Library

<400> SEQUENCE: 61

```
Tyr His Gly Ile Glu Arg
 1               5
```

<210> SEQ ID NO 62
<211> LENGTH: 6
<212> TYPE: PRT
<213> ORGANISM: Artificial Sequence
<220> FEATURE:
<223> OTHER INFORMATION: Peptide X Library

<400> SEQUENCE: 62

```
His Tyr Gly Ile Glu Arg
 1               5
```

<210> SEQ ID NO 63
<211> LENGTH: 6
<212> TYPE: PRT
<213> ORGANISM: Artificial Sequence
<220> FEATURE:
<223> OTHER INFORMATION: Peptide X Library

<400> SEQUENCE: 63

```
Tyr Gly His Ile Glu Arg
 1               5
```

<210> SEQ ID NO 64
<211> LENGTH: 6
<212> TYPE: PRT
<213> ORGANISM: Artificial Sequence
<220> FEATURE:
<223> OTHER INFORMATION: Peptide X Library

<400> SEQUENCE: 64

```
Gly Tyr His Ile Glu Arg
 1               5
```

<210> SEQ ID NO 65
<211> LENGTH: 6
<212> TYPE: PRT
<213> ORGANISM: Artificial Sequence
<220> FEATURE:
<223> OTHER INFORMATION: Peptide X Library

<400> SEQUENCE: 65

```
His Gly Tyr Ile Glu Arg
 1               5
```

```
<210> SEQ ID NO 66
<211> LENGTH: 6
<212> TYPE: PRT
<213> ORGANISM: Artificial Sequence
<220> FEATURE:
<223> OTHER INFORMATION: Peptide X Library

<400> SEQUENCE: 66

Gly His Tyr Ile Glu Arg
 1               5

<210> SEQ ID NO 67
<211> LENGTH: 6
<212> TYPE: PRT
<213> ORGANISM: Artificial Sequence
<220> FEATURE:
<223> OTHER INFORMATION: Peptide X Library

<400> SEQUENCE: 67

Ile His Gly Tyr Glu Arg
 1               5

<210> SEQ ID NO 68
<211> LENGTH: 6
<212> TYPE: PRT
<213> ORGANISM: Artificial Sequence
<220> FEATURE:
<223> OTHER INFORMATION: Peptide X Library

<400> SEQUENCE: 68

His Ile Gly Tyr Glu Arg
 1               5

<210> SEQ ID NO 69
<211> LENGTH: 6
<212> TYPE: PRT
<213> ORGANISM: Artificial Sequence
<220> FEATURE:
<223> OTHER INFORMATION: Peptide X Library

<400> SEQUENCE: 69

Ile Gly His Tyr Glu Arg
 1               5

<210> SEQ ID NO 70
<211> LENGTH: 6
<212> TYPE: PRT
<213> ORGANISM: Artificial Sequence
<220> FEATURE:
<223> OTHER INFORMATION: Peptide X Library

<400> SEQUENCE: 70

Gly Ile His Tyr Glu Arg
 1               5

<210> SEQ ID NO 71
<211> LENGTH: 6
<212> TYPE: PRT
<213> ORGANISM: Artificial Sequence
<220> FEATURE:
<223> OTHER INFORMATION: Peptide X Library

<400> SEQUENCE: 71

His Gly Ile Tyr Glu Arg
 1               5
```

<210> SEQ ID NO 72
<211> LENGTH: 6
<212> TYPE: PRT
<213> ORGANISM: Artificial Sequence
<220> FEATURE:
<223> OTHER INFORMATION: Peptide X Library

<400> SEQUENCE: 72

Gly His Ile Tyr Glu Arg
 1               5

<210> SEQ ID NO 73
<211> LENGTH: 6
<212> TYPE: PRT
<213> ORGANISM: Artificial Sequence
<220> FEATURE:
<223> OTHER INFORMATION: Peptide X Library

<400> SEQUENCE: 73

Tyr Ile Glu Gly His Arg
 1               5

<210> SEQ ID NO 74
<211> LENGTH: 6
<212> TYPE: PRT
<213> ORGANISM: Artificial Sequence
<220> FEATURE:
<223> OTHER INFORMATION: Peptide X Library

<400> SEQUENCE: 74

Ile Tyr Glu Gly His Arg
 1               5

<210> SEQ ID NO 75
<211> LENGTH: 6
<212> TYPE: PRT
<213> ORGANISM: Artificial Sequence
<220> FEATURE:
<223> OTHER INFORMATION: Peptide X Library

<400> SEQUENCE: 75

Tyr Glu Ile Gly His Arg
 1               5

<210> SEQ ID NO 76
<211> LENGTH: 6
<212> TYPE: PRT
<213> ORGANISM: Artificial Sequence
<220> FEATURE:
<223> OTHER INFORMATION: Peptide X Library

<400> SEQUENCE: 76

Glu Tyr Ile Gly His Arg
 1               5

<210> SEQ ID NO 77
<211> LENGTH: 6
<212> TYPE: PRT
<213> ORGANISM: Artificial Sequence
<220> FEATURE:
<223> OTHER INFORMATION: Peptide X Library

<400> SEQUENCE: 77

Ile Glu Tyr Gly His Arg
 1               5

```
<210> SEQ ID NO 78
<211> LENGTH: 6
<212> TYPE: PRT
<213> ORGANISM: Artificial Sequence
<220> FEATURE:
<223> OTHER INFORMATION: Peptide X Library

<400> SEQUENCE: 78

Glu Ile Tyr Gly His Arg
 1               5

<210> SEQ ID NO 79
<211> LENGTH: 6
<212> TYPE: PRT
<213> ORGANISM: Artificial Sequence
<220> FEATURE:
<223> OTHER INFORMATION: Peptide X Library

<400> SEQUENCE: 79

Tyr Ile Gly Glu His Arg
 1               5

<210> SEQ ID NO 80
<211> LENGTH: 6
<212> TYPE: PRT
<213> ORGANISM: Artificial Sequence
<220> FEATURE:
<223> OTHER INFORMATION: Peptide X Library

<400> SEQUENCE: 80

Ile Tyr Gly Glu His Arg
 1               5

<210> SEQ ID NO 81
<211> LENGTH: 6
<212> TYPE: PRT
<213> ORGANISM: Artificial Sequence
<220> FEATURE:
<223> OTHER INFORMATION: Peptide X Library

<400> SEQUENCE: 81

Tyr Gly Ile Glu His Arg
 1               5

<210> SEQ ID NO 82
<211> LENGTH: 6
<212> TYPE: PRT
<213> ORGANISM: Artificial Sequence
<220> FEATURE:
<223> OTHER INFORMATION: Peptide X Library

<400> SEQUENCE: 82

Gly Tyr Ile Glu His Arg
 1               5

<210> SEQ ID NO 83
<211> LENGTH: 6
<212> TYPE: PRT
<213> ORGANISM: Artificial Sequence
<220> FEATURE:
<223> OTHER INFORMATION: Peptide X Library

<400> SEQUENCE: 83

Ile Gly Tyr Glu His Arg
 1               5

<210> SEQ ID NO 84
```

```
<211> LENGTH: 6
<212> TYPE: PRT
<213> ORGANISM: Artificial Sequence
<220> FEATURE:
<223> OTHER INFORMATION: Peptide X Library

<400> SEQUENCE: 84

Gly Ile Tyr Glu His Arg
 1               5

<210> SEQ ID NO 85
<211> LENGTH: 6
<212> TYPE: PRT
<213> ORGANISM: Artificial Sequence
<220> FEATURE:
<223> OTHER INFORMATION: Peptide X Library

<400> SEQUENCE: 85

Tyr Glu Gly Ile His Arg
 1               5

<210> SEQ ID NO 86
<211> LENGTH: 6
<212> TYPE: PRT
<213> ORGANISM: Artificial Sequence
<220> FEATURE:
<223> OTHER INFORMATION: Peptide X Library

<400> SEQUENCE: 86

Glu Tyr Gly Ile His Arg
 1               5

<210> SEQ ID NO 87
<211> LENGTH: 6
<212> TYPE: PRT
<213> ORGANISM: Artificial Sequence
<220> FEATURE:
<223> OTHER INFORMATION: Peptide X Library

<400> SEQUENCE: 87

Tyr Gly Glu Ile His Arg
 1               5

<210> SEQ ID NO 88
<211> LENGTH: 6
<212> TYPE: PRT
<213> ORGANISM: Artificial Sequence
<220> FEATURE:
<223> OTHER INFORMATION: Peptide X Library

<400> SEQUENCE: 88

Gly Tyr Glu Ile His Arg
 1               5

<210> SEQ ID NO 89
<211> LENGTH: 6
<212> TYPE: PRT
<213> ORGANISM: Artificial Sequence
<220> FEATURE:
<223> OTHER INFORMATION: Peptide X Library

<400> SEQUENCE: 89

Glu Gly Tyr Ile His Arg
 1               5

<210> SEQ ID NO 90
<211> LENGTH: 6
```

```
<212> TYPE: PRT
<213> ORGANISM: Artificial Sequence
<220> FEATURE:
<223> OTHER INFORMATION: Peptide X Library

<400> SEQUENCE: 90

Gly Glu Tyr Ile His Arg
 1               5

<210> SEQ ID NO 91
<211> LENGTH: 6
<212> TYPE: PRT
<213> ORGANISM: Artificial Sequence
<220> FEATURE:
<223> OTHER INFORMATION: Peptide X Library

<400> SEQUENCE: 91

Ile Glu Gly Tyr His Arg
 1               5

<210> SEQ ID NO 92
<211> LENGTH: 6
<212> TYPE: PRT
<213> ORGANISM: Artificial Sequence
<220> FEATURE:
<223> OTHER INFORMATION: Peptide X Library

<400> SEQUENCE: 92

Glu Ile Gly Tyr His Arg
 1               5

<210> SEQ ID NO 93
<211> LENGTH: 6
<212> TYPE: PRT
<213> ORGANISM: Artificial Sequence
<220> FEATURE:
<223> OTHER INFORMATION: Peptide X Library

<400> SEQUENCE: 93

Ile Gly Glu Tyr His Arg
 1               5

<210> SEQ ID NO 94
<211> LENGTH: 6
<212> TYPE: PRT
<213> ORGANISM: Artificial Sequence
<220> FEATURE:
<223> OTHER INFORMATION: Peptide X Library

<400> SEQUENCE: 94

Gly Ile Glu Tyr His Arg
 1               5

<210> SEQ ID NO 95
<211> LENGTH: 6
<212> TYPE: PRT
<213> ORGANISM: Artificial Sequence
<220> FEATURE:
<223> OTHER INFORMATION: Peptide X Library

<400> SEQUENCE: 95

Glu Gly Ile Tyr His Arg
 1               5

<210> SEQ ID NO 96
<211> LENGTH: 6
<212> TYPE: PRT
```

```
<213> ORGANISM: Artificial Sequence
<220> FEATURE:
<223> OTHER INFORMATION: Peptide X Library

<400> SEQUENCE: 96

Gly Glu Ile Tyr His Arg
 1               5

<210> SEQ ID NO 97
<211> LENGTH: 6
<212> TYPE: PRT
<213> ORGANISM: Artificial Sequence
<220> FEATURE:
<223> OTHER INFORMATION: Peptide X Library

<400> SEQUENCE: 97

Tyr His Glu Gly Ile Arg
 1               5

<210> SEQ ID NO 98
<211> LENGTH: 6
<212> TYPE: PRT
<213> ORGANISM: Artificial Sequence
<220> FEATURE:
<223> OTHER INFORMATION: Peptide X Library

<400> SEQUENCE: 98

His Tyr Glu Gly Ile Arg
 1               5

<210> SEQ ID NO 99
<211> LENGTH: 6
<212> TYPE: PRT
<213> ORGANISM: Artificial Sequence
<220> FEATURE:
<223> OTHER INFORMATION: Peptide X Library

<400> SEQUENCE: 99

Tyr Glu His Gly Ile Arg
 1               5

<210> SEQ ID NO 100
<211> LENGTH: 6
<212> TYPE: PRT
<213> ORGANISM: Artificial Sequence
<220> FEATURE:
<223> OTHER INFORMATION: Peptide X Library

<400> SEQUENCE: 100

Glu Tyr His Gly Ile Arg
 1               5

<210> SEQ ID NO 101
<211> LENGTH: 6
<212> TYPE: PRT
<213> ORGANISM: Artificial Sequence
<220> FEATURE:
<223> OTHER INFORMATION: Peptide X Library

<400> SEQUENCE: 101

His Glu Tyr Gly Ile Arg
 1               5

<210> SEQ ID NO 102
<211> LENGTH: 6
<212> TYPE: PRT
<213> ORGANISM: Artificial Sequence
```

```
<220> FEATURE:
<223> OTHER INFORMATION: Peptide X Library

<400> SEQUENCE: 102

Glu His Tyr Gly Ile Arg
 1               5

<210> SEQ ID NO 103
<211> LENGTH: 6
<212> TYPE: PRT
<213> ORGANISM: Artificial Sequence
<220> FEATURE:
<223> OTHER INFORMATION: Peptide X Library

<400> SEQUENCE: 103

Tyr His Gly Glu Ile Arg
 1               5

<210> SEQ ID NO 104
<211> LENGTH: 6
<212> TYPE: PRT
<213> ORGANISM: Artificial Sequence
<220> FEATURE:
<223> OTHER INFORMATION: Peptide X Library

<400> SEQUENCE: 104

His Tyr Gly Glu Ile Arg
 1               5

<210> SEQ ID NO 105
<211> LENGTH: 6
<212> TYPE: PRT
<213> ORGANISM: Artificial Sequence
<220> FEATURE:
<223> OTHER INFORMATION: Peptide X Library

<400> SEQUENCE: 105

Tyr Gly His Glu Ile Arg
 1               5

<210> SEQ ID NO 106
<211> LENGTH: 6
<212> TYPE: PRT
<213> ORGANISM: Artificial Sequence
<220> FEATURE:
<223> OTHER INFORMATION: Peptide X Library

<400> SEQUENCE: 106

Gly Tyr His Glu Ile Arg
 1               5

<210> SEQ ID NO 107
<211> LENGTH: 6
<212> TYPE: PRT
<213> ORGANISM: Artificial Sequence
<220> FEATURE:
<223> OTHER INFORMATION: Peptide X Library
<223> OTHER INFORMATION: Peptide X Library

<400> SEQUENCE: 107

His Gly Tyr Glu Ile Arg
 1               5

<210> SEQ ID NO 108
<211> LENGTH: 6
<212> TYPE: PRT
<213> ORGANISM: Artificial Sequence
```

```
<220> FEATURE:
<223> OTHER INFORMATION: Peptide X Library

<400> SEQUENCE: 108

Gly His Tyr Glu Ile Arg
 1               5

<210> SEQ ID NO 109
<211> LENGTH: 6
<212> TYPE: PRT
<213> ORGANISM: Artificial Sequence
<220> FEATURE:
<223> OTHER INFORMATION: Peptide X Library

<400> SEQUENCE: 109

Tyr Glu Gly His Ile Arg
 1               5

<210> SEQ ID NO 110
<211> LENGTH: 6
<212> TYPE: PRT
<213> ORGANISM: Artificial Sequence
<220> FEATURE:
<223> OTHER INFORMATION: Peptide X Library

<400> SEQUENCE: 110

Glu Tyr Gly His Ile Arg
 1               5

<210> SEQ ID NO 111
<211> LENGTH: 6
<212> TYPE: PRT
<213> ORGANISM: Artificial Sequence
<220> FEATURE:
<223> OTHER INFORMATION: Peptide X Library

<400> SEQUENCE: 111

Tyr Gly Glu His Ile Arg
 1               5

<210> SEQ ID NO 112
<211> LENGTH: 6
<212> TYPE: PRT
<213> ORGANISM: Artificial Sequence
<220> FEATURE:
<223> OTHER INFORMATION: Peptide X Library

<400> SEQUENCE: 112

Gly Tyr Glu His Ile Arg
 1               5

<210> SEQ ID NO 113
<211> LENGTH: 6
<212> TYPE: PRT
<213> ORGANISM: Artificial Sequence
<220> FEATURE:
<223> OTHER INFORMATION: Peptide X Library

<400> SEQUENCE: 113

Glu Gly Tyr His Ile Arg
 1               5

<210> SEQ ID NO 114
<211> LENGTH: 6
<212> TYPE: PRT
<213> ORGANISM: Artificial Sequence
<220> FEATURE:
```

<223> OTHER INFORMATION: Peptide X Library

<400> SEQUENCE: 114

Gly Glu Tyr His Ile Arg
 1               5

<210> SEQ ID NO 115
<211> LENGTH: 6
<212> TYPE: PRT
<213> ORGANISM: Artificial Sequence
<220> FEATURE:
<223> OTHER INFORMATION: Peptide X Library

<400> SEQUENCE: 115

His Glu Gly Tyr Ile Arg
 1               5

<210> SEQ ID NO 116
<211> LENGTH: 6
<212> TYPE: PRT
<213> ORGANISM: Artificial Sequence
<220> FEATURE:
<223> OTHER INFORMATION: Peptide X Library

<400> SEQUENCE: 116

Glu His Gly Tyr Ile Arg
 1               5

<210> SEQ ID NO 117
<211> LENGTH: 6
<212> TYPE: PRT
<213> ORGANISM: Artificial Sequence
<220> FEATURE:
<223> OTHER INFORMATION: Peptide X Library

<400> SEQUENCE: 117

His Gly Glu Tyr Ile Arg
 1               5

<210> SEQ ID NO 118
<211> LENGTH: 6
<212> TYPE: PRT
<213> ORGANISM: Artificial Sequence
<220> FEATURE:
<223> OTHER INFORMATION: Peptide X Library

<400> SEQUENCE: 118

Gly His Glu Tyr Ile Arg
 1               5

<210> SEQ ID NO 119
<211> LENGTH: 6
<212> TYPE: PRT
<213> ORGANISM: Artificial Sequence
<220> FEATURE:
<223> OTHER INFORMATION: Peptide X Library

<400> SEQUENCE: 119

Glu Gly His Tyr Ile Arg
 1               5

<210> SEQ ID NO 120
<211> LENGTH: 6
<212> TYPE: PRT
<213> ORGANISM: Artificial Sequence
<220> FEATURE:
<223> OTHER INFORMATION: Peptide X Library

```
<400> SEQUENCE: 120

Gly Glu His Tyr Ile Arg
 1               5

<210> SEQ ID NO 121
<211> LENGTH: 6
<212> TYPE: PRT
<213> ORGANISM: Artificial Sequence
<220> FEATURE:
<223> OTHER INFORMATION: Peptide X Library

<400> SEQUENCE: 121

Ile His Glu Gly Tyr Arg
 1               5

<210> SEQ ID NO 122
<211> LENGTH: 6
<212> TYPE: PRT
<213> ORGANISM: Artificial Sequence
<220> FEATURE:
<223> OTHER INFORMATION: Peptide X Library

<400> SEQUENCE: 122

His Ile Glu Gly Tyr Arg
 1               5

<210> SEQ ID NO 123
<211> LENGTH: 6
<212> TYPE: PRT
<213> ORGANISM: Artificial Sequence
<220> FEATURE:
<223> OTHER INFORMATION: Peptide X Library

<400> SEQUENCE: 123

Ile Glu His Gly Tyr Arg
 1               5

<210> SEQ ID NO 124
<211> LENGTH: 6
<212> TYPE: PRT
<213> ORGANISM: Artificial Sequence
<220> FEATURE:
<223> OTHER INFORMATION: Peptide X Library

<400> SEQUENCE: 124

Glu Ile His Gly Tyr Arg
 1               5

<210> SEQ ID NO 125
<211> LENGTH: 6
<212> TYPE: PRT
<213> ORGANISM: Artificial Sequence
<220> FEATURE:
<223> OTHER INFORMATION: Peptide X Library

<400> SEQUENCE: 125

His Glu Ile Gly Tyr Arg
 1               5

<210> SEQ ID NO 126
<211> LENGTH: 6
<212> TYPE: PRT
<213> ORGANISM: Artificial Sequence
<220> FEATURE:
<223> OTHER INFORMATION: Peptide X Library
```

```
<400> SEQUENCE: 126

Glu His Ile Gly Tyr Arg
1               5

<210> SEQ ID NO 127
<211> LENGTH: 6
<212> TYPE: PRT
<213> ORGANISM: Artificial Sequence
<220> FEATURE:
<223> OTHER INFORMATION: Peptide X Library

<400> SEQUENCE: 127

Ile His Gly Glu Tyr Arg
1               5

<210> SEQ ID NO 128
<211> LENGTH: 6
<212> TYPE: PRT
<213> ORGANISM: Artificial Sequence
<220> FEATURE:
<223> OTHER INFORMATION: Peptide X Library

<400> SEQUENCE: 128

His Ile Gly Glu Tyr Arg
1               5

<210> SEQ ID NO 129
<211> LENGTH: 6
<212> TYPE: PRT
<213> ORGANISM: Artificial Sequence
<220> FEATURE:
<223> OTHER INFORMATION: Peptide X Library

<400> SEQUENCE: 129

Ile Gly His Glu Tyr Arg
1               5

<210> SEQ ID NO 130
<211> LENGTH: 6
<212> TYPE: PRT
<213> ORGANISM: Artificial Sequence
<220> FEATURE:
<223> OTHER INFORMATION: Peptide X Library

<400> SEQUENCE: 130

Gly Ile His Glu Tyr Arg
1               5

<210> SEQ ID NO 131
<211> LENGTH: 6
<212> TYPE: PRT
<213> ORGANISM: Artificial Sequence
<220> FEATURE:
<223> OTHER INFORMATION: Peptide X Library

<400> SEQUENCE: 131

His Gly Ile Glu Tyr Arg
1               5

<210> SEQ ID NO 132
<211> LENGTH: 6
<212> TYPE: PRT
<213> ORGANISM: Artificial Sequence
<220> FEATURE:
<223> OTHER INFORMATION: Peptide X Library

<400> SEQUENCE: 132
```

Gly His Ile Glu Tyr Arg
1               5

<210> SEQ ID NO 133
<211> LENGTH: 6
<212> TYPE: PRT
<213> ORGANISM: Artificial Sequence
<220> FEATURE:
<223> OTHER INFORMATION: Peptide X Library

<400> SEQUENCE: 133

Ile Glu Gly His Tyr Arg
1               5

<210> SEQ ID NO 134
<211> LENGTH: 6
<212> TYPE: PRT
<213> ORGANISM: Artificial Sequence
<220> FEATURE:
<223> OTHER INFORMATION: Peptide X Library

<400> SEQUENCE: 134

Glu Ile Gly His Tyr Arg
1               5

<210> SEQ ID NO 135
<211> LENGTH: 6
<212> TYPE: PRT
<213> ORGANISM: Artificial Sequence
<220> FEATURE:
<223> OTHER INFORMATION: Peptide X Library

<400> SEQUENCE: 135

Ile Gly Glu His Tyr Arg
1               5

<210> SEQ ID NO 136
<211> LENGTH: 6
<212> TYPE: PRT
<213> ORGANISM: Artificial Sequence
<220> FEATURE:
<223> OTHER INFORMATION: Peptide X Library

<400> SEQUENCE: 136

Gly Ile Glu His Tyr Arg
1               5

<210> SEQ ID NO 137
<211> LENGTH: 6
<212> TYPE: PRT
<213> ORGANISM: Artificial Sequence
<220> FEATURE:
<223> OTHER INFORMATION: Peptide X Library

<400> SEQUENCE: 137

Glu Gly Ile His Tyr Arg
1               5

<210> SEQ ID NO 138
<211> LENGTH: 6
<212> TYPE: PRT
<213> ORGANISM: Artificial Sequence
<220> FEATURE:
<223> OTHER INFORMATION: Peptide X Library

<400> SEQUENCE: 138

Gly Glu Ile His Tyr Arg
1               5

<210> SEQ ID NO 139
<211> LENGTH: 6
<212> TYPE: PRT
<213> ORGANISM: Artificial Sequence
<220> FEATURE:
<223> OTHER INFORMATION: Peptide X Library

<400> SEQUENCE: 139

His Glu Gly Ile Tyr Arg
1               5

<210> SEQ ID NO 140
<211> LENGTH: 6
<212> TYPE: PRT
<213> ORGANISM: Artificial Sequence
<220> FEATURE:
<223> OTHER INFORMATION: Peptide X Library

<400> SEQUENCE: 140

Glu His Gly Ile Tyr Arg
1               5

<210> SEQ ID NO 141
<211> LENGTH: 6
<212> TYPE: PRT
<213> ORGANISM: Artificial Sequence
<220> FEATURE:
<223> OTHER INFORMATION: Peptide X Library

<400> SEQUENCE: 141

His Gly Glu Ile Tyr Arg
1               5

<210> SEQ ID NO 142
<211> LENGTH: 6
<212> TYPE: PRT
<213> ORGANISM: Artificial Sequence
<220> FEATURE:
<223> OTHER INFORMATION: Peptide X Library

<400> SEQUENCE: 142

Gly His Glu Ile Tyr Arg
1               5

<210> SEQ ID NO 143
<211> LENGTH: 6
<212> TYPE: PRT
<213> ORGANISM: Artificial Sequence
<220> FEATURE:
<223> OTHER INFORMATION: Peptide X Library

<400> SEQUENCE: 143

Glu Gly His Ile Tyr Arg
1               5

<210> SEQ ID NO 144
<211> LENGTH: 6
<212> TYPE: PRT
<213> ORGANISM: Artificial Sequence
<220> FEATURE:
<223> OTHER INFORMATION: Peptide X Library

<400> SEQUENCE: 144

Gly Glu His Ile Tyr Arg

<210> SEQ ID NO 145
<211> LENGTH: 6
<212> TYPE: PRT
<213> ORGANISM: Artificial Sequence
<220> FEATURE:
<223> OTHER INFORMATION: Peptide X Library

<400> SEQUENCE: 145

Tyr Ile His Asp Ala Arg
1               5

<210> SEQ ID NO 146
<211> LENGTH: 6
<212> TYPE: PRT
<213> ORGANISM: Artificial Sequence
<220> FEATURE:
<223> OTHER INFORMATION: Peptide X Library

<400> SEQUENCE: 146

Ile Tyr His Asp Ala Arg
1               5

<210> SEQ ID NO 147
<211> LENGTH: 6
<212> TYPE: PRT
<213> ORGANISM: Artificial Sequence
<220> FEATURE:
<223> OTHER INFORMATION: Peptide X Library

<400> SEQUENCE: 147

Tyr His Ile Asp Ala Arg
1               5

<210> SEQ ID NO 148
<211> LENGTH: 6
<212> TYPE: PRT
<213> ORGANISM: Artificial Sequence
<220> FEATURE:
<223> OTHER INFORMATION: Peptide X Library

<400> SEQUENCE: 148

His Tyr Ile Asp Ala Arg
1               5

<210> SEQ ID NO 149
<211> LENGTH: 6
<212> TYPE: PRT
<213> ORGANISM: Artificial Sequence
<220> FEATURE:
<223> OTHER INFORMATION: Peptide X Library

<400> SEQUENCE: 149

Ile His Tyr Asp Ala Arg
1               5

<210> SEQ ID NO 150
<211> LENGTH: 6
<212> TYPE: PRT
<213> ORGANISM: Artificial Sequence
<220> FEATURE:
<223> OTHER INFORMATION: Peptide X Library

<400> SEQUENCE: 150

His Ile Tyr Asp Ala Arg
1               5

```
<210> SEQ ID NO 151
<211> LENGTH: 6
<212> TYPE: PRT
<213> ORGANISM: Artificial Sequence
<220> FEATURE:
<223> OTHER INFORMATION: Peptide X Library

<400> SEQUENCE: 151

Tyr Ile Asp His Ala Arg
1               5

<210> SEQ ID NO 152
<211> LENGTH: 6
<212> TYPE: PRT
<213> ORGANISM: Artificial Sequence
<220> FEATURE:
<223> OTHER INFORMATION: Peptide X Library

<400> SEQUENCE: 152

Ile Tyr Asp His Ala Arg
1               5

<210> SEQ ID NO 153
<211> LENGTH: 6
<212> TYPE: PRT
<213> ORGANISM: Artificial Sequence
<220> FEATURE:
<223> OTHER INFORMATION: Peptide X Library

<400> SEQUENCE: 153

Tyr Asp Ile His Ala Arg
1               5

<210> SEQ ID NO 154
<211> LENGTH: 6
<212> TYPE: PRT
<213> ORGANISM: Artificial Sequence
<220> FEATURE:
<223> OTHER INFORMATION: Peptide X Library

<400> SEQUENCE: 154

Asp Tyr Ile His Ala Arg
1               5

<210> SEQ ID NO 155
<211> LENGTH: 6
<212> TYPE: PRT
<213> ORGANISM: Artificial Sequence
<220> FEATURE:
<223> OTHER INFORMATION: Peptide X Library

<400> SEQUENCE: 155

Ile Asp Tyr His Ala Arg
1               5

<210> SEQ ID NO 156
<211> LENGTH: 6
<212> TYPE: PRT
<213> ORGANISM: Artificial Sequence
<220> FEATURE:
<223> OTHER INFORMATION: Peptide X Library

<400> SEQUENCE: 156

Asp Ile Tyr His Ala Arg
1               5
```

```
<210> SEQ ID NO 157
<211> LENGTH: 6
<212> TYPE: PRT
<213> ORGANISM: Artificial Sequence
<220> FEATURE:
<223> OTHER INFORMATION: Peptide X Library

<400> SEQUENCE: 157

Tyr His Asp Ile Ala Arg
 1               5

<210> SEQ ID NO 158
<211> LENGTH: 6
<212> TYPE: PRT
<213> ORGANISM: Artificial Sequence
<220> FEATURE:
<223> OTHER INFORMATION: Peptide X Library

<400> SEQUENCE: 158

His Tyr Asp Ile Ala Arg
 1               5

<210> SEQ ID NO 159
<211> LENGTH: 6
<212> TYPE: PRT
<213> ORGANISM: Artificial Sequence
<220> FEATURE:
<223> OTHER INFORMATION: Peptide X Library

<400> SEQUENCE: 159

Tyr Asp His Ile Ala Arg
 1               5

<210> SEQ ID NO 160
<211> LENGTH: 6
<212> TYPE: PRT
<213> ORGANISM: Artificial Sequence
<220> FEATURE:
<223> OTHER INFORMATION: Peptide X Library
<223> OTHER INFORMATION: Peptide X Library

<400> SEQUENCE: 160

Asp Tyr His Ile Ala Arg
 1               5

<210> SEQ ID NO 161
<211> LENGTH: 6
<212> TYPE: PRT
<213> ORGANISM: Artificial Sequence
<220> FEATURE:
<223> OTHER INFORMATION: Peptide X Library

<400> SEQUENCE: 161

His Asp Tyr Ile Ala Arg
 1               5

<210> SEQ ID NO 162
<211> LENGTH: 6
<212> TYPE: PRT
<213> ORGANISM: Artificial Sequence
<220> FEATURE:
<223> OTHER INFORMATION: Peptide X Library

<400> SEQUENCE: 162

Asp His Tyr Ile Ala Arg
 1               5
```

```
<210> SEQ ID NO 163
<211> LENGTH: 6
<212> TYPE: PRT
<213> ORGANISM: Artificial Sequence
<220> FEATURE:
<223> OTHER INFORMATION: Peptide X Library

<400> SEQUENCE: 163

Ile His Asp Tyr Ala Arg
 1               5

<210> SEQ ID NO 164
<211> LENGTH: 6
<212> TYPE: PRT
<213> ORGANISM: Artificial Sequence
<220> FEATURE:
<223> OTHER INFORMATION: Peptide X Library

<400> SEQUENCE: 164

His Ile Asp Tyr Ala Arg
 1               5

<210> SEQ ID NO 165
<211> LENGTH: 6
<212> TYPE: PRT
<213> ORGANISM: Artificial Sequence
<220> FEATURE:
<223> OTHER INFORMATION: Peptide X Library

<400> SEQUENCE: 165

Ile Asp His Tyr Ala Arg
 1               5

<210> SEQ ID NO 166
<211> LENGTH: 6
<212> TYPE: PRT
<213> ORGANISM: Artificial Sequence
<220> FEATURE:
<223> OTHER INFORMATION: Peptide X Library

<400> SEQUENCE: 166

Asp Ile His Tyr Ala Arg
 1               5

<210> SEQ ID NO 167
<211> LENGTH: 6
<212> TYPE: PRT
<213> ORGANISM: Artificial Sequence
<220> FEATURE:
<223> OTHER INFORMATION: Peptide X Library

<400> SEQUENCE: 167

His Asp Ile Tyr Ala Arg
 1               5

<210> SEQ ID NO 168
<211> LENGTH: 6
<212> TYPE: PRT
<213> ORGANISM: Artificial Sequence
<220> FEATURE:
<223> OTHER INFORMATION: Peptide X Library

<400> SEQUENCE: 168

Asp His Ile Tyr Ala Arg
 1               5
```

```
<210> SEQ ID NO 169
<211> LENGTH: 6
<212> TYPE: PRT
<213> ORGANISM: Artificial Sequence
<220> FEATURE:
<223> OTHER INFORMATION: Peptide X Library

<400> SEQUENCE: 169

Tyr Ile His Ala Asp Arg
 1               5

<210> SEQ ID NO 170
<211> LENGTH: 6
<212> TYPE: PRT
<213> ORGANISM: Artificial Sequence
<220> FEATURE:
<223> OTHER INFORMATION: Peptide X Library

<400> SEQUENCE: 170

Ile Tyr His Ala Asp Arg
 1               5

<210> SEQ ID NO 171
<211> LENGTH: 6
<212> TYPE: PRT
<213> ORGANISM: Artificial Sequence
<220> FEATURE:
<223> OTHER INFORMATION: Peptide X Library

<400> SEQUENCE: 171

Tyr His Ile Ala Asp Arg
 1               5

<210> SEQ ID NO 172
<211> LENGTH: 6
<212> TYPE: PRT
<213> ORGANISM: Artificial Sequence
<220> FEATURE:
<223> OTHER INFORMATION: Peptide X Library

<400> SEQUENCE: 172

His Tyr Ile Ala Asp Arg
 1               5

<210> SEQ ID NO 173
<211> LENGTH: 6
<212> TYPE: PRT
<213> ORGANISM: Artificial Sequence
<220> FEATURE:
<223> OTHER INFORMATION: Peptide X Library

<400> SEQUENCE: 173

Ile His Tyr Ala Asp Arg
 1               5

<210> SEQ ID NO 174
<211> LENGTH: 6
<212> TYPE: PRT
<213> ORGANISM: Artificial Sequence
<220> FEATURE:
<223> OTHER INFORMATION: Peptide X Library

<400> SEQUENCE: 174

His Ile Tyr Ala Asp Arg
 1               5

<210> SEQ ID NO 175
```

```
<211> LENGTH: 6
<212> TYPE: PRT
<213> ORGANISM: Artificial Sequence
<220> FEATURE:
<223> OTHER INFORMATION: Peptide X Library

<400> SEQUENCE: 175

Tyr Ile Ala His Asp Arg
 1               5

<210> SEQ ID NO 176
<211> LENGTH: 6
<212> TYPE: PRT
<213> ORGANISM: Artificial Sequence
<220> FEATURE:
<223> OTHER INFORMATION: Peptide X Library

<400> SEQUENCE: 176

Ile Tyr Ala His Asp Arg
 1               5

<210> SEQ ID NO 177
<211> LENGTH: 6
<212> TYPE: PRT
<213> ORGANISM: Artificial Sequence
<220> FEATURE:
<223> OTHER INFORMATION: Peptide X Library

<400> SEQUENCE: 177

Tyr Ala Ile His Asp Arg
 1               5

<210> SEQ ID NO 178
<211> LENGTH: 6
<212> TYPE: PRT
<213> ORGANISM: Artificial Sequence
<220> FEATURE:
<223> OTHER INFORMATION: Peptide X Library

<400> SEQUENCE: 178

Ala Tyr Ile His Asp Arg
 1               5

<210> SEQ ID NO 179
<211> LENGTH: 6
<212> TYPE: PRT
<213> ORGANISM: Artificial Sequence
<220> FEATURE:
<223> OTHER INFORMATION: Peptide X Library

<400> SEQUENCE: 179

Ile Ala Tyr His Asp Arg
 1               5

<210> SEQ ID NO 180
<211> LENGTH: 6
<212> TYPE: PRT
<213> ORGANISM: Artificial Sequence
<220> FEATURE:
<223> OTHER INFORMATION: Peptide X Library

<400> SEQUENCE: 180

Ala Ile Tyr His Asp Arg
 1               5

<210> SEQ ID NO 181
<211> LENGTH: 6
```

-continued

```
<212> TYPE: PRT
<213> ORGANISM: Artificial Sequence
<220> FEATURE:
<223> OTHER INFORMATION: Peptide X Library

<400> SEQUENCE: 181

Tyr His Ala Ile Asp Arg
 1               5

<210> SEQ ID NO 182
<211> LENGTH: 6
<212> TYPE: PRT
<213> ORGANISM: Artificial Sequence
<220> FEATURE:
<223> OTHER INFORMATION: Peptide X Library

<400> SEQUENCE: 182

His Tyr Ala Ile Asp Arg
 1               5

<210> SEQ ID NO 183
<211> LENGTH: 6
<212> TYPE: PRT
<213> ORGANISM: Artificial Sequence
<220> FEATURE:
<223> OTHER INFORMATION: Peptide X Library

<400> SEQUENCE: 183

Tyr Ala His Ile Asp Arg
 1               5

<210> SEQ ID NO 184
<211> LENGTH: 6
<212> TYPE: PRT
<213> ORGANISM: Artificial Sequence
<220> FEATURE:
<223> OTHER INFORMATION: Peptide X Library

<400> SEQUENCE: 184

Ala Tyr His Ile Asp Arg
 1               5

<210> SEQ ID NO 185
<211> LENGTH: 6
<212> TYPE: PRT
<213> ORGANISM: Artificial Sequence
<220> FEATURE:
<223> OTHER INFORMATION: Peptide X Library

<400> SEQUENCE: 185

His Ala Tyr Ile Asp Arg
 1               5

<210> SEQ ID NO 186
<211> LENGTH: 6
<212> TYPE: PRT
<213> ORGANISM: Artificial Sequence
<220> FEATURE:
<223> OTHER INFORMATION: Peptide X Library

<400> SEQUENCE: 186

Ala His Tyr Ile Asp Arg
 1               5

<210> SEQ ID NO 187
<211> LENGTH: 6
<212> TYPE: PRT
```

<213> ORGANISM: Artificial Sequence
<220> FEATURE:
<223> OTHER INFORMATION: Peptide X Library

<400> SEQUENCE: 187

Ile His Ala Tyr Asp Arg
1               5

<210> SEQ ID NO 188
<211> LENGTH: 6
<212> TYPE: PRT
<213> ORGANISM: Artificial Sequence
<220> FEATURE:
<223> OTHER INFORMATION: Peptide X Library

<400> SEQUENCE: 188

His Ile Ala Tyr Asp Arg
1               5

<210> SEQ ID NO 189
<211> LENGTH: 6
<212> TYPE: PRT
<213> ORGANISM: Artificial Sequence
<220> FEATURE:
<223> OTHER INFORMATION: Peptide X Library

<400> SEQUENCE: 189

Ile Ala His Tyr Asp Arg
1               5

<210> SEQ ID NO 190
<211> LENGTH: 6
<212> TYPE: PRT
<213> ORGANISM: Artificial Sequence
<220> FEATURE:
<223> OTHER INFORMATION: Peptide X Library

<400> SEQUENCE: 190

Ala Ile His Tyr Asp Arg
1               5

<210> SEQ ID NO 191
<211> LENGTH: 6
<212> TYPE: PRT
<213> ORGANISM: Artificial Sequence
<220> FEATURE:
<223> OTHER INFORMATION: Peptide X Library

<400> SEQUENCE: 191

His Ala Ile Tyr Asp Arg
1               5

<210> SEQ ID NO 192
<211> LENGTH: 6
<212> TYPE: PRT
<213> ORGANISM: Artificial Sequence
<220> FEATURE:
<223> OTHER INFORMATION: Peptide X Library

<400> SEQUENCE: 192

Ala His Ile Tyr Asp Arg
1               5

<210> SEQ ID NO 193
<211> LENGTH: 6
<212> TYPE: PRT
<213> ORGANISM: Artificial Sequence

```
<220> FEATURE:
<223> OTHER INFORMATION: Peptide X Library

<400> SEQUENCE: 193

Tyr Ile Asp Ala His Arg
 1               5

<210> SEQ ID NO 194
<211> LENGTH: 6
<212> TYPE: PRT
<213> ORGANISM: Artificial Sequence
<220> FEATURE:
<223> OTHER INFORMATION: Peptide X Library

<400> SEQUENCE: 194

Ile Tyr Asp Ala His Arg
 1               5

<210> SEQ ID NO 195
<211> LENGTH: 6
<212> TYPE: PRT
<213> ORGANISM: Artificial Sequence
<220> FEATURE:
<223> OTHER INFORMATION: Peptide X Library

<400> SEQUENCE: 195

Tyr Asp Ile Ala His Arg
 1               5

<210> SEQ ID NO 196
<211> LENGTH: 6
<212> TYPE: PRT
<213> ORGANISM: Artificial Sequence
<220> FEATURE:
<223> OTHER INFORMATION: Peptide X Library

<400> SEQUENCE: 196

Asp Tyr Ile Ala His Arg
 1               5

<210> SEQ ID NO 197
<211> LENGTH: 6
<212> TYPE: PRT
<213> ORGANISM: Artificial Sequence
<220> FEATURE:
<223> OTHER INFORMATION: Peptide X Library

<400> SEQUENCE: 197

Ile Asp Tyr Ala His Arg
 1               5

<210> SEQ ID NO 198
<211> LENGTH: 6
<212> TYPE: PRT
<213> ORGANISM: Artificial Sequence
<220> FEATURE:
<223> OTHER INFORMATION: Peptide X Library

<400> SEQUENCE: 198

Asp Ile Tyr Ala His Arg
 1               5

<210> SEQ ID NO 199
<211> LENGTH: 6
<212> TYPE: PRT
<213> ORGANISM: Artificial Sequence
<220> FEATURE:
```

<223> OTHER INFORMATION: Peptide X Library

<400> SEQUENCE: 199

Tyr Ile Ala Asp His Arg
1               5

<210> SEQ ID NO 200
<211> LENGTH: 6
<212> TYPE: PRT
<213> ORGANISM: Artificial Sequence
<220> FEATURE:
<223> OTHER INFORMATION: Peptide X Library

<400> SEQUENCE: 200

Ile Tyr Ala Asp His Arg
1               5

<210> SEQ ID NO 201
<211> LENGTH: 6
<212> TYPE: PRT
<213> ORGANISM: Artificial Sequence
<220> FEATURE:
<223> OTHER INFORMATION: Peptide X Library

<400> SEQUENCE: 201

Tyr Ala Ile Asp His Arg
1               5

<210> SEQ ID NO 202
<211> LENGTH: 6
<212> TYPE: PRT
<213> ORGANISM: Artificial Sequence
<220> FEATURE:
<223> OTHER INFORMATION: Peptide X Library

<400> SEQUENCE: 202

Ala Tyr Ile Asp His Arg
1               5

<210> SEQ ID NO 203
<211> LENGTH: 6
<212> TYPE: PRT
<213> ORGANISM: Artificial Sequence
<220> FEATURE:
<223> OTHER INFORMATION: Peptide X Library

<400> SEQUENCE: 203

Ile Ala Tyr Asp His Arg
1               5

<210> SEQ ID NO 204
<211> LENGTH: 6
<212> TYPE: PRT
<213> ORGANISM: Artificial Sequence
<220> FEATURE:
<223> OTHER INFORMATION: Peptide X Library

<400> SEQUENCE: 204

Ala Ile Tyr Asp His Arg
1               5

<210> SEQ ID NO 205
<211> LENGTH: 6
<212> TYPE: PRT
<213> ORGANISM: Artificial Sequence
<220> FEATURE:
<223> OTHER INFORMATION: Peptide X Library

```
<400> SEQUENCE: 205

Tyr Asp Ala Ile His Arg
 1               5

<210> SEQ ID NO 206
<211> LENGTH: 6
<212> TYPE: PRT
<213> ORGANISM: Artificial Sequence
<220> FEATURE:
<223> OTHER INFORMATION: Peptide X Library

<400> SEQUENCE: 206

Asp Tyr Ala Ile His Arg
 1               5

<210> SEQ ID NO 207
<211> LENGTH: 6
<212> TYPE: PRT
<213> ORGANISM: Artificial Sequence
<220> FEATURE:
<223> OTHER INFORMATION: Peptide X Library

<400> SEQUENCE: 207

Tyr Ala Asp Ile His Arg
 1               5

<210> SEQ ID NO 208
<211> LENGTH: 6
<212> TYPE: PRT
<213> ORGANISM: Artificial Sequence
<220> FEATURE:
<223> OTHER INFORMATION: Peptide X Library

<400> SEQUENCE: 208

Ala Tyr Asp Ile His Arg
 1               5

<210> SEQ ID NO 209
<211> LENGTH: 6
<212> TYPE: PRT
<213> ORGANISM: Artificial Sequence
<220> FEATURE:
<223> OTHER INFORMATION: Peptide X Library

<400> SEQUENCE: 209

Asp Ala Tyr Ile His Arg
 1               5

<210> SEQ ID NO 210
<211> LENGTH: 6
<212> TYPE: PRT
<213> ORGANISM: Artificial Sequence
<220> FEATURE:
<223> OTHER INFORMATION: Peptide X Library

<400> SEQUENCE: 210

Ala Asp Tyr Ile His Arg
 1               5

<210> SEQ ID NO 211
<211> LENGTH: 6
<212> TYPE: PRT
<213> ORGANISM: Artificial Sequence
<220> FEATURE:
<223> OTHER INFORMATION: Peptide X Library
```

```
<400> SEQUENCE: 211

Ile Asp Ala Tyr His Arg
1               5

<210> SEQ ID NO 212
<211> LENGTH: 6
<212> TYPE: PRT
<213> ORGANISM: Artificial Sequence
<220> FEATURE:
<223> OTHER INFORMATION: Peptide X Library

<400> SEQUENCE: 212

Asp Ile Ala Tyr His Arg
1               5

<210> SEQ ID NO 213
<211> LENGTH: 6
<212> TYPE: PRT
<213> ORGANISM: Artificial Sequence
<220> FEATURE:
<223> OTHER INFORMATION: Peptide X Library
<223> OTHER INFORMATION: Peptide X Library

<400> SEQUENCE: 213

Ile Ala Asp Tyr His Arg
1               5

<210> SEQ ID NO 214
<211> LENGTH: 6
<212> TYPE: PRT
<213> ORGANISM: Artificial Sequence
<220> FEATURE:
<223> OTHER INFORMATION: Peptide X Library

<400> SEQUENCE: 214

Ala Ile Asp Tyr His Arg
1               5

<210> SEQ ID NO 215
<211> LENGTH: 6
<212> TYPE: PRT
<213> ORGANISM: Artificial Sequence
<220> FEATURE:
<223> OTHER INFORMATION: Peptide X Library

<400> SEQUENCE: 215

Asp Ala Ile Tyr His Arg
1               5

<210> SEQ ID NO 216
<211> LENGTH: 6
<212> TYPE: PRT
<213> ORGANISM: Artificial Sequence
<220> FEATURE:
<223> OTHER INFORMATION: Peptide X Library

<400> SEQUENCE: 216

Ala Asp Ile Tyr His Arg
1               5

<210> SEQ ID NO 217
<211> LENGTH: 6
<212> TYPE: PRT
<213> ORGANISM: Artificial Sequence
<220> FEATURE:
<223> OTHER INFORMATION: Peptide X Library
```

```
<400> SEQUENCE: 217

Tyr His Asp Ala Ile Arg
1               5

<210> SEQ ID NO 218
<211> LENGTH: 6
<212> TYPE: PRT
<213> ORGANISM: Artificial Sequence
<220> FEATURE:
<223> OTHER INFORMATION: Peptide X Library

<400> SEQUENCE: 218

His Tyr Asp Ala Ile Arg
1               5

<210> SEQ ID NO 219
<211> LENGTH: 6
<212> TYPE: PRT
<213> ORGANISM: Artificial Sequence
<220> FEATURE:
<223> OTHER INFORMATION: Peptide X Library

<400> SEQUENCE: 219

Tyr Asp His Ala Ile Arg
1               5

<210> SEQ ID NO 220
<211> LENGTH: 6
<212> TYPE: PRT
<213> ORGANISM: Artificial Sequence
<220> FEATURE:
<223> OTHER INFORMATION: Peptide X Library

<400> SEQUENCE: 220

Asp Tyr His Ala Ile Arg
1               5

<210> SEQ ID NO 221
<211> LENGTH: 6
<212> TYPE: PRT
<213> ORGANISM: Artificial Sequence
<220> FEATURE:
<223> OTHER INFORMATION: Peptide X Library

<400> SEQUENCE: 221

His Asp Tyr Ala Ile Arg
1               5

<210> SEQ ID NO 222
<211> LENGTH: 6
<212> TYPE: PRT
<213> ORGANISM: Artificial Sequence
<220> FEATURE:
<223> OTHER INFORMATION: Peptide X Library

<400> SEQUENCE: 222

Asp His Tyr Ala Ile Arg
1               5

<210> SEQ ID NO 223
<211> LENGTH: 6
<212> TYPE: PRT
<213> ORGANISM: Artificial Sequence
<220> FEATURE:
<223> OTHER INFORMATION: Peptide X Library

<400> SEQUENCE: 223
```

Tyr His Ala Asp Ile Arg
1               5

<210> SEQ ID NO 224
<211> LENGTH: 6
<212> TYPE: PRT
<213> ORGANISM: Artificial Sequence
<220> FEATURE:
<223> OTHER INFORMATION: Peptide X Library

<400> SEQUENCE: 224

His Tyr Ala Asp Ile Arg
1               5

<210> SEQ ID NO 225
<211> LENGTH: 6
<212> TYPE: PRT
<213> ORGANISM: Artificial Sequence
<220> FEATURE:
<223> OTHER INFORMATION: Peptide X Library

<400> SEQUENCE: 225

Tyr Ala His Asp Ile Arg
1               5

<210> SEQ ID NO 226
<211> LENGTH: 6
<212> TYPE: PRT
<213> ORGANISM: Artificial Sequence
<220> FEATURE:
<223> OTHER INFORMATION: Peptide X Library

<400> SEQUENCE: 226

Ala Tyr His Asp Ile Arg
1               5

<210> SEQ ID NO 227
<211> LENGTH: 6
<212> TYPE: PRT
<213> ORGANISM: Artificial Sequence
<220> FEATURE:
<223> OTHER INFORMATION: Peptide X Library

<400> SEQUENCE: 227

His Ala Tyr Asp Ile Arg
1               5

<210> SEQ ID NO 228
<211> LENGTH: 6
<212> TYPE: PRT
<213> ORGANISM: Artificial Sequence
<220> FEATURE:
<223> OTHER INFORMATION: Peptide X Library

<400> SEQUENCE: 228

Ala His Tyr Asp Ile Arg
1               5

<210> SEQ ID NO 229
<211> LENGTH: 6
<212> TYPE: PRT
<213> ORGANISM: Artificial Sequence
<220> FEATURE:
<223> OTHER INFORMATION: Peptide X Library

<400> SEQUENCE: 229

Tyr Asp Ala His Ile Arg
1               5

<210> SEQ ID NO 230
<211> LENGTH: 6
<212> TYPE: PRT
<213> ORGANISM: Artificial Sequence
<220> FEATURE:
<223> OTHER INFORMATION: Peptide X Library

<400> SEQUENCE: 230

Asp Tyr Ala His Ile Arg
1               5

<210> SEQ ID NO 231
<211> LENGTH: 6
<212> TYPE: PRT
<213> ORGANISM: Artificial Sequence
<220> FEATURE:
<223> OTHER INFORMATION: Peptide X Library

<400> SEQUENCE: 231

Tyr Ala Asp His Ile Arg
1               5

<210> SEQ ID NO 232
<211> LENGTH: 6
<212> TYPE: PRT
<213> ORGANISM: Artificial Sequence
<220> FEATURE:
<223> OTHER INFORMATION: Peptide X Library

<400> SEQUENCE: 232

Ala Tyr Asp His Ile Arg
1               5

<210> SEQ ID NO 233
<211> LENGTH: 6
<212> TYPE: PRT
<213> ORGANISM: Artificial Sequence
<220> FEATURE:
<223> OTHER INFORMATION: Peptide X Library

<400> SEQUENCE: 233

Asp Ala Tyr His Ile Arg
1               5

<210> SEQ ID NO 234
<211> LENGTH: 6
<212> TYPE: PRT
<213> ORGANISM: Artificial Sequence
<220> FEATURE:
<223> OTHER INFORMATION: Peptide X Library

<400> SEQUENCE: 234

Ala Asp Tyr His Ile Arg
1               5

<210> SEQ ID NO 235
<211> LENGTH: 6
<212> TYPE: PRT
<213> ORGANISM: Artificial Sequence
<220> FEATURE:
<223> OTHER INFORMATION: Peptide X Library

<400> SEQUENCE: 235

His Asp Ala Tyr Ile Arg

```
1               5

<210> SEQ ID NO 236
<211> LENGTH: 6
<212> TYPE: PRT
<213> ORGANISM: Artificial Sequence
<220> FEATURE:
<223> OTHER INFORMATION: Peptide X Library

<400> SEQUENCE: 236

Asp His Ala Tyr Ile Arg
1               5

<210> SEQ ID NO 237
<211> LENGTH: 6
<212> TYPE: PRT
<213> ORGANISM: Artificial Sequence
<220> FEATURE:
<223> OTHER INFORMATION: Peptide X Library

<400> SEQUENCE: 237

His Ala Asp Tyr Ile Arg
1               5

<210> SEQ ID NO 238
<211> LENGTH: 6
<212> TYPE: PRT
<213> ORGANISM: Artificial Sequence
<220> FEATURE:
<223> OTHER INFORMATION: Peptide X Library

<400> SEQUENCE: 238

Ala His Asp Tyr Ile Arg
1               5

<210> SEQ ID NO 239
<211> LENGTH: 6
<212> TYPE: PRT
<213> ORGANISM: Artificial Sequence
<220> FEATURE:
<223> OTHER INFORMATION: Peptide X Library

<400> SEQUENCE: 239

Asp Ala His Tyr Ile Arg
1               5

<210> SEQ ID NO 240
<211> LENGTH: 6
<212> TYPE: PRT
<213> ORGANISM: Artificial Sequence
<220> FEATURE:
<223> OTHER INFORMATION: Peptide X Library

<400> SEQUENCE: 240

Ala Asp His Tyr Ile Arg
1               5

<210> SEQ ID NO 241
<211> LENGTH: 6
<212> TYPE: PRT
<213> ORGANISM: Artificial Sequence
<220> FEATURE:
<223> OTHER INFORMATION: Peptide X Library

<400> SEQUENCE: 241

Ile His Asp Ala Tyr Arg
1               5
```

```
<210> SEQ ID NO 242
<211> LENGTH: 6
<212> TYPE: PRT
<213> ORGANISM: Artificial Sequence
<220> FEATURE:
<223> OTHER INFORMATION: Peptide X Library

<400> SEQUENCE: 242

His Ile Asp Ala Tyr Arg
 1               5

<210> SEQ ID NO 243
<211> LENGTH: 6
<212> TYPE: PRT
<213> ORGANISM: Artificial Sequence
<220> FEATURE:
<223> OTHER INFORMATION: Peptide X Library

<400> SEQUENCE: 243

Ile Asp His Ala Tyr Arg
 1               5

<210> SEQ ID NO 244
<211> LENGTH: 6
<212> TYPE: PRT
<213> ORGANISM: Artificial Sequence
<220> FEATURE:
<223> OTHER INFORMATION: Peptide X Library

<400> SEQUENCE: 244

Asp Ile His Ala Tyr Arg
 1               5

<210> SEQ ID NO 245
<211> LENGTH: 6
<212> TYPE: PRT
<213> ORGANISM: Artificial Sequence
<220> FEATURE:
<223> OTHER INFORMATION: Peptide X Library

<400> SEQUENCE: 245

His Asp Ile Ala Tyr Arg
 1               5

<210> SEQ ID NO 246
<211> LENGTH: 6
<212> TYPE: PRT
<213> ORGANISM: Artificial Sequence
<220> FEATURE:
<223> OTHER INFORMATION: Peptide X Library

<400> SEQUENCE: 246

Asp His Ile Ala Tyr Arg
 1               5

<210> SEQ ID NO 247
<211> LENGTH: 6
<212> TYPE: PRT
<213> ORGANISM: Artificial Sequence
<220> FEATURE:
<223> OTHER INFORMATION: Peptide X Library

<400> SEQUENCE: 247

Ile His Ala Asp Tyr Arg
 1               5
```

```
<210> SEQ ID NO 248
<211> LENGTH: 6
<212> TYPE: PRT
<213> ORGANISM: Artificial Sequence
<220> FEATURE:
<223> OTHER INFORMATION: Peptide X Library

<400> SEQUENCE: 248

His Ile Ala Asp Tyr Arg
 1               5

<210> SEQ ID NO 249
<211> LENGTH: 6
<212> TYPE: PRT
<213> ORGANISM: Artificial Sequence
<220> FEATURE:
<223> OTHER INFORMATION: Peptide X Library

<400> SEQUENCE: 249

Ile Ala His Asp Tyr Arg
 1               5

<210> SEQ ID NO 250
<211> LENGTH: 6
<212> TYPE: PRT
<213> ORGANISM: Artificial Sequence
<220> FEATURE:
<223> OTHER INFORMATION: Peptide X Library

<400> SEQUENCE: 250

Ala Ile His Asp Tyr Arg
 1               5

<210> SEQ ID NO 251
<211> LENGTH: 6
<212> TYPE: PRT
<213> ORGANISM: Artificial Sequence
<220> FEATURE:
<223> OTHER INFORMATION: Peptide X Library

<400> SEQUENCE: 251

His Ala Ile Asp Tyr Arg
 1               5

<210> SEQ ID NO 252
<211> LENGTH: 6
<212> TYPE: PRT
<213> ORGANISM: Artificial Sequence
<220> FEATURE:
<223> OTHER INFORMATION: Peptide X Library

<400> SEQUENCE: 252

Ala His Ile Asp Tyr Arg
 1               5

<210> SEQ ID NO 253
<211> LENGTH: 6
<212> TYPE: PRT
<213> ORGANISM: Artificial Sequence
<220> FEATURE:
<223> OTHER INFORMATION: Peptide X Library

<400> SEQUENCE: 253

Ile Asp Ala His Tyr Arg
 1               5
```

```
<210> SEQ ID NO 254
<211> LENGTH: 6
<212> TYPE: PRT
<213> ORGANISM: Artificial Sequence
<220> FEATURE:
<223> OTHER INFORMATION: Peptide X Library

<400> SEQUENCE: 254

Asp Ile Ala His Tyr Arg
 1               5

<210> SEQ ID NO 255
<211> LENGTH: 6
<212> TYPE: PRT
<213> ORGANISM: Artificial Sequence
<220> FEATURE:
<223> OTHER INFORMATION: Peptide X Library

<400> SEQUENCE: 255

Ile Ala Asp His Tyr Arg
 1               5

<210> SEQ ID NO 256
<211> LENGTH: 6
<212> TYPE: PRT
<213> ORGANISM: Artificial Sequence
<220> FEATURE:
<223> OTHER INFORMATION: Peptide X Library

<400> SEQUENCE: 256

Ala Ile Asp His Tyr Arg
 1               5

<210> SEQ ID NO 257
<211> LENGTH: 6
<212> TYPE: PRT
<213> ORGANISM: Artificial Sequence
<220> FEATURE:
<223> OTHER INFORMATION: Peptide X Library

<400> SEQUENCE: 257

Asp Ala Ile His Tyr Arg
 1               5

<210> SEQ ID NO 258
<211> LENGTH: 6
<212> TYPE: PRT
<213> ORGANISM: Artificial Sequence
<220> FEATURE:
<223> OTHER INFORMATION: Peptide X Library

<400> SEQUENCE: 258

Ala Asp Ile His Tyr Arg
 1               5

<210> SEQ ID NO 259
<211> LENGTH: 6
<212> TYPE: PRT
<213> ORGANISM: Artificial Sequence
<220> FEATURE:
<223> OTHER INFORMATION: Peptide X Library

<400> SEQUENCE: 259

His Asp Ala Ile Tyr Arg
 1               5

<210> SEQ ID NO 260
```

```
<211> LENGTH: 6
<212> TYPE: PRT
<213> ORGANISM: Artificial Sequence
<220> FEATURE:
<223> OTHER INFORMATION: Peptide X Library

<400> SEQUENCE: 260

His Ala Asp Ile Tyr Arg
 1               5

<210> SEQ ID NO 261
<211> LENGTH: 6
<212> TYPE: PRT
<213> ORGANISM: Artificial Sequence
<220> FEATURE:
<223> OTHER INFORMATION: Peptide X Library

<400> SEQUENCE: 261

His Ala Asp Ile Tyr Arg
 1               5

<210> SEQ ID NO 262
<211> LENGTH: 6
<212> TYPE: PRT
<213> ORGANISM: Artificial Sequence
<220> FEATURE:
<223> OTHER INFORMATION: Peptide X Library

<400> SEQUENCE: 262

Ala His Asp Ile Tyr Arg
 1               5

<210> SEQ ID NO 263
<211> LENGTH: 6
<212> TYPE: PRT
<213> ORGANISM: Artificial Sequence
<220> FEATURE:
<223> OTHER INFORMATION: Peptide X Library

<400> SEQUENCE: 263

Asp Ala His Ile Tyr Arg
 1               5

<210> SEQ ID NO 264
<211> LENGTH: 6
<212> TYPE: PRT
<213> ORGANISM: Artificial Sequence
<220> FEATURE:
<223> OTHER INFORMATION: Peptide X Library

<400> SEQUENCE: 264

Ala Asp His Ile Tyr Arg
 1               5

<210> SEQ ID NO 265
<211> LENGTH: 7
<212> TYPE: PRT
<213> ORGANISM: Artificial Sequence
<220> FEATURE:
<223> OTHER INFORMATION: Peptide Y Library

<400> SEQUENCE: 265

Tyr Gly Gly Phe Ile Arg Arg
 1               5

<210> SEQ ID NO 266
<211> LENGTH: 7
```

```
<212> TYPE: PRT
<213> ORGANISM: Artificial Sequence
<220> FEATURE:
<223> OTHER INFORMATION: Peptide Y Library

<400> SEQUENCE: 266

Tyr Gly Gly Arg Ile Phe Arg
1               5

<210> SEQ ID NO 267
<211> LENGTH: 8
<212> TYPE: PRT
<213> ORGANISM: Artificial Sequence
<220> FEATURE:
<223> OTHER INFORMATION: Peptide Y Library

<400> SEQUENCE: 267

Tyr Gly Gly Phe Ile Gly Val Arg
1               5

<210> SEQ ID NO 268
<211> LENGTH: 8
<212> TYPE: PRT
<213> ORGANISM: Artificial Sequence
<220> FEATURE:
<223> OTHER INFORMATION: Peptide Y Library

<400> SEQUENCE: 268

Tyr Gly Gly Phe Ile Val Gly Arg
1               5

<210> SEQ ID NO 269
<211> LENGTH: 7
<212> TYPE: PRT
<213> ORGANISM: Artificial Sequence
<220> FEATURE:
<223> OTHER INFORMATION: Peptide Y Library

<400> SEQUENCE: 269

Tyr Gly Gly Arg Phe Ile Arg
1               5

<210> SEQ ID NO 270
<211> LENGTH: 7
<212> TYPE: PRT
<213> ORGANISM: Artificial Sequence
<220> FEATURE:
<223> OTHER INFORMATION: Peptide Y Library

<400> SEQUENCE: 270

Tyr Gly Val Asn Ile Phe Arg
1               5

<210> SEQ ID NO 271
<211> LENGTH: 7
<212> TYPE: PRT
<213> ORGANISM: Artificial Sequence
<220> FEATURE:
<223> OTHER INFORMATION: Peptide Y Library

<400> SEQUENCE: 271

Tyr Gly Val Asn Phe Ile Arg
1               5

<210> SEQ ID NO 272
<211> LENGTH: 6
<212> TYPE: PRT
```

```
<213> ORGANISM: Artificial Sequence
<220> FEATURE:
<223> OTHER INFORMATION: Peptide Y Library

<400> SEQUENCE: 272

Tyr Gly Gly Gly Val Ile
1               5

<210> SEQ ID NO 273
<211> LENGTH: 7
<212> TYPE: PRT
<213> ORGANISM: Artificial Sequence
<220> FEATURE:
<223> OTHER INFORMATION: Peptide Y Library

<400> SEQUENCE: 273

Tyr Gly Gly Ile Phe Arg Arg
1               5

<210> SEQ ID NO 274
<211> LENGTH: 8
<212> TYPE: PRT
<213> ORGANISM: Artificial Sequence
<220> FEATURE:
<223> OTHER INFORMATION: Peptide Y Library

<400> SEQUENCE: 274

Tyr Gly Gly Val Gly Ile Phe Arg
1               5

<210> SEQ ID NO 275
<211> LENGTH: 4
<212> TYPE: PRT
<213> ORGANISM: Artificial Sequence
<220> FEATURE:
<223> OTHER INFORMATION: Peptide Z Library

<400> SEQUENCE: 275

Pro Thr Ile Trp
1

<210> SEQ ID NO 276
<211> LENGTH: 5
<212> TYPE: PRT
<213> ORGANISM: Artificial Sequence
<220> FEATURE:
<223> OTHER INFORMATION: Peptide Z Library

<400> SEQUENCE: 276

Phe Arg Pro Ser Gly
1               5

<210> SEQ ID NO 277
<211> LENGTH: 4
<212> TYPE: PRT
<213> ORGANISM: Artificial Sequence
<220> FEATURE:
<223> OTHER INFORMATION: Peptide Z Library

<400> SEQUENCE: 277

Val Val Ile Trp
1

<210> SEQ ID NO 278
<211> LENGTH: 4
<212> TYPE: PRT
<213> ORGANISM: Artificial Sequence
```

```
<220> FEATURE:
<223> OTHER INFORMATION: Peptide Z Library

<400> SEQUENCE: 278

Gly Gln Arg Arg
 1

<210> SEQ ID NO 279
<211> LENGTH: 4
<212> TYPE: PRT
<213> ORGANISM: Artificial Sequence
<220> FEATURE:
<223> OTHER INFORMATION: Peptide Z Library

<400> SEQUENCE: 279

Ala Asn Arg Arg
 1

<210> SEQ ID NO 280
<211> LENGTH: 4
<212> TYPE: PRT
<213> ORGANISM: Artificial Sequence
<220> FEATURE:
<223> OTHER INFORMATION: Peptide Z Library

<400> SEQUENCE: 280

Gly Ala Arg Arg
 1

<210> SEQ ID NO 281
<211> LENGTH: 4
<212> TYPE: PRT
<213> ORGANISM: Artificial Sequence
<220> FEATURE:
<223> OTHER INFORMATION: Peptide Z Library

<400> SEQUENCE: 281

Pro Pro Phe Arg
 1

<210> SEQ ID NO 282
<211> LENGTH: 4
<212> TYPE: PRT
<213> ORGANISM: Artificial Sequence
<220> FEATURE:
<223> OTHER INFORMATION: Peptide Z Library

<400> SEQUENCE: 282

Pro Ile Met Arg
 1

<210> SEQ ID NO 283
<211> LENGTH: 4
<212> TYPE: PRT
<213> ORGANISM: Artificial Sequence
<220> FEATURE:
<223> OTHER INFORMATION: Peptide Z Library

<400> SEQUENCE: 283

Val Ile Glu Arg
 1

<210> SEQ ID NO 284
<211> LENGTH: 4
<212> TYPE: PRT
<213> ORGANISM: Artificial Sequence
<220> FEATURE:
```

<223> OTHER INFORMATION: Peptide Z Library

<400> SEQUENCE: 284

Val Asn Gln Arg
1

<210> SEQ ID NO 285
<211> LENGTH: 5
<212> TYPE: PRT
<213> ORGANISM: Artificial Sequence
<220> FEATURE:
<223> OTHER INFORMATION: Peptide Z Library

<400> SEQUENCE: 285

Cys Gly Val Gln Arg
1               5

<210> SEQ ID NO 286
<211> LENGTH: 5
<212> TYPE: PRT
<213> ORGANISM: Artificial Sequence
<220> FEATURE:
<223> OTHER INFORMATION: Peptide Z Library

<400> SEQUENCE: 286

Ala Ala Ala Gln Arg
1               5

<210> SEQ ID NO 287
<211> LENGTH: 4
<212> TYPE: PRT
<213> ORGANISM: Artificial Sequence
<220> FEATURE:
<223> OTHER INFORMATION: Peptide Z Library

<400> SEQUENCE: 287

Ile Ile Asp Arg
1

<210> SEQ ID NO 288
<211> LENGTH: 3
<212> TYPE: PRT
<213> ORGANISM: Artificial Sequence
<220> FEATURE:
<223> OTHER INFORMATION: Peptide Z Library

<400> SEQUENCE: 288

Ile Asn Met
1

<210> SEQ ID NO 289
<211> LENGTH: 5
<212> TYPE: PRT
<213> ORGANISM: Artificial Sequence
<220> FEATURE:
<223> OTHER INFORMATION: Peptide Z Library

<400> SEQUENCE: 289

Gly Gly Ile Asn Arg
1               5

<210> SEQ ID NO 290
<211> LENGTH: 5
<212> TYPE: PRT
<213> ORGANISM: Artificial Sequence
<220> FEATURE:
<223> OTHER INFORMATION: Peptide Z Library

```
<400> SEQUENCE: 290

Gly Ala Val Asn Arg
 1               5

<210> SEQ ID NO 291
<211> LENGTH: 6
<212> TYPE: PRT
<213> ORGANISM: Artificial Sequence
<220> FEATURE:
<223> OTHER INFORMATION: Peptide Z Library

<400> SEQUENCE: 291

Gly Gly Gly Gly Ile Arg
 1               5

<210> SEQ ID NO 292
<211> LENGTH: 6
<212> TYPE: PRT
<213> ORGANISM: Artificial Sequence
<220> FEATURE:
<223> OTHER INFORMATION: Peptide Z Library

<400> SEQUENCE: 292

Gly Gly Gly Ala Val Arg
 1               5

<210> SEQ ID NO 293
<211> LENGTH: 6
<212> TYPE: PRT
<213> ORGANISM: Artificial Sequence
<220> FEATURE:
<223> OTHER INFORMATION: Peptide Z Library

<400> SEQUENCE: 293

Gly Ala Ala Ala Ala Arg
 1               5

<210> SEQ ID NO 294
<211> LENGTH: 5
<212> TYPE: PRT
<213> ORGANISM: Artificial Sequence
<220> FEATURE:
<223> OTHER INFORMATION: Peptide Z Library

<400> SEQUENCE: 294

Gly Pro Pro Val Phe
 1               5

<210> SEQ ID NO 295
<211> LENGTH: 5
<212> TYPE: PRT
<213> ORGANISM: Artificial Sequence
<220> FEATURE:
<223> OTHER INFORMATION: Peptide Z Library

<400> SEQUENCE: 295

Gly Pro Val Ile Met
 1               5

<210> SEQ ID NO 296
<211> LENGTH: 5
<212> TYPE: PRT
<213> ORGANISM: Artificial Sequence
<220> FEATURE:
<223> OTHER INFORMATION: Peptide Z Library
```

```
<400> SEQUENCE: 296

Ala Pro Val Val Met
1               5

<210> SEQ ID NO 297
<211> LENGTH: 5
<212> TYPE: PRT
<213> ORGANISM: Artificial Sequence
<220> FEATURE:
<223> OTHER INFORMATION: Peptide Z Library

<400> SEQUENCE: 297

Ala Ala Ile Ile Glu
1               5

<210> SEQ ID NO 298
<211> LENGTH: 5
<212> TYPE: PRT
<213> ORGANISM: Artificial Sequence
<220> FEATURE:
<223> OTHER INFORMATION: Peptide Z Library

<400> SEQUENCE: 298

Gly Pro Thr Ile Glu
1               5

<210> SEQ ID NO 299
<211> LENGTH: 5
<212> TYPE: PRT
<213> ORGANISM: Artificial Sequence
<220> FEATURE:
<223> OTHER INFORMATION: Peptide Z Library

<400> SEQUENCE: 299

Gly Val Val Ile Glu
1               5

<210> SEQ ID NO 300
<211> LENGTH: 5
<212> TYPE: PRT
<213> ORGANISM: Artificial Sequence
<220> FEATURE:
<223> OTHER INFORMATION: Peptide Z Library

<400> SEQUENCE: 300

Ala Ser Pro Ile Glu
1               5

<210> SEQ ID NO 301
<211> LENGTH: 5
<212> TYPE: PRT
<213> ORGANISM: Artificial Sequence
<220> FEATURE:
<223> OTHER INFORMATION: Peptide Z Library

<400> SEQUENCE: 301

Ala Pro Val Thr Glu
1               5

<210> SEQ ID NO 302
<211> LENGTH: 5
<212> TYPE: PRT
<213> ORGANISM: Artificial Sequence
<220> FEATURE:
<223> OTHER INFORMATION: Peptide Z Library

<400> SEQUENCE: 302
```

Ala Val Val Val Glu
1               5

<210> SEQ ID NO 303
<211> LENGTH: 5
<212> TYPE: PRT
<213> ORGANISM: Artificial Sequence
<220> FEATURE:
<223> OTHER INFORMATION: Peptide Z Library

<400> SEQUENCE: 303

Gly Ser Pro Lys Lys
1               5

<210> SEQ ID NO 304
<211> LENGTH: 4
<212> TYPE: PRT
<213> ORGANISM: Artificial Sequence
<220> FEATURE:
<223> OTHER INFORMATION: Peptide Z Library

<400> SEQUENCE: 304

Ile Gln Gln Lys
1

<210> SEQ ID NO 305
<211> LENGTH: 5
<212> TYPE: PRT
<213> ORGANISM: Artificial Sequence
<220> FEATURE:
<223> OTHER INFORMATION: Peptide Z Library

<400> SEQUENCE: 305

Gly Ala Ile Gln Lys
1               5

<210> SEQ ID NO 306
<211> LENGTH: 5
<212> TYPE: PRT
<213> ORGANISM: Artificial Sequence
<220> FEATURE:
<223> OTHER INFORMATION: Peptide Z Library

<400> SEQUENCE: 306

Ala Ala Val Gln Lys
1               5

<210> SEQ ID NO 307
<211> LENGTH: 5
<212> TYPE: PRT
<213> ORGANISM: Artificial Sequence
<220> FEATURE:
<223> OTHER INFORMATION: Peptide Z Library

<400> SEQUENCE: 307

Gly Ser Pro Gln Lys
1               5

<210> SEQ ID NO 308
<211> LENGTH: 5
<212> TYPE: PRT
<213> ORGANISM: Artificial Sequence
<220> FEATURE:
<223> OTHER INFORMATION: Peptide Z Library

<400> SEQUENCE: 308

```
Ala Ala Ile Asn Tyr
 1               5

<210> SEQ ID NO 309
<211> LENGTH: 5
<212> TYPE: PRT
<213> ORGANISM: Artificial Sequence
<220> FEATURE:
<223> OTHER INFORMATION: Peptide Z Library

<400> SEQUENCE: 309

Gly Pro Thr Asn Lys
 1               5

<210> SEQ ID NO 310
<211> LENGTH: 5
<212> TYPE: PRT
<213> ORGANISM: Artificial Sequence
<220> FEATURE:
<223> OTHER INFORMATION: Peptide Z Library

<400> SEQUENCE: 310

Gly Val Val Asn Lys
 1               5

<210> SEQ ID NO 311
<211> LENGTH: 5
<212> TYPE: PRT
<213> ORGANISM: Artificial Sequence
<220> FEATURE:
<223> OTHER INFORMATION: Peptide Z Library

<400> SEQUENCE: 311

Ala Ser Pro Asn Lys
 1               5

<210> SEQ ID NO 312
<211> LENGTH: 6
<212> TYPE: PRT
<213> ORGANISM: Artificial Sequence
<220> FEATURE:
<223> OTHER INFORMATION: Peptide Z Library

<400> SEQUENCE: 312

Gly Gly Ala Ala Ile Lys
 1               5

<210> SEQ ID NO 313
<211> LENGTH: 6
<212> TYPE: PRT
<213> ORGANISM: Artificial Sequence
<220> FEATURE:
<223> OTHER INFORMATION: Peptide Z Library

<400> SEQUENCE: 313

Gly Gly Gly Pro Thr Lys
 1               5

<210> SEQ ID NO 314
<211> LENGTH: 6
<212> TYPE: PRT
<213> ORGANISM: Artificial Sequence
<220> FEATURE:
<223> OTHER INFORMATION: Peptide Z Library

<400> SEQUENCE: 314

Gly Gly Gly Val Val Lys
```

```
                              1               5

<210> SEQ ID NO 315
<211> LENGTH: 6
<212> TYPE: PRT
<213> ORGANISM: Artificial Sequence
<220> FEATURE:
<223> OTHER INFORMATION: Peptide Z Library

<400> SEQUENCE: 315

Gly Ala Ala Ala Val Lys
 1               5

<210> SEQ ID NO 316
<211> LENGTH: 6
<212> TYPE: PRT
<213> ORGANISM: Artificial Sequence
<220> FEATURE:
<223> OTHER INFORMATION: Peptide Z Library

<400> SEQUENCE: 316

Gly Gly Ala Ser Pro Lys
 1               5

<210> SEQ ID NO 317
<211> LENGTH: 4
<212> TYPE: PRT
<213> ORGANISM: Artificial Sequence
<220> FEATURE:
<223> OTHER INFORMATION: Peptide Z Library

<400> SEQUENCE: 317

Ile Gln Gln Gln
 1

<210> SEQ ID NO 318
<211> LENGTH: 5
<212> TYPE: PRT
<213> ORGANISM: Artificial Sequence
<220> FEATURE:
<223> OTHER INFORMATION: Peptide Z Library

<400> SEQUENCE: 318

Gly Ala Ile Gln Gln
 1               5

<210> SEQ ID NO 319
<211> LENGTH: 5
<212> TYPE: PRT
<213> ORGANISM: Artificial Sequence
<220> FEATURE:
<223> OTHER INFORMATION: Peptide Z Library

<400> SEQUENCE: 319

Ala Ala Val Gln Gln
 1               5

<210> SEQ ID NO 320
<211> LENGTH: 5
<212> TYPE: PRT
<213> ORGANISM: Artificial Sequence
<220> FEATURE:
<223> OTHER INFORMATION: Peptide Z Library

<400> SEQUENCE: 320

Ala Ala Ile Asn Gln
 1               5
```

-continued

```
<210> SEQ ID NO 321
<211> LENGTH: 5
<212> TYPE: PRT
<213> ORGANISM: Artificial Sequence
<220> FEATURE:
<223> OTHER INFORMATION: Peptide Z Library

<400> SEQUENCE: 321

Gly Val Val Asn Gln
 1               5

<210> SEQ ID NO 322
<211> LENGTH: 6
<212> TYPE: PRT
<213> ORGANISM: Artificial Sequence
<220> FEATURE:
<223> OTHER INFORMATION: Peptide Z Library

<400> SEQUENCE: 322

Gly Gly Ala Ala Ile Gln
 1               5

<210> SEQ ID NO 323
<211> LENGTH: 6
<212> TYPE: PRT
<213> ORGANISM: Artificial Sequence
<220> FEATURE:
<223> OTHER INFORMATION: Peptide Z Library

<400> SEQUENCE: 323

Gly Gly Gly Val Val Gln
 1               5

<210> SEQ ID NO 324
<211> LENGTH: 5
<212> TYPE: PRT
<213> ORGANISM: Artificial Sequence
<220> FEATURE:
<223> OTHER INFORMATION: Peptide Z Library

<400> SEQUENCE: 324

Ala Ala Ala Val Gln
 1               5

<210> SEQ ID NO 325
<211> LENGTH: 5
<212> TYPE: PRT
<213> ORGANISM: Artificial Sequence
<220> FEATURE:
<223> OTHER INFORMATION: Peptide Z Library

<400> SEQUENCE: 325

Gly Val Ile Ile Asp
 1               5

<210> SEQ ID NO 326
<211> LENGTH: 5
<212> TYPE: PRT
<213> ORGANISM: Artificial Sequence
<220> FEATURE:
<223> OTHER INFORMATION: Peptide Z Library

<400> SEQUENCE: 326

Ala Pro Thr Ile Asp
 1               5
```

```
<210> SEQ ID NO 327
<211> LENGTH: 5
<212> TYPE: PRT
<213> ORGANISM: Artificial Sequence
<220> FEATURE:
<223> OTHER INFORMATION: Peptide Z Library

<400> SEQUENCE: 327

Ala Val Val Ile Asp
 1               5

<210> SEQ ID NO 328
<211> LENGTH: 5
<212> TYPE: PRT
<213> ORGANISM: Artificial Sequence
<220> FEATURE:
<223> OTHER INFORMATION: Peptide Z Library

<400> SEQUENCE: 328

Ser Pro Val Val Asp
 1               5

<210> SEQ ID NO 329
<211> LENGTH: 5
<212> TYPE: PRT
<213> ORGANISM: Artificial Sequence
<220> FEATURE:
<223> OTHER INFORMATION: Peptide Z Library

<400> SEQUENCE: 329

Gly Val Ile Asn Asn
 1               5

<210> SEQ ID NO 330
<211> LENGTH: 5
<212> TYPE: PRT
<213> ORGANISM: Artificial Sequence
<220> FEATURE:
<223> OTHER INFORMATION: Peptide Z Library

<400> SEQUENCE: 330

Ala Val Val Asn Asn
 1               5

<210> SEQ ID NO 331
<211> LENGTH: 6
<212> TYPE: PRT
<213> ORGANISM: Artificial Sequence
<220> FEATURE:
<223> OTHER INFORMATION: Peptide Z Library

<400> SEQUENCE: 331

Gly Gly Gly Val Ile Asn
 1               5

<210> SEQ ID NO 332
<211> LENGTH: 6
<212> TYPE: PRT
<213> ORGANISM: Artificial Sequence
<220> FEATURE:
<223> OTHER INFORMATION: Peptide Z Library

<400> SEQUENCE: 332

Gly Ala Ala Ala Ile Asn
 1               5
```

```
<210> SEQ ID NO 333
<211> LENGTH: 6
<212> TYPE: PRT
<213> ORGANISM: Artificial Sequence
<220> FEATURE:
<223> OTHER INFORMATION: Peptide Z Library

<400> SEQUENCE: 333

Gly Gly Ala Val Val Asn
 1               5

<210> SEQ ID NO 334
<211> LENGTH: 6
<212> TYPE: PRT
<213> ORGANISM: Artificial Sequence
<220> FEATURE:
<223> OTHER INFORMATION: Peptide Z Library

<400> SEQUENCE: 334

Ala Ala Ala Ala Val Asn
 1               5

<210> SEQ ID NO 335
<211> LENGTH: 5
<212> TYPE: PRT
<213> ORGANISM: Artificial Sequence
<220> FEATURE:
<223> OTHER INFORMATION: Peptide Z Library

<400> SEQUENCE: 335

Ser Ser Pro Ile Ile
 1               5

<210> SEQ ID NO 336
<211> LENGTH: 5
<212> TYPE: PRT
<213> ORGANISM: Artificial Sequence
<220> FEATURE:
<223> OTHER INFORMATION: Peptide Z Library

<400> SEQUENCE: 336

Ser Pro Val Thr Ile
 1               5

<210> SEQ ID NO 337
<211> LENGTH: 7
<212> TYPE: PRT
<213> ORGANISM: Artificial Sequence
<220> FEATURE:
<223> OTHER INFORMATION: Peptide Z Library

<400> SEQUENCE: 337

Gly Gly Gly Gly Gly Val Ile
 1               5

<210> SEQ ID NO 338
<211> LENGTH: 8
<212> TYPE: PRT
<213> ORGANISM: Artificial Sequence
<220> FEATURE:
<223> OTHER INFORMATION: Peptide Z Library

<400> SEQUENCE: 338

Gly Gly Gly Ala Ala Ala Ala Ile
 1               5

<210> SEQ ID NO 339
```

```
<211> LENGTH: 5
<212> TYPE: PRT
<213> ORGANISM: Artificial Sequence
<220> FEATURE:
<223> OTHER INFORMATION: Peptide Z Library

<400> SEQUENCE: 339

Pro Pro Thr Thr Thr
 1               5

<210> SEQ ID NO 340
<211> LENGTH: 5
<212> TYPE: PRT
<213> ORGANISM: Artificial Sequence
<220> FEATURE:
<223> OTHER INFORMATION: Peptide Z Library

<400> SEQUENCE: 340

Pro Val Val Thr Thr
 1               5

<210> SEQ ID NO 341
<211> LENGTH: 7
<212> TYPE: PRT
<213> ORGANISM: Artificial Sequence
<220> FEATURE:
<223> OTHER INFORMATION: Peptide Z Library

<400> SEQUENCE: 341

Gly Gly Gly Gly Ala Val Val
 1               5

<210> SEQ ID NO 342
<211> LENGTH: 7
<212> TYPE: PRT
<213> ORGANISM: Artificial Sequence
<220> FEATURE:
<223> OTHER INFORMATION: Peptide Z Library

<400> SEQUENCE: 342

Gly Gly Ala Ala Ala Ala Val
 1               5

<210> SEQ ID NO 343
<211> LENGTH: 7
<212> TYPE: PRT
<213> ORGANISM: Artificial Sequence
<220> FEATURE:
<223> OTHER INFORMATION: Peptide Z Library

<400> SEQUENCE: 343

Ala Ala Ala Ala Ala Ala Ala
 1               5

<210> SEQ ID NO 344
<211> LENGTH: 9
<212> TYPE: PRT
<213> ORGANISM: Artificial Sequence
<220> FEATURE:
<223> OTHER INFORMATION: Top Ranked Peptide Library

<400> SEQUENCE: 344

Arg Pro Pro Gly Phe Ser Pro Phe Arg
 1               5

<210> SEQ ID NO 345
<211> LENGTH: 9
```

```
<212> TYPE: PRT
<213> ORGANISM: Artificial Sequence
<220> FEATURE:
<223> OTHER INFORMATION: Top Ranked Peptide Library

<400> SEQUENCE: 345

Arg Pro Pro Gly Phe Pro Ser Phe Arg
 1               5

<210> SEQ ID NO 346
<211> LENGTH: 9
<212> TYPE: PRT
<213> ORGANISM: Artificial Sequence
<220> FEATURE:
<223> OTHER INFORMATION: Top Ranked Peptide Library

<400> SEQUENCE: 346

Arg Pro Pro Phe Gly Pro Ser Phe Arg
 1               5

<210> SEQ ID NO 347
<211> LENGTH: 9
<212> TYPE: PRT
<213> ORGANISM: Artificial Sequence
<220> FEATURE:
<223> OTHER INFORMATION: Top Ranked Peptide Library

<400> SEQUENCE: 347

Arg Pro Pro Gly Phe Phe Pro Ser Arg
 1               5

<210> SEQ ID NO 348
<211> LENGTH: 9
<212> TYPE: PRT
<213> ORGANISM: Artificial Sequence
<220> FEATURE:
<223> OTHER INFORMATION: Top Ranked Peptide Library

<400> SEQUENCE: 348

Arg Pro Pro Gly Phe Phe Ser Pro Arg
 1               5

<210> SEQ ID NO 349
<211> LENGTH: 9
<212> TYPE: PRT
<213> ORGANISM: Artificial Sequence
<220> FEATURE:
<223> OTHER INFORMATION: Top Ranked Peptide Library

<400> SEQUENCE: 349

Arg Pro Pro Ser Phe Gly Pro Phe Arg
 1               5

<210> SEQ ID NO 350
<211> LENGTH: 9
<212> TYPE: PRT
<213> ORGANISM: Artificial Sequence
<220> FEATURE:
<223> OTHER INFORMATION: Top Ranked Peptide Library

<400> SEQUENCE: 350

Arg Pro Phe Gly Pro Pro Ser Phe Arg
 1               5

<210> SEQ ID NO 351
<211> LENGTH: 9
<212> TYPE: PRT
```

```
<213> ORGANISM: Artificial Sequence
<220> FEATURE:
<223> OTHER INFORMATION: Top Ranked Peptide Library

<400> SEQUENCE: 351

Arg Pro Pro Gly Pro Ser Phe Phe Arg
 1               5

<210> SEQ ID NO 352
<211> LENGTH: 9
<212> TYPE: PRT
<213> ORGANISM: Artificial Sequence
<220> FEATURE:
<223> OTHER INFORMATION: Top Ranked Peptide Library

<400> SEQUENCE: 352

Arg Phe Pro Pro Gly Ser Pro Phe Arg
 1               5

<210> SEQ ID NO 353
<211> LENGTH: 9
<212> TYPE: PRT
<213> ORGANISM: Artificial Sequence
<220> FEATURE:
<223> OTHER INFORMATION: Top Ranked Peptide Library

<400> SEQUENCE: 353

Arg Phe Gly Pro Pro Ser Pro Phe Arg
 1               5
```

METHOD FOR DE NOVO PEPTIDE SEQUENCE DETERMINATION

This application claims the priority benefit under 35 U.S.C. §119(a)–(d) of Great Britain Patent Application No. GB 9710582.9, filed on May 22, 1997.

FIELD OF THE INVENTION

The invention relates to a method for the determination of the precise linear sequence of amino acids in a peptide, polypeptide, or protein without recourse or reference to either a known pre-defined data base or to sequential amino acid residue analysis. As such, the method of the invention is a true, de novo peptide sequence determination method.

BACKGROUND OF THE INVENTION

The composition of a peptide, polypeptide, or protein as a sequence of amino acids is well understood. Each peptide, polypeptide, and protein is uniquely defined by a precise linear sequence of amino acids. Knowledge of the precise linear arrangement or sequence of amino acids in a peptide, polypeptide, or protein is required for various purposes, including DNA cloning in which the sequence of amino acids provides information required for oligonucleotide probes and polymerase chain reaction ("PCR") primers. Knowledge of the exact sequence also allows the synthesis of peptides for antibody production, provides identification of peptides, polypeptides, and proteins, aids in the characterization of recombinant products, and is useful in the study of post-translational modifications.

A variety of sequencing methods are available to obtain the amino acid sequence information. For example, a series of chemical reactions, e.g., Edman reactions, or enzymatic reactions, e.g., exo-peptidase reactions, are used to prepare sequential fragments of the unknown peptide. Either an analysis of the sequential fragments or a sequential analysis of the removed amino acids is used to determine the linear amino acid sequence of the unknown peptide. Typically, the Edman degradation chemistry is used in modern automated protein sequencers.

In the Edman degradation, a peptide, polypeptide, or protein is sequenced by degradation from the N-terminus using the Edman reagent, phenylisothiocyanate ("PITC"). The degradation process involves three steps, i.e., coupling, cleavage, and conversion. In the coupling step, PITC modifies the N-terminal residue of the peptide, polypeptide, or protein. An acid cleavage then cleaves the N-terminal amino acid in the form of an unstable anilinothiazolinone ("ATZ") derivative, and leaves the peptide, polypeptide, or protein with a reactive N-terminus and shortened by one amino acid. The ATZ derivative is converted to a stable phenylthiohydantoin in the conversion step for identification, typically with reverse phase high performance liquid chromatography ("RP-HPLC"). The shortened peptide, polypeptide, or protein is left with a free N-terminus that can undergo another cycle of the degradation reaction. Repetition of the cycle results in the sequential identification of each amino acid in the peptide, polypeptide, or protein. Because of the sequential nature of amino acid release, only one molecular substance can be sequenced at a time. Therefore, peptide, polypeptide, or protein samples must be extremely pure for accurate and efficient sequencing. Typically, samples must be purified with HPLC or SDS-PAGE techniques.

Although many peptide, polypeptide, and protein sequences have been determined by Edman degradation, currently, most peptide, polypeptide, and protein sequences are deduced from DNA sequences determined from the corresponding gene or cDNA. However, the determination of a protein sequence using a DNA sequencing technique requires knowledge of the specific nucleotide sequence used to synthesize the protein. DNA sequencing cannot be used where the nature of the protein or the specific DNA sequence used to synthesize the protein is unknown.

A peptide, polypeptide, or protein sequence may also be determined from experimental fragmentation spectra of the unknown peptide, polypeptide, or protein, typically obtained using activation or collision-induced fragmentation in a mass spectrometer. Tandem mass spectrometry ("MS/MS") techniques have been particularly useful. In MS/MS, a peptide is first purified, and then injected into a first mass spectrometer. This first mass spectrometer serves as a selection device, and selects a target peptide of a particular molecular mass from a mixture of peptides and polypeptides or proteins, and eliminates most contaminants from the analysis. The target molecule is then activated or fragmented to form a mixture from the target or parent peptide of various peptides of a lower mass that are fragments of the parent. The mixture is then selected through a second mass spectrometer (i.e. step), generating a fragment spectrum.

Typically, in the past, the analysis of fragmentation spectra to determine peptide sequences has involved hypothesizing one or more amino acid sequences based on the fragmentation spectrum. In certain favorable cases, an expert researcher can interpret the fragmentation spectra to determine the linear amino acid sequence of an unknown peptide. The candidate sequences may then be compared with known amino acid sequences in protein sequence libraries.

In one strategy, the mass of each amino acid is subtracted from the molecular mass of the parent peptide to determine the possible molecular mass of a fragment, assuming that each amino acid is in a terminal position. The experimental fragment spectrum is then examined to determine if a fragment with such a mass is present. A score is generated for each amino acid, and the scores are sorted to generate a list of partial sequences for the next subtraction cycle. The subtraction cycle is repeated until subtraction of the mass of an amino acid leaves a difference of between –0.5 and 0.5, resulting in one or more candidate amino acid sequences. The highest scoring candidate sequences are then compared to sequences in a library of known protein sequences in an attempt to identify a protein having a sub-sequence similar or identical to the candidate sequence that generated the fragment spectrum.

Although useful in certain contexts, there are difficulties related to hypothesizing candidate amino acid sequences based on fragmentation spectra. The interpretation of fragmentation spectra is time consuming, can generally be performed only in a few laboratories that have extensive experience with mass spectrometry, and is highly technical and often inaccurate. Human interpretation is relatively slow, and may be highly subjective. Moreover, methods based on peptide mass mapping are limited to peptide masses derived from an intact homogeneous peptide, polypeptide, or protein generated by specific, known proteolytic cleavage, and, thus, are not applicable in general to a mixture of peptides, polypeptides, or proteins.

U.S. Pat. No. 5,538,897 to Yates, III et al. provides a method of correlating the fragmentation spectrum of an unknown peptide with theoretical spectra calculated from described peptide sequences stored in a database to match the amino acid sequence of the unknown peptide to that of a described peptide. Known amino acid sequences, e.g., in a protein sequence library, are used to calculate or predict one or more candidate fragment spectra. The predicted fragment spectra are then compared with the experimentally-obtained fragment spectrum of the unknown protein to determine the best match or matches. Preferably, the mass of the unknown peptide is known. Sub-sequences of the various sequences in the protein sequence library are analyzed to identify those sub-sequences corresponding to a peptide having a mass equal to or within a given tolerance of the mass of the parent peptide in the fragmentation spectrum. For each sub-sequence having the proper mass, a predicted fragment spectrum can be calculated by calculating masses of various amino acid subsets of the candidate peptide. As a result, a plurality of candidate peptides, each having predicted fragment spectrum, is obtained. The predicted fragment spectra are then compared with the fragment spectrum obtained experimentally for the unknown protein to identify one or more proteins having sub-sequences that are likely to be identical to the sequence of peptides that resulted in the experimentally-derived fragment spectrum. However, this technique cannot be used to derive the sequence of unknown, novel proteins or peptides having no sequence or sub-sequence identity with those pre-described or contained in such databases, and, thus, is not a de novo sequencing method.

Therefore, there remains a need for a true de novo sequencing method of determining the amino acid sequence of a peptide using mass spectrometry.

SUMMARY OF THE INVENTION

The present invention is directed to a method for generating a library of peptides, wherein each peptide in the library has a molecular mass corresponding to the same predetermined molecular mass. Typically, the library of peptides is then used to determine the amino acid sequence of an unknown peptide having the predetermined molecular mass. Preferably, the predetermined molecular mass used to generate the library is the molecular mass of the unknown peptide. Most preferably, the molecular mass of the unknown peptide is determined prior to the generation of the library using a mass spectrometer, such as a time-of-flight mass spectrometer.

The library is synthetic, i.e., not pre-described, and is typically generated each time a peptide is analyzed, based on the predetermined molecular mass of the unknown peptide. The library is generated by defining a set of all allowed combinations of amino acids that can be present in the unknown peptide, where the molecular mass of each combination corresponds to the predetermined molecular mass within the experimental accuracy of the device used to determine the molecular mass, allowing for water lost in peptide bond formation and for protonation, and generating an allowed library of all possible permutations of the linear sequence of amino acids in each combination in the set.

Generally, the present invention is directed to a method for determining the amino acid sequence of an unknown peptide, which comprises determining a molecular mass and an experimental fragmentation spectrum for the unknown peptide, comparing the experimental fragmentation spectrum of the unknown peptide to theoretical fragmentation spectra calculated for each individual member of an allowed synthetic peptide library, where the allowed peptide library is of the type described above, and identifying a peptide in the peptide library having a theoretical fragmentation spectrum that matches most closely the fragmentation spectrum of the unknown peptide, from which it is inferred that the amino acid sequence of the identified peptide in the allowed library represents the amino acid sequence of the unknown peptide.

The molecular mass for the unknown peptide may be determined by any means known in the art, but is preferably determined with a mass spectrometer. Allowed combinations of amino acids are chosen from a set of allowed amino acids that typically comprises the natural amino acids, i.e., tryptophan, arginine, histidine, glutamic acid, glutamine, aspartic acid, leucine, threonine, proline, alanine, tyrosine, phenylalanine, methionine, lysine, asparagine, isoleucine, cysteine, valine, serine, and glycine, but may also include other amino acids, including, but not limited to, non-natural amino acids and chemically modified derivatives of the natural amino acids, e.g., carbamidocysteine and deoxymethionine. Allowed combinations of amino acids are then calculated using one or more individual members of this set of amino acids, allowing for known mass changes associated with peptide bond formation, such that the total mass of each allowed combination corresponds to the predetermined mass of the unknown peptide to within the experimental accuracy to which this molecular mass of the unknown peptide was calculated, typically about 30 ppm. The set of allowed combinations is most easily calculated using an appropriately programmed computer. The allowed peptide library is assembled by permutation in all possible linear combinations of each allowed amino acid composition, and is also most easily constructed using an appropriately programmed computer. It should be noted that the term "allowed" with respect to amino acid combinations and libraries of peptides refers to combinations and libraries specific to the unknown peptide under investigation. The peptide library is constructed from the amino acid combinations, which in turn are calculated from the experimentally determined molecular mass. As unknown peptides of different mass are investigated, so different combinations of amino acids are allowed, and hence each unknown peptide of unique molecular mass gives rise to a unique peptide library.

The nature of the fragmentation process from which the theoretical fragmentation spectrum is calculated for every peptide in the allowed library may be of any type known in the art, such as a mass spectrum or a protease or chemical fragmentation spectrum. Preferably, both the molecular mass and the fragmentation spectrum for the unknown peptide are obtained from a tandem mass spectrometer. The immonium ion region of the mass spectrum used to determine the molecular mass may also be used to identify amino acids contained in the unknown peptide. The identity of these amino acids is then used to constrain the allowed library. The amino acid sequence of the peptide from the allowed library of peptides, having a calculated fragmentation spectrum that best fits the experimental fragmentation spectrum of the unknown peptide, corresponds to the amino acid sequence of the unknown peptide.

Although not required, the experimental fragmentation spectrum is generally normalized. A factor that is an indication of closeness-of-fit between the experimental fragmentation spectrum of the unknown peptide, polypeptide, or protein and each of the theoretical fragmentation spectra calculated for the peptide library may then be calculated to determine which of the theoretical fragmentation spectra best fits the experimental fragmentation spectrum. Preferably, peak values in the fragmentation spectra having an intensity greater than a predetermined threshold value are selected when calculating the indication of closeness-of-fit. The theoretical fragmentation spectrum that best fits the experimental fragmentation spectrum corresponds to the amino acid sequence in the allowed library that matches that of the unknown peptide, polypeptide, or protein.

DETAILED DESCRIPTION OF THE INVENTION

The present invention is directed to a de novo method for determining the sequence of an unknown peptide without reference to any experimentally determined peptide or nucleotide sequence, and without recourse to a sequential and step-wise identification and ordering of individual amino acid residues, such as the Edman degradation process or interpretation of conventional mass spectrometry fragmentation patterns. In the method of the invention, a library of theoretical peptide sequences is generated from a predetermined molecular mass, preferably the experimentally determined molecular mass of an unknown peptide. As such, this library must contain the amino acid sequence of the unknown peptide, as well as that of any other peptide having the predetermined molecular mass. The precise amino acid sequence of the unknown is identified by applying standard correlation functions to select that peptide from the synthetic library whose calculated, i.e., theoretical, fragmentation spectrum most closely matches the fragmentation pattern of the unknown. In the preferred embodiment, the fragmentation spectrum is a mass spectrum and the correlation method is the function described in U.S. Pat. No. 5,538,897, the contents of which are incorporated herein in their entirety by reference. Preferably, the theoretical fragmentation spectra are generated and matched to the fragmentation pattern of the unknown using an appropriately programmed computer.

Figure 1:
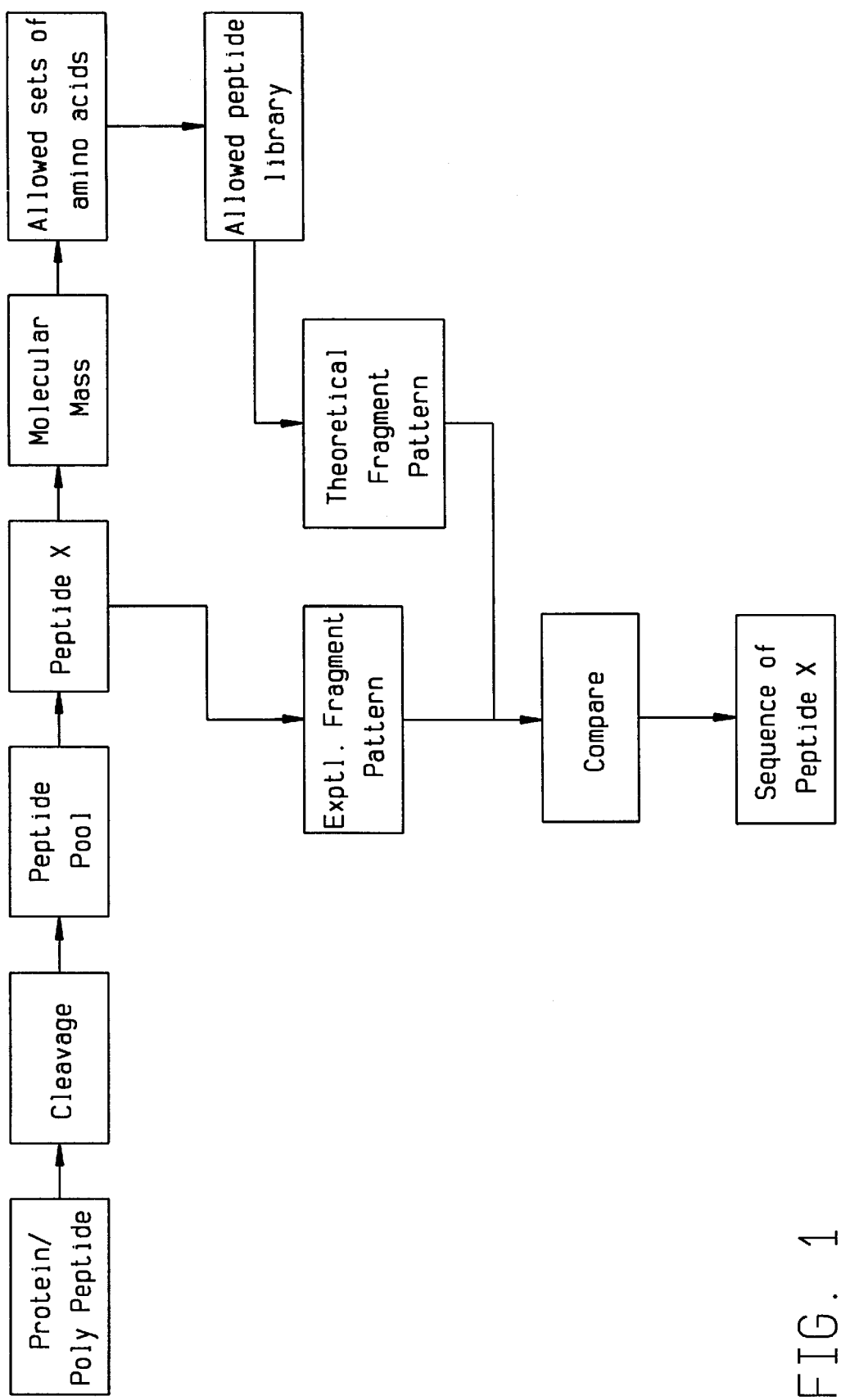
FIG. 1 is a flow chart of the method of the invention.

The invention may be better understood by reference to the flow chart provided in FIG. 1. Where the peptide is a protein or large polypeptide, the protein or large polypeptide may be cleaved to form a peptide pool by means well known in the art. The unknown peptide ("Peptide X") is then separated from the pool by HPLC or any other means known in the art, preferably mass spectrometry, and the molecular mass of Peptide X is determined. Although there are a number of methods for determining the molecular mass of Peptide X the preferred method is again mass spectrometry.

A set of amino acids that theory or experimental results teach may be included in Peptide X is then defined for consideration in determining the sequence of Peptide X. The defined set of amino acids may include modified or unnatural amino acids in addition to natural amino acids.

Typically, the method of the invention requires a "naked" peptide when determining the amino acid sequence. Therefore, the peptide should be free of any individual amino acids that are covalently modified by post-translational modification, such as, e.g., glycosylation, which involves the attachment of carbohydrate to the side chain of certain amino acids. Where the method of the invention is used to determine the amino acid sequence of a post-translationally modified peptide, the modifications are typically removed from the peptide prior to the analysis, taking due care to leave the peptide intact. Methods for removing post-translational modifications from peptides are well known in the art, and include, for example, the removal of N-linked carbohydrates with enzymes, such as peptide-N-glycosidase F (PNGase F), endo-glycosidases, mixtures of exo-glycosidases, etc., and the removal of phosphate modification with phosphatases. In addition, other techniques for removing modifications occasionally found on peptides are well known in the art. However, where a specific modification to a specific amino acid is known to be present in the unknown peptide, the modified amino acid may be included in the defined set of amino acids that theory or experimental results teach may be included in Peptide X, and, thus, the sequence of the peptide containing the modified peptide may be determined with the method of the present invention.

All combinations of amino acids having a total mass equal to the measured mass of Peptide X are calculated, allowing for water lost in determining peptide links, protonation, etc. Any individual amino acid may be included as part of any given combination at any integral stoichiometry up to the amount consistent with the mass determined for Peptide X. These combinations comprise all of the allowed combinations of amino acids combinations for Peptide X, and, therefore, the actual amino acid compositions of Peptide X will be represented in one and only one of these combinations. Furthermore, these combinations are generally peptide specific.

An allowed library of linear peptides is then constructed from the allowed combinations of amino acids. The allowed library is constructed by generating all possible linear permutations of the sequence of amino acids in each combination, using all the amino acids in each combination. The allowed library comprises all such permutations of the amino acids, and therefore must include Peptide X. The allowed library of peptides having the same molecular mass as Peptide X is typically constructed independently and ab initio for each new unknown peptide that is sequenced. That is, a new library is typically constructed as part of each analysis, and for only that analysis. However, as will be clear to one of ordinary skill in the art, once a library of all peptides, polypeptides, or proteins having a given molecular mass has been constructed, that library may be used for the determination of the amino acid sequence of any other peptide, polypeptide, or protein of that particular molecular mass.

This differs fundamentally from existing data base approaches in which a single data base of known sequences, which is subject to periodic updates and refinements based on the availability of experimentally determined sequences, is used for all analyses. As a result, with the method of the present invention, the determination of new and previously unknown peptides sequences that are not present in any experimentally determined peptide sequence library is possible by direct peptide analysis in a non-step-wise, operator-independent automated process. In addition, the method of the invention is not constrained to the conventional twenty amino acids, or to their conventional modifications.

Figure 2:
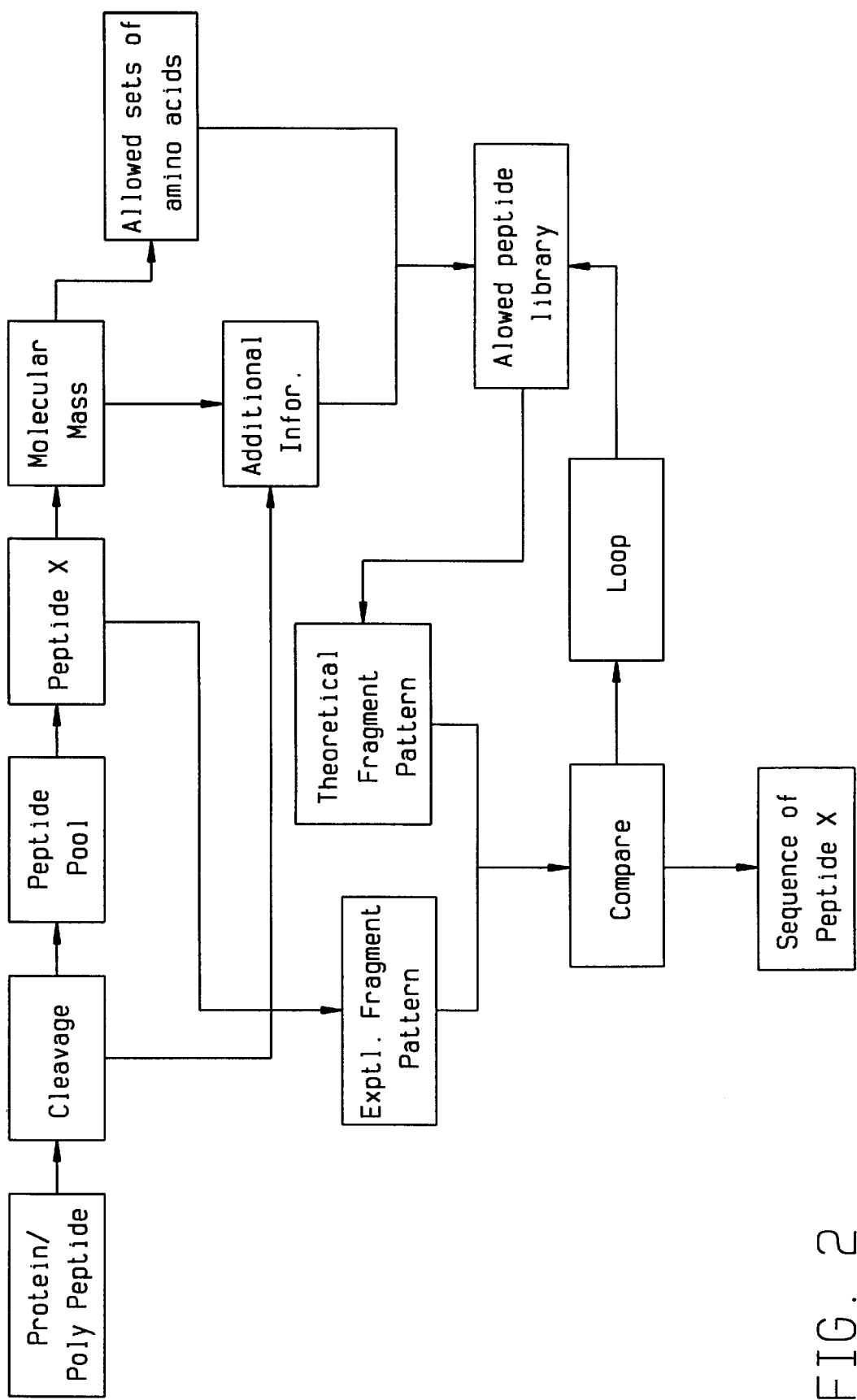
FIG. 2 is a flow chart of a preferred embodiment of the invention.

In a preferred embodiment, as shown in the flow chart provided in FIG. 2, additional information relating to Peptide X is used to place constraints on the allowed combinations of amino acids and/or allowed peptide sequences in the library, and, thus, reduce the number of possible sequences. Useful information related to Peptide X includes, but is not limited to, partial amino acid composition. For example, the mass spectrum used to determine the mass of Peptide X may include fragments that can be used to identify specific amino acids present in Peptide X. Where it is known that certain amino acids are definitely present in Peptide X, constraints are placed on the allowed combinations and allowed library by requiring the identified amino acids to be present in all combinations and, thus, in every peptide present in the library.

Again with reference to FIGS. 1 and 2, the allowed library, which has preferably been constrained, is then used as the basis for generating theoretical fragmentation patterns that are compared to the experimental fragmentation pattern obtained for Peptide X. The fragmentation patterns may be obtained by any suitable means known in the art. Preferably, the fragmentation patterns are mass spectra, and the method used to match the theoretical and experimental mass spectra is that disclosed in U.S. Pat. No. 5,538,897. However, protease or chemical fragmentation, coupled to HPLC separation of the fragments, may also be used to obtain the experimental fragmentation patterns.

Preferably, in a determination of the amino acid sequence of Peptide X, the molecular mass of Peptide X is determined with high accuracy, typically, to within about 30 ppm (parts per million). An example of such a spectrum is provided in FIG. 3, where the molecular mass of Peptide X is determined from the peak at 774.3928 daltons. In addition, as a result of the partial fragmentation of Peptide X that can occur, fragments that identify certain amino acids that are contained in Peptide X are also observed, allowing the peptide library to be constrained. An example of this portion of the mass spectrum for Peptide X is provided in FIG. 4.

Peptide X is then subjected to collision-induced dissociation in a mass spectrometer. The parent peptide and its fragments are then introduced into the second mass spectrometer that provides an intensity or count and the mass to charge ratio, m/z, for each of the fragments in the fragment mixture. Each fragment ion is represented in a bar graph in which the abscissa value is m/z and the ordinate value is the intensity. A variety of mass spectrometer types can be used, including, but not limited to a triple-quadrapole mass spectrometry, Fourier-transform cyclotron resonance mass spectrometry, tandem time-of-flight mass spectrometry, and quadrapole ion trap mass spectrometry.

The experimental fragment spectrum is then compared to the mass spectra predicted for the sequences of the allowed library to identify one or more predicted mass spectra that closely match the experimental mass spectrum. Because the allowed library includes all permutations of amino acid sequences that have a total mass corresponding to that of Peptide X, Peptide X must be represented in the allowed library.

The predicted fragmentation spectra may be obtained and compared to the experimental fragmentation spectrum by employing a method that involves first normalizing the experimental fragmentation spectrum. This may be accomplished by converting the experimental fragmentation spectrum to a list of masses and intensities. The peak values for Peptide X are removed, and the square root of the remaining intensity values is calculated, and normalized to a maximum value of 100. The 200 most intense ions are divided into ten mass regions, and the maximum intensity within each region is again normalized to 100. Each ion within 3.0 daltons of its neighbor on either side is given an intensity value equal to the greater of the intensity of the ion or that of its neighbor. Other normalization methods can be used, and it is possible to perform the analysis without normalizing. However, in general, normalization is preferred. In particular, maximum normalized values, the number of intense ions, the number of mass regions, and the size of the window for assuming the intensity value of a near neighbor may all be independently varied to larger or smaller values.

A fragment mass spectrum is predicted for each of the candidate sequences. The fragment mass spectrum is predicted by calculating the fragment ion masses for the type b and y ions for the amino acid sequence. When a peptide is fragmented and the charge is retained on the N-terminal cleavage fragment, the resulting ion is labelled as a b-type ion. If the charge is retained on the C-terminal fragment, it is labelled a y-type ion. Masses for type b ions were calculated by summing the amino acid masses and adding the mass of a proton. Masses for type y ions were calculated by summing, from the C-terminus, the masses of the amino acids and adding the mass of water and a proton to the initial amino acid. In this way, it is possible to calculate an m/z value for each fragment.

However, in order to provide a predicted mass spectrum, it is also necessary to assign an intensity value for each fragment. Although it is often possible to predict, on a theoretical basis, intensity value for each fragment, this procedure is difficult, and it has been found useful to assign intensities in the following fashion. The value of 50.0 is assigned to each b and y ion. To masses of 1 dalton on either side of the fragment ion, an intensity of 25.0 is assigned. Peak intensities of 10.0 are assigned at masse peaks 17.0 and 18.0 daltons below the m/z of each b and y ion location to account for both $NH_3$ and $H_2O$ loss, and peak intensities of 10.0 are assigned to mass peaks 28.0 daltons below each type b ion location to account for CO loss.

After calculation of predicted m/z values and assignment of intensities, it is preferred to calculate a measure of closeness-of-fit between the predicted mass spectra and the experimentally-derived fragment spectrum. A number of methods for calculating closeness-of-fit are available. For example, a two-step method may be used that includes calculating a preliminary closeness-of-fit score, referred to here as $S_p$, and calculating a correlation function for the highest-scoring amino acid sequences. In the preferred embodiment, $S_p$ is calculated using the following formula:

$$S_p = (\Sigma i_m) * n^*_i (1+\beta) * (1-\rho)/n_\tau \qquad (1)$$

where $i_m$ are the matched intensities, $n_i$ are the number of matched fragment ions, $\beta$ is the type b and y ion continuity, $\rho$ is the presence of immonium ions and their respective amino acids in the predicted sequence, and $n_\tau$ is the total number of fragment ions. The factor, $\beta$, evaluates the continuity of a fragment ion series. If there is a fragment ion match for the ion immediately preceding the current type b or y ion, β is incremented by 0.075 from an initial value of 0.0. This increases the preliminary score for those peptides matching a successive series of type b and y ions, since extended series of ions of the same type are often observed in MS/MS spectra. The factor ρ evaluates the presence of immonium ions in the low mass end of the mass spectrum.

The detection of immonium ions may be used diagnostically to determine the presence of certain types of amino acids in the sequence. For example, if immonium ions are present at 110.0, 120.0, or 136.0±1.0 daltons in the processed data file of the unknown peptide with normalized intensities greater than 40.0, indicating the presence of histidine, phenylalanine, and tyrosine respectively, then the sequence under evaluation is checked for the presence of the amino acid indicated by the immonium ion. The preliminary score, $S_p$, for the peptide is either increased or decreased by a factor of 1−ρ, where ρ is the sum of the penalties for each of the three amino acids whose presence is indicated in the low mass region. Each individual ρ can take on the value of −0.15 if there is a corresponding low mass peak, and the amino acid is not present in the sequence, +0.15 if there is a corresponding low mass peak and the amino acid is present in the sequence, or 0.0 if the low mass peak is not present. The total penalty can range from −0.45, where all three low mass peaks are present in the spectrum, but are not present in the sequence, to +0.45, where all three low mass peaks are present in the spectrum, and are present in the sequence.

Following the calculation of the preliminary closeness-of-fit score $S_p$. the predicted mass spectra having the highest $S_p$ scores are selected for further analysis using the correlation function. The number of candidate predicted mass spectra that are selected for further analysis will depend largely on the computational resources and time available.

For purposes of calculating the correlation function, the experimentally-derived fragment spectrum is typically pre-processed in a fashion somewhat different from preprocessing employed before calculating $S_p$. For purposes of the correlation function, the precursor ion is removed from the spectrum, and the spectrum is divided into 10 sections. Ions in each section are then normalized to 50.0. The section-wise normalized spectra are then used for calculating the correlation function. The discrete correlation between the two functions may be calculated as:

$$R_\tau = \sum_{i=0}^{n-1} x_i y_i + \tau \quad (2)$$

where τ is a lag value. The discrete correlation theorem states that the discrete correlation of two real functions x and y is one member of the discrete Fourier transform pair $$R_\tau \Leftrightarrow X_\tau Y^*\tau \quad (3)$$

where X(t) and Y(t) are the discrete Fourier transforms of x(i) and y(i), and the Y* denotes complex conjugation. Therefore, the cross-correlations can be computed by Fourier transformation of the two data sets using the fast Fourier transform (FFT) algorithm, multiplication of one transform by the complex conjugate of the other, and inverse transformation of the resulting product.

The predicted spectra as well as the pre-processed unknown spectrum may be zero-padded to 4096 data points, since the MS/MS spectra are not periodic, as intended by the correlation theorem, and the FFT algorithm requires N to be a integer power of two, so the resulting end effects need to be considered. The final score attributed to each candidate peptide sequence is R(0) minus the mean of the cross-correlation function over the range −75<t<75. This modified "correlation parameter", described in Powell and Heiftje, Anal. Chim. Acta, 100:313–327 (1978), shows better discrimination over just the spectral correlation coefficient R(0). The raw scores are normalized to 1.0. Preferably, the output includes the normalized raw score, the candidate peptide mass, the unnormalized correlation coefficient, the preliminary score, the fragment ion continuity β, the immonium ion factor τ, the number of type b and y ions matched out of the total number of fragment ions, their matched intensities, the protein accession number, and the candidate peptide sequence.

The correlation function can be used to automatically select one of the predicted mass spectra as corresponding to the experimentally-derived fragment spectrum. Preferably, however, a number of sequences from the library are output and final selection of a single sequence is done by a skilled operator.

Depending on the computing and time resources available, it may be advantageous to employ data-reduction techniques. Preferably these techniques will emphasize the most informative ions in the spectrum while not unduly affecting search speed. One technique involves considering only some of the fragment ions in the MS/MS spectrum, which, for a peptide may contain as many as 3,000 fragment ions. According to one data reduction strategy, the ions are ranked by intensity, and some fraction of the most intense ions is used for comparison. Another approach involves subdividing the spectrum into a small number of regions, e.g., about 5, and using the 50 most intense ions in each region as part of the data set. Yet another approach involves selecting ions based on the probability of those ions being sequence ions. For example, ions could be selected which exist in mass windows of 57 through 186 daltons, i.e., the range of mass increments for the 20 common amino acids from glycine to tryptophan that contain diagnostic features of type b or y ions, such as losses of 17 or 18 daltons, corresponding to ammonia and water, or a loss of 28 daltons, corresponding to CO.

A number of different scoring algorithms can be used for determining preliminary closeness of fit or correlation. In addition to scoring based on the number of matched ions multiplied by the sum of the intensity, scoring can be based on the percentage of continuous sequence coverage represented by the sequence ions in the spectrum. For example, a 10 residue peptide will potentially contain 9 each of b and y type sequence ions. If a set of ions extends from $b_1$ to $b_9$, then a score of 100 is awarded, but if a discontinuity is observed in the middle of the sequence, such as missing the $b_5$ ion, a penalty is assessed. The maximum score is awarded for an amino acid sequence that contains a continuous ion series in both the b and y directions.

In the event the described scoring procedures do not delineate an answer, an additional technique for spectral comparison can be used in which the database is initially searched with a molecular weight value and a reduced set of fragment ions. Initial filtering of the database occurs by matching sequence ions and generating a score with one of the methods described above. The resulting set of answers will then undergo a more rigorous inspection process using a modified full MS/MS spectrum.

For the second stage analysis, one of several spectral matching approaches developed for spectral library searching is used. This will require generating a "library spectrum" for the peptide sequence based on the sequence ions predicted for that amino acid sequence. Intensity values for sequence ions of the "library spectrum" will be obtained from the experimental spectrum. If a fragment ion is predicted at m/z 256, then the intensity value for the ion in the experimental spectrum at m/z 256 will be used as the intensity of the ion in the predicted spectrum. Thus, if the predicted spectrum is identical to the "unknown" spectrum, it will represent an ideal spectrum. The spectra will then be compared using a correlation function. In general, it is believed that the majority of computational time for the above procedure is spent in the iterative search process. By multiplexing the analysis of multiple MS/MS spectra in one pass through the database, an overall improvement in efficiency will be realized. In addition, the mass tolerance used in the initial pre-filtering can affect search times by increasing or decreasing the number of sequences to analyze in subsequent steps.

Another approach to speed up searches involves a binary encryption scheme where the mass spectrum is encoded as peak/no peak at every mass depending on whether the peak is above a certain threshold value. If intensive use of a protein sequence library is contemplated, it may be possible to calculate and store predicted mass values of all subsequences within a predetermined range of masses so that at least some of the analysis can be performed by table look-up rather than calculation.

EXAMPLES

The following non-limiting examples are merely illustrative of the preferred embodiments of the present invention, and are not to be construed as limiting the invention, the scope of which is defined by the appended claims.

Example 1

Figure 3:
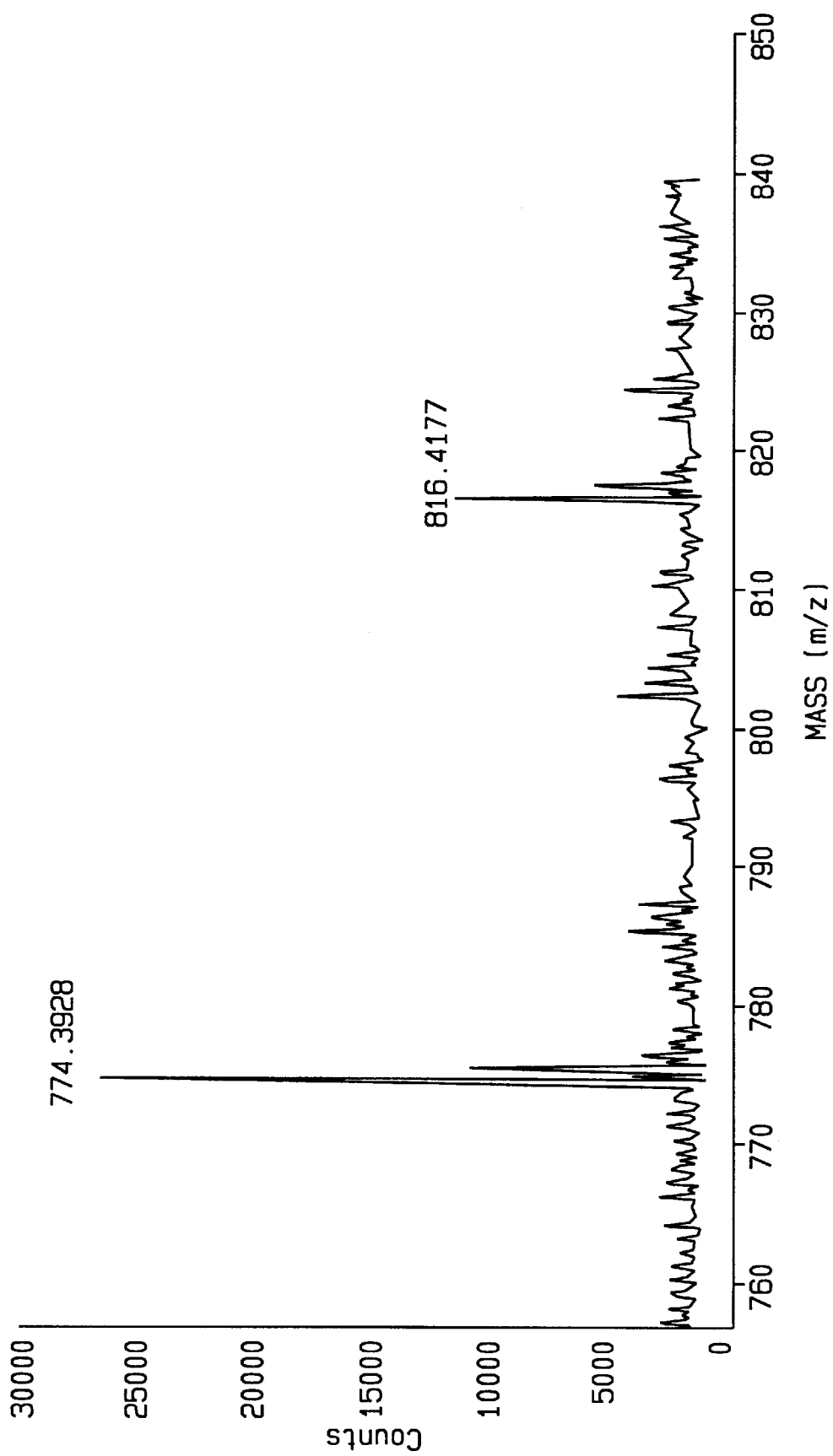
FIG. 3 is the experimental mass spectrum used to determine the molecular mass of unknown Peptide X.
Figure 4:
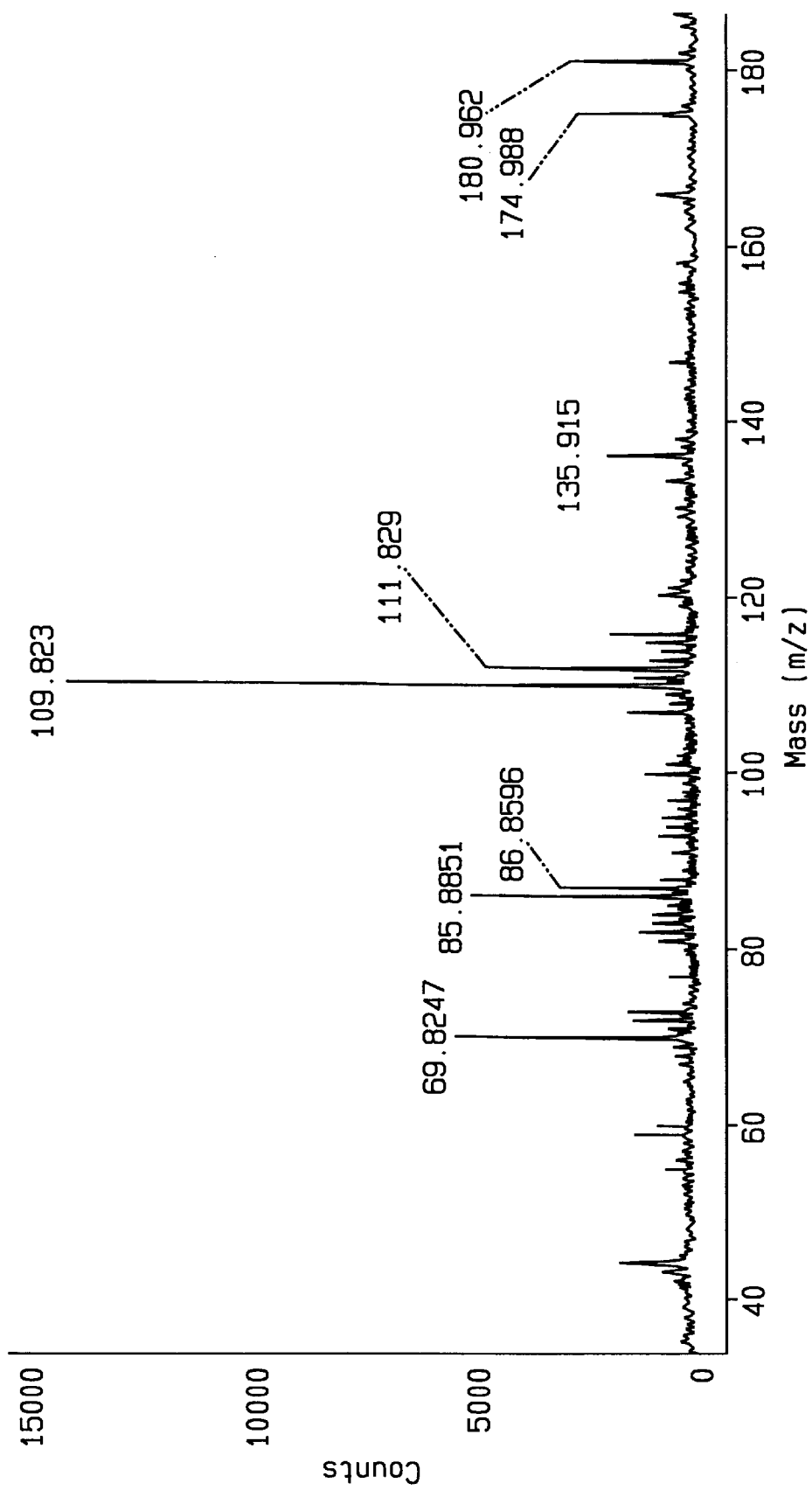
FIG. 4 is the immonium ion region of the mass spectrum shown in FIG. 3, and identifies amino acids contained in unknown Peptide X.

The amino acid sequence of unknown Peptide X was determined using the method of the invention. The molecular mass of Peptide X was first determined using a matrix-assisted laser-desorption time-of-flight mass spectrometer (Voyager Elite, manufactured by Perseptive Biosystems) with delayed extraction and post source decay. As shown in FIG. 3, the mass of the protonated form of peptide X is 774.3928 daltons, which indicates a sass of 773.3928 daltons for Peptide X.

The set of amino acids that are possibly part of Peptide X were then defined for consideration in the analysis. The defined set of amino acids with the molecular mass of each amino acid less the mass of the one water molecule lost during peptide bond formation is provided below. The molecular masses are given in daltons or a.m.u.

| | | | |
|---|---|---|---|
| tryptophan = | 186.079313 | carbamido cysteine = | 160.03065 |
| arginine = | 156.10111 | phenylalanine = | 147.068414 |
| histidine = | 137.058912 | methionine = | 131.04085 |
| glutamic acid = | 129.042593 | lysine = | 128.094963 |
| glutamine = | 128.058577 | asparagine = | 114.042927 |
| aspartic acid = | 115.026943 | isoleucine = | 113.084064 |
| leucine = | 113.084064 | cysteine = | 103.009185 |
| threonine = | 101.047678 | valine = | 99.068414 |
| proline = | 97.052764 | serine = | 87.032028 |
| alanine = | 71.037114 | glycine = | 57.021464 |
| tyrosine = | 163.063328 | | |

The allowed combinations of amino acids for Peptide X were determined by first determining the molecular mass of Peptide X, as described above, to an experimental accuracy of 30 ppm (parts per million). Therefore, each allowed combination of amino acids in the allowed library must have a total mass of 773.3928±30 ppm. In addition to providing the molecular mass of Peptide X, the first mass spectrum also confirmed the presence of certain amino acids in Peptide X. The immonium region of this mass spectrum, which shows the presence of these amino acids, is given in FIG. 4. In particular, the immonium region of the spectrum indicates the presence of arginine with a characteristic mass of 174.988, leucine/isoleucine with a characteristic mass at 85.8851 (these amino acids have the same mass, and are therefore not distinguishable by mass alone), histidine with a characteristic mass at 109.823, and tyrosine with a characteristic mass at 135.915. Therefore, it was possible to constrain the allowed library to sets containing arginine, leucine/isoleucine, histidine, and tyrosine, having a total molecular mass of 773.3928±30 ppm.

To determine the sets of amino acids that have a total molecular mass of 773.3928±30 ppm, the following equation was applied:

$$MM_x = \Sigma(\text{histidine}) + (\text{tyrosine}) + (\text{leucine/isoleucine}) + (\text{arginine}) + (H_2O) + (aa_1) + \text{---} + (aa_n),$$

where $aa_1$ - - - $aa_n$ are any of the allowed amino acids, other than arginine, isoleucine, histidine, and tyrosine. The only combinations of amino acids that can have a total molecular mass of 773.3928±30 ppm are as follows:

1) tryptophan, arginine, leucine/isoleucine, histidine, and tyrosine.

2) glutamic acid, glycine, arginine, leucine/isoleucine, histidine, and tyrosine.

3) alanine, aspartic acid, arginine, leucine/isoleucine, histidine, and tyrosine.

These combinations constitute the allowed sets of amino acids for Peptide X.

In addition, Peptide X was obtained by a tryptic cleavage, and, therefore, from the accepted specificity of trypsin, Peptide X must also have lysine or arginine as its carboxy terminal amino acid. With this constraint, the allowed library of linear peptides was constructed from all individual linear permutations of combinations 1, 2, and 3. The allowed library includes 528 linear peptides, one set of 264 peptides containing isoleucine (SEQ ID NOS:1–264) (shown below) and a corresponding set of 264 peptides in which isoleucine is replaced by leucine (not shown).

1) YIHWR
2) IYHWR
3) YHIWR
4) HYIWR
5) IHYWR
6) HIYWR
7) YIWHR
8) IYWHR
9) YWIHR
10) WYIHR
11) IWYHR
12) WIYHR
13) YHWIR
14) HYWIR
15) YWHIR
16) WYHIR
17) HWYIR
18) WHYIR
19) IHWYR
20) HIWYR
21) IWHYR
22) WIHYR
23) HWIYR
24) WHIYR
25) YIHEGR
26) IYHEGR
27) YHIEGR
28) HYIEGR
29) IHYEGR

-continued

30) HIYEGR
31) YIEHGR
32) IYEHGR
33) YEIHGR
34) EYIHGR
35) IEYHGR
36) EIYHGR
37) YHEIGR
38) HYEIGR
39) YEHIGR
40) EYHIGR
41) HEYIGR
42) EHYIGR
43) IHEYGR
44) HIEYGR
45) IEHYGR
46) EIHYGR
47) HEIYGR
48) EHIYGR
49) YIHGER
50) IYHGER
51) YHIGER
52) HYIGER
53) IHYGER
54) HIYGER
55) YIGHER
56) IYGHER
57) YGIHER
58) GYIHER
59) IGYHER
60) GIYHER
61) YHGIER
62) HYGIER
63) YGHIER
64) GYHIER
65) HGYIER
66) GHYIER
67) IHGYER
68) HIGYER
69) IGHYER
70) GIHYER
71) HGIYER
72) GHIYER
73) YIEGHR
74) IYEGHR
75) YEIGHR
76) EYIGHR
77) IEYGHR
78) EIYGHR
79) YIGEHR
80) IYGEHR
81) YGIEHR
82) GYIEHR
83) IGYEHR
84) GIYEHR
85) YEGIHR
86) EYGIHR
87) YGEIHR
88) GYEIHR
89) EGYIHR
90) GEYIHR
91) IEGYHR
92) EIGYHR
93) IGEYHR
94) GIEYHR
95) EGIYHR
96) GEIYHR
97) YHEGIR
98) HYEGIR
99) YEHGIR
100) EYHGIR
101) HEYGIR
102) EHYGIR
103) YHGEIR
104) HYGEIR
105) YGHEIR
106) GYHEIR
107) HGYEIR
108) GHYEIR

-continued

109) YEGHIR
110) EYGHIR
111) YGEHIR
112) GYEHIR
113) EGYHIR
114) GEYHIR
115) HEGYIR
116) EHGYIR
117) HGEYIR
118) GHEYIR
119) EGHYIR
120) GEHYIR
121) IHEGYR
122) HIEGYR
123) IEHGYR
124) EIHGYR
125) HEIGYR
126) EHIGYR
127) IHGEYR
128) HIGEYR
129) IGHEYR
130) GIHEYR
131) HGIEYR
132) GHIEYR
133) IEGHYR
134) EIGHYR
135) IGEHYR
136) GIEHYR
137) EGIHYR
138) GEIHYR
139) HEGIYR
140) EHGIYR
141) HGEIYR
142) GHEIYR
143) EGHIYR
144) GEHIYR
145) YIHDAR
146) IYHDAR
147) YHIDAR
148) HYIDAR
149) IHYDAR
150) HIYDAR
151) YIDHAR
152) IYDHAR
153) YDIHAR
154) DYIHAR
155) IDYHAR
156) DIYHAR
157) YHDIAR
158) HYDIAR
159) YDHIAR
160) DYHIAR
161) HDYIAR
162) DHYIAR
163) IHDYAR
164) HIDYAR
165) IDHYAR
166) DIHYAR
167) HDIYAR
168) DHIYAR
169) YIHADR
170) IYHADR
171) YHIADR
172) HYIADR
173) IHYADR
174) HIYADR
175) YIAHDR
176) IYAHDR
177) YAIHDR
178) AYIHDR
179) IAYHDR
180) AIYHDR
181) YHAIDR
182) HYAIDR
183) YAHIDR
184) AYHIDR
185) HAYIDR
186) AHYIDR
187) IHAYDR

-continued

188) HIAYDR
189) IAHYDR
190) AIHYDR
191) HAIYDR
192) AHIYDR
193) YIDAHR
194) IYDAHR
195) YDIAHR
196) DYIAHR
197) IDYAHR
198) DIYAHR
199) YIADHR
200) IYADHR
201) YAIDHR
202) AYIDHR
203) IAYDHR
204) AIYDHR
205) YDAIHR
206) DYAIHR
207) YADIHR
208) AYDIHR
209) DAYIHR
210) ADYIHR
211) IDAYHR
212) DIAYHR
213) IADYHR
214) AIDYHR
215) DAIYHR
216) ADIYHR
217) YHDAIR
218) HYDAIR
219) YDHAIR
220) DYHAIR
221) HDYAIR
222) DHYAIR
223) YHADIR
224) HYADIR
225) YAHDIR
226) AYHDIR
227) HAYDIR
228) AHYDIR
229) YDAHIR
230) DYAHIR
231) YADHIR
232) AYDHIR
233) DAYHIR
234) ADYHIR
235) HDAYIR
236) DHAYIR
237) HADYIR
238) AHDYIR
239) DAHYIR
240) ADHYIR
241) IHDAYR
242) HIDAYR
243) IDHAYR
244) DIHAYR
245) HDIAYR
246) DHIAYR
247) IHADYR
248) HIADYR
249) IAHDYR
250) AIHDYR
251) HAIDYR
252) AHIDYR
253) IDAHYR
254) DIAHYR
255) IADHYR
256) AIDHYR
257) DAIHYR
258) ADIHYR
259) HDAIYR
260) HADIYR
261) HADIYR
262) AHDIYR
263) DAHIYR
264) ADHIYR

Figure 5:
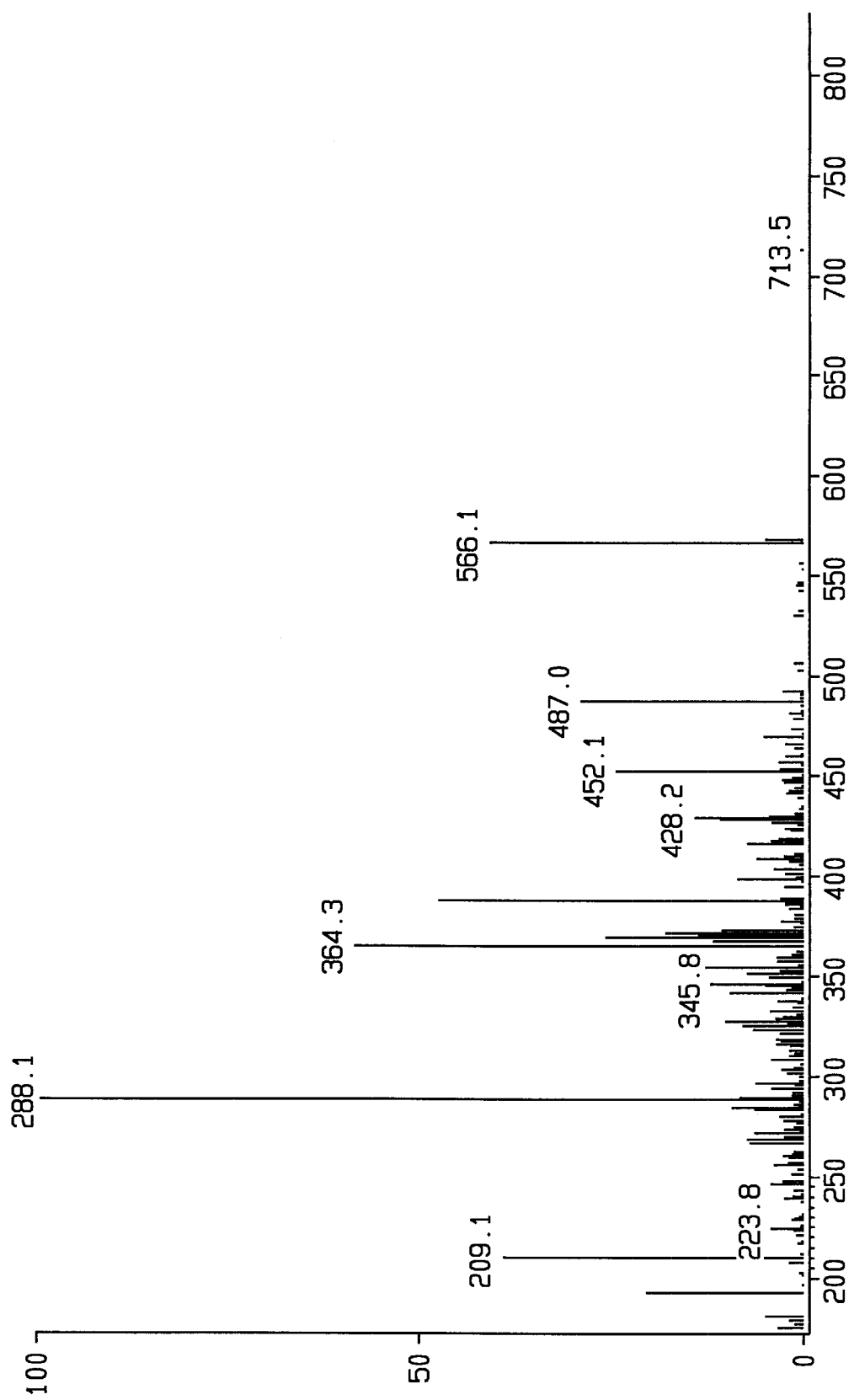
FIG. 5 is the experimental fragmentation mass spectrum of Peptide X.

The method of U.S. Pat. No. 5,538,897 was then used to match Peptide X to this library by MS/MS. The experimental tandem mass spectrum of Peptide X is shown in FIG. 5, and the 10 top ranking peptides matched to this spectrum are provided below (SEQ ID NOS:228, 238, 227, 237, 186, 226, 192, 225, 219, and 217, respectively). It was determined that the sequence of Peptide X is that of the top ranked peptide, AHYDIR (SEQ ID NO:228).

| Rank/Sp | (M + H) | Cn | C * $10^4$ | Sp | Ions | Reference | Peptide |
|---|---|---|---|---|---|---|---|
| 1/1 | 774.9 | 1.0000 | 1.8118 | 491.0 | 11/15 | p(228) | (−)AHYDIR |
| 2/3 | 774.9 | 0.9308 | 1.6864 | 386.2 | 10/15 | p(238) | (−)AHDYIR |
| 3/2 | 774.9 | 0.8012 | 1.4516 | 414.3 | 10/15 | p(227) | (−)HAYDIR |
| 4/5 | 774.9 | 0.7319 | 1.3262 | 320.5 | 9/15 | p(237) | (−)HADYIR |
| 5/1 | 774.9 | 0.7168 | 1.2987 | 491.0 | 11/15 | p(186) | (−)AHYIDR |
| 6/12 | 774.9 | 0.6131 | 1.1108 | 248.3 | 9/15 | p(226) | (−)AYHDIR |
| 7/3 | 774.9 | 0.6033 | 1.0930 | 386.2 | 10/15 | p(192) | (−)AHIYDR |
| 8/9 | 774.9 | 0.5878 | 1.0651 | 264.1 | 9/15 | p(225) | (−)YAHDIR |
| 9/50 | 774.9 | 0.5850 | 1.0599 | 156.5 | 7/15 | p(219) | (−)YDHAIR |
| 10/14 | 774.9 | 0.5825 | 1.0553 | 247.9 | 9/15 | p(217) | (−)YHDAIR |

Example 2

The amino acid sequence of Peptide Y, a known, standard peptide, was determined using the method of the invention, as applied to Peptide X in Example 1. Peptide Y has the following amino acid sequence: YGGFIRR (SEQ ID NO:265). The molecular mass of Peptide Y was determined to be 868.4719 to an experimental accuracy of 30 ppm from the mass spectrum shown in FIG. 6. The masses at 1296.6854 and 1570.6774 are from internal standards, added to allow instrument calibration.

The set of amino acids that are possibly part of Peptide Y were then defined for consideration in the analysis. The defined set of amino acids with the molecular mass of each amino acid less the mass of the one water molecule lost during peptide bond formation are the same as those used in Example 1.

Figure 6:
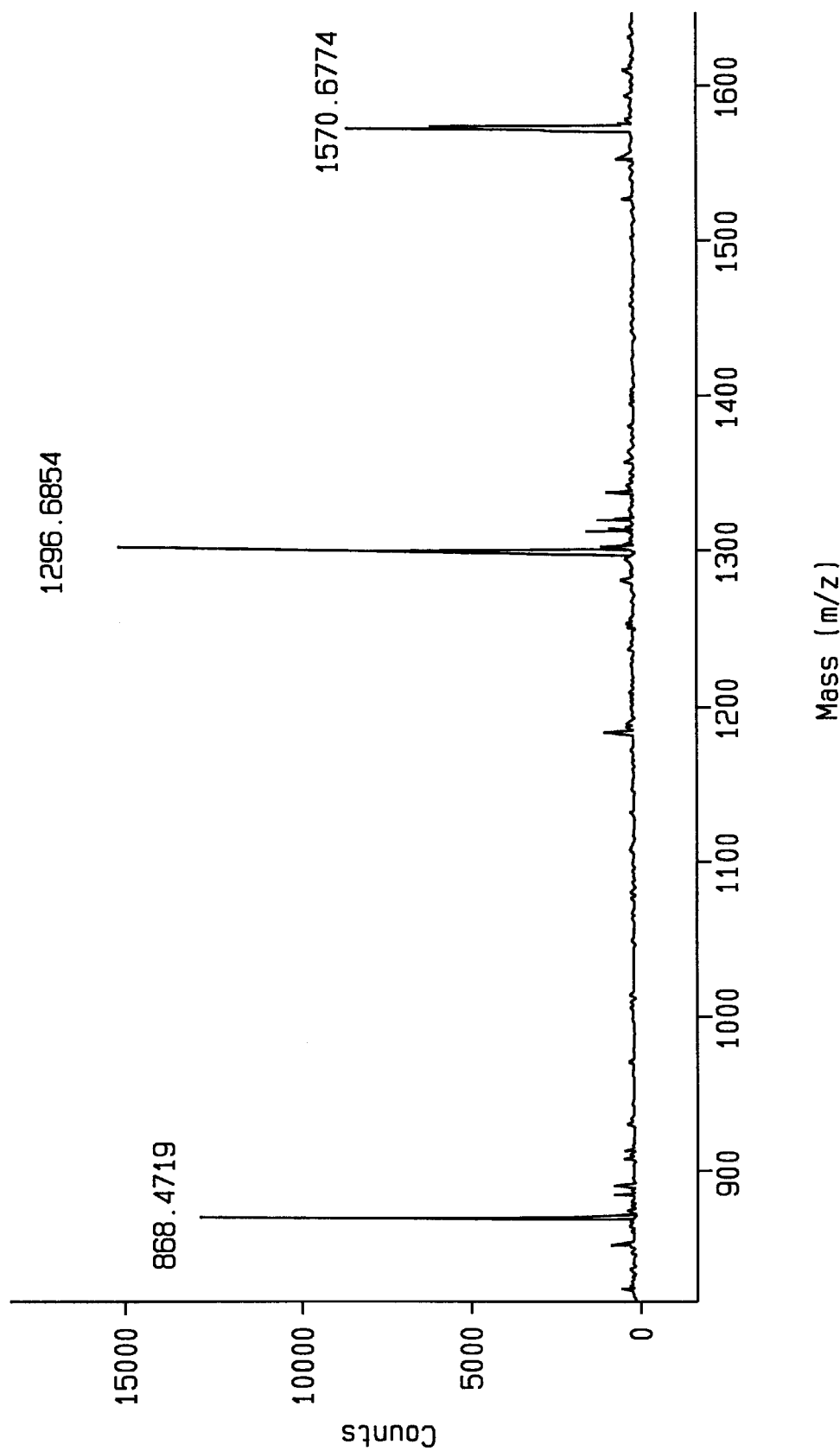
FIG. 6 is the experimental mass spectrum used to determine the molecular mass of Peptide Y.
Figure 7:
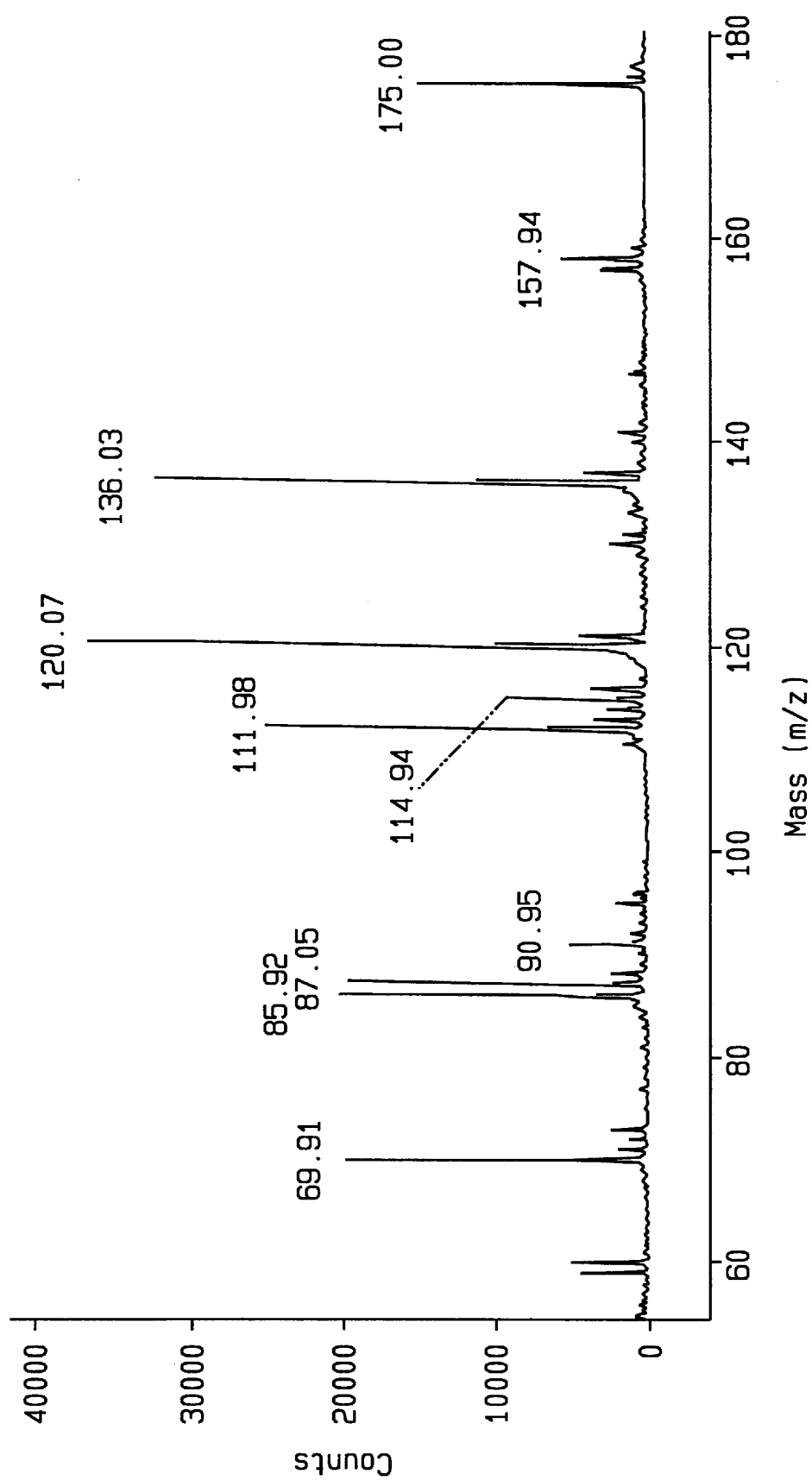
FIG. 7 is the immonium ion region of the mass spectrum shown in FIG. 6, and identifies amino acids contained in Peptide Y.

As the mass of Peptide Y was measured as 868.4719 to an experimental accuracy of ±30 ppm, each allowed amino acid combination must therefore have a total mass equal to 868.4719±30 ppm. In addition, from the immonium ion region of the PSD trace from FIG. 6, shown in FIG. 7, it was determined that Peptide Y must also contain the following amino acids: tyrosine with a characteristic mass at 136.027, phenylalanine with a characteristic mass at 120.071, arginine with a characteristic mass at 175.00, and leucine or isoleucine with a characteristic mass at 85.9225.

Application of the equation in Example 1 demonstrated that only the following combinations of amino acids are allowed for Peptide Y:

1) Tyrosine, phenylalanine, arginine, asparagine, and arginine.
2) Tyrosine, phenylalanine, arginine, arginine, leucine/isoleucine, glycine, and glycine.
3) Tyrosine, phenylalanine, arginine, leucine/isoleucine, alanine, alanine, and glutamine.
4) Tyrosine, phenylalanine, arginine, leucine/isoleucine, glycine, valine, and asparagine
5) Tyrosine, phenylalanine, arginine, leucine/isoleucine, glycine, glycine, glycine, and valine
6) Tyrosine, phenylalanine, arginine, leucine/isoleucine, glycine, alanine, alanine, and alanine These combinations constitute the allowed set of amino acid combinations for Peptide Y.

In addition, Peptide Y was obtained by a tryptic cleavage, and, thus, from the accepted specificity of trypsin, Peptide Y must also have lysine or arginine as its carboxy terminal amino acid. With this constraint, the allowed library of linear peptides for Peptide Y is constructed from all individual linear permutations of the combinations above. The allowed library includes over 20,000 peptides, and is thus not shown.

Figure 8:
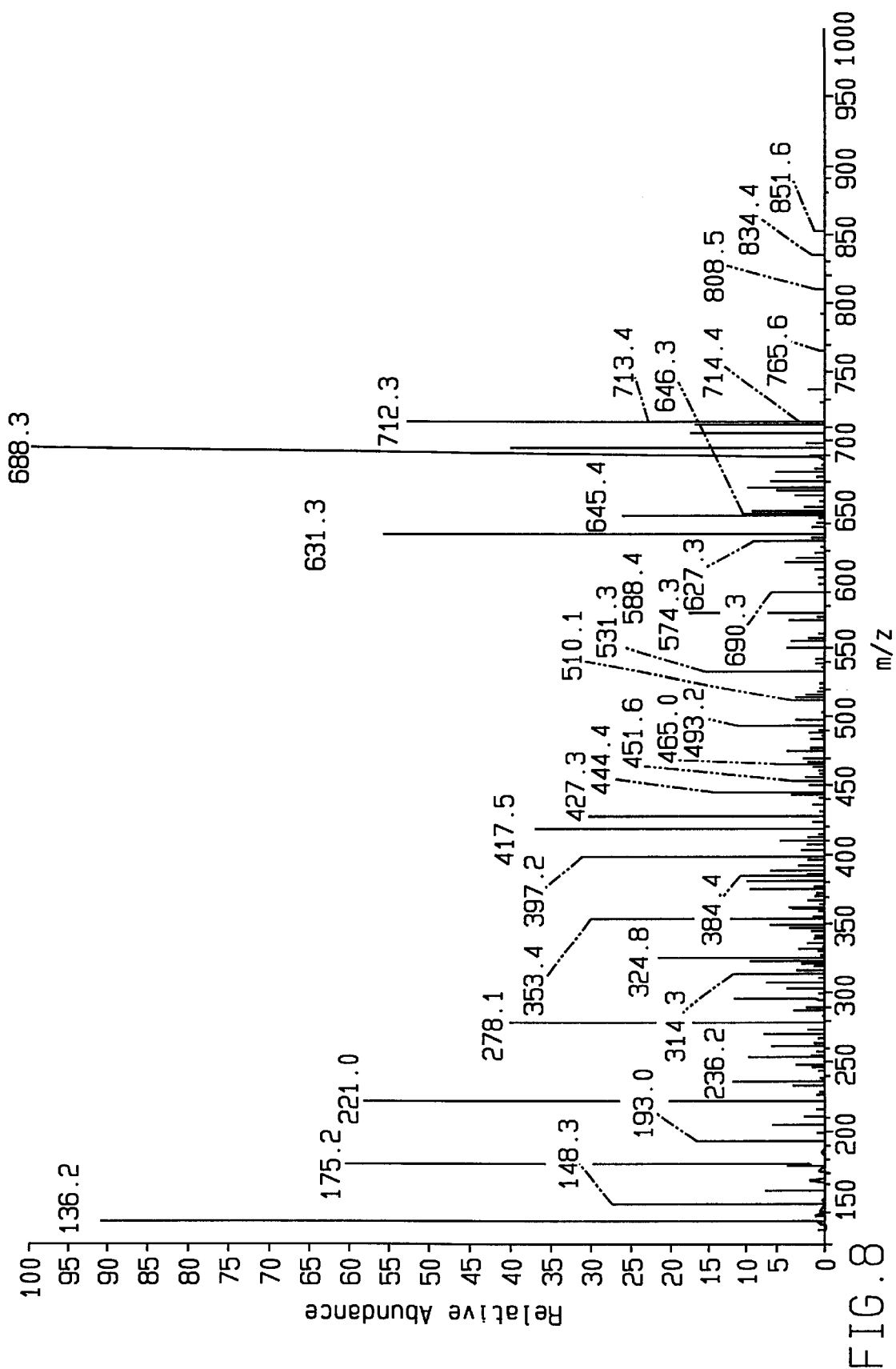
FIG. 8 is the experimental tandem mass spectrum of Peptide Y.

As with Example 1, the method of U.S. Pat. No. 5,538,897 was then used to match Peptide Y to this library by tandem mass spectrometry. The experimental tandem mass spectrum of Peptide Y is shown in FIG. 8, and the top 10 ranking peptides matched to this spectrum are given below (SEQ ID NOS:265–274). Of these ten, the top ranking peptide, YGGFIRR is known to be Peptide Y.

| Rank/ Sp | (M + H) | Cn | C * 10⁴ | Sp | Ions | Reference | Peptide |
|---|---|---|---|---|---|---|---|
| 1/3 | 868.5 | 1.000 | 1.894 | 376.6 | 11/24 | p(415) | (–)YGGFIRR |
| 2/1 | 868.5 | 0.967 | 1.831 | 440.4 | 11/24 | p(298) | (–)YGGRIFR |
| 3/15 | 868.5 | 0.966 | 1.830 | 322.8 | 11/28 | p(1975) | (–)YGGFIGVR |
| 4/15 | 868.5 | 0.965 | 1.828 | 322.8 | 11/28 | p(1735) | (–)YGGFIVGR |
| 5/5 | 868.5 | 0.961 | 1.821 | 361.7 | 11/24 | p(454) | (–)YGGRFIR |
| 6/2 | 868.5 | 0.960 | 1.819 | 408.0 | 11/24 | p(1311) | (–)YGVNIFR |
| 7/12 | 868.5 | 0.951 | 1.802 | 333.7 | 11/24 | p(1527) | (–)YGVNFIR |
| 8/8 | 868.5 | 0.942 | 1.783 | 356.9 | 11/28 | p(2153) | (–)YGGGVIFR |
| 9/13 | 868.5 | 0.937 | 1.775 | 331.0 | 11/24 | p(394) | (–)YGGIFRR |
| 10/8 | 868.5 | 0.935 | 1.771 | 356.9 | 11/28 | p(2147) | (–)YGGVGIFR |

Example 3

The amino acid sequence of Peptide Z, a known standard peptide, was determined using the method of the invention, as applied to Peptide X in Example 1 and Peptide Y in Example 2. Peptide Z has the following amino acid sequence: RPPGFSPFR (SEQ ID NO:344). The molecular mass of Peptide Z was determined to be 1060.5660 to an experimental accuracy of 30 ppm from the mass spectrum shown in FIG. 9. The masses at 1181.6477, 1296.6933 and 1570.6774 are from internal standards, added to allow instrument calibration.

The set of amino acids that are possibly part of Peptide Z were then defined for consideration in the analysis. The defined set of amino acids with the molecular mass of each amino acid less the mass of the one water molecule lost during peptide bond formation are the same as those used in Examples 1 and 2.

Figure 9:
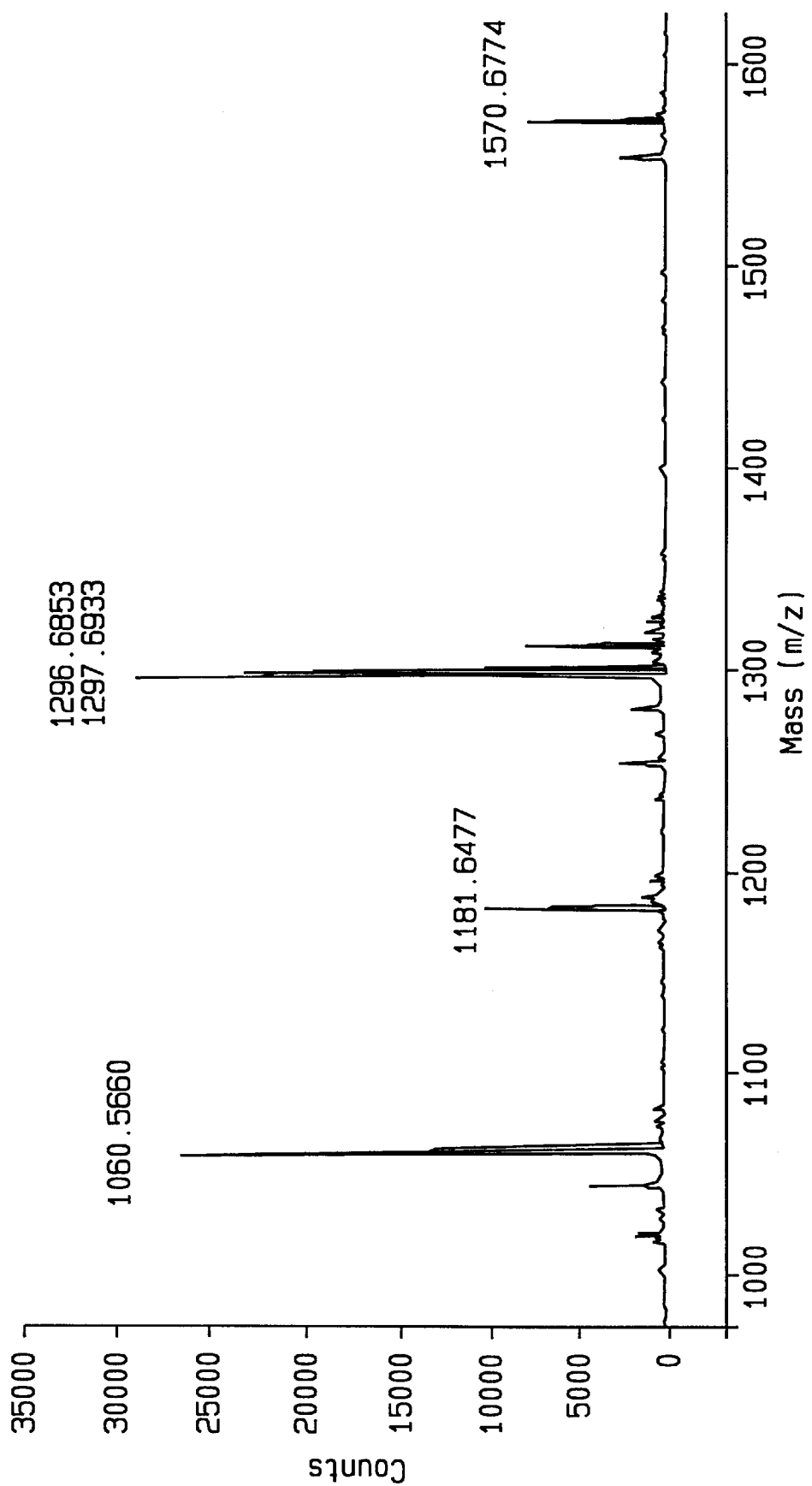
FIG. 9 is the experimental mass spectrum used to determine the molecular mass of Peptide Z.
Figure 10:
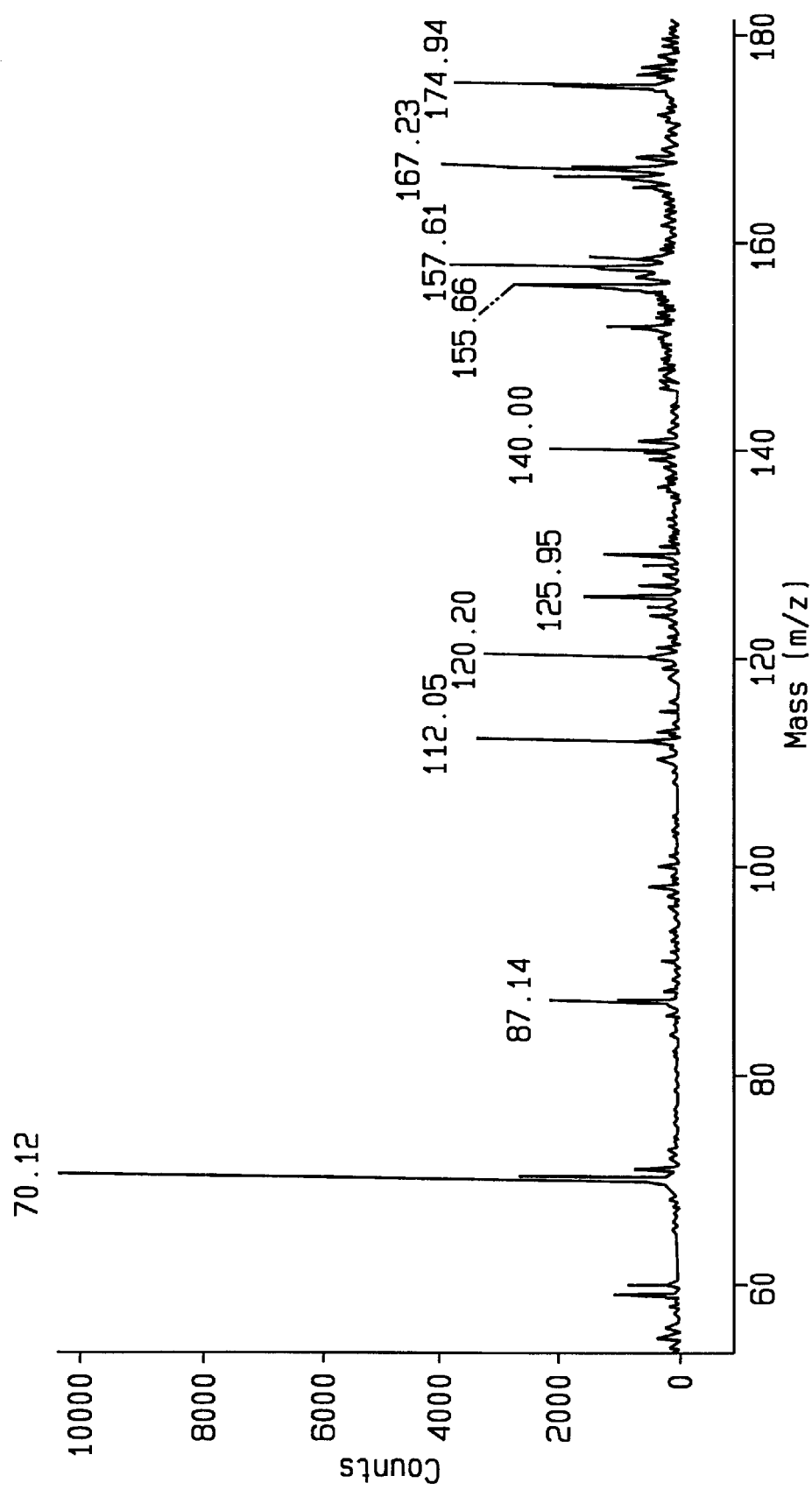
FIG. 10 is the immonium ion region of the mass spectrum shown in FIG. 9, and identifies amino acids contained in Peptide Z.

As the mass of Peptide Z was measured as 1060.5660 to an experimental accuracy of 30 ppm, each allowed amino acid combination must therefore sum to a mass equal to 1060.5660±30 ppm. In addition, from the immonium ion region of the PSD trace from FIG. 9, shown in FIG. 10, it was determined that Peptide Z must also contain the following amino acids: phenylalanine with a characteristic mass at 120.20, arginine with a characteristic mass at 174.94, serine together with proline as deduced from the mass at 167.23, and glycine together with proline as deduced from the mass at 155.66.

Application of the equation in Example 1 was used to determine the allowed combinations of amino acids for Peptide Z, and demonstrates that only the following combinations of amino acids are allowed for Peptide Y (SEQ ID NOS:275–343):

| | | | |
|---|---|---|---|
| PTIW+FRPSG | GAAAAR+FRPSG | GVVNK+FRPSG | AVVID+FRPSG |
| VVIW+FRPSG | GPPVF+FRPSG | ASPNK+FRPSG | SPVVD+FRPSG |
| GQRR+FRPSG | GPVIM+FRPSG | GGAAIK+FRPSG | GVINN+FRPSG |
| ANRR+FRPSG | APVVM+FRPSG | GGGPTK+FRPSG | AVVNN+FRPSG |
| GOARR+FRPSG | AAIIE+FRPSG | GGGVVK+FRPSG | GGGVIN+FRPSG |
| PPFR+FRPSG. | GPTIE+FRPSG | GAAAVK+FRPSG | GAAAIN+FRPSG |
| PIMR+FRPSG | GVVIE+FRPSG | GGASPK+FRPSG | GGAVVN+FRPSG |
| VIER+FRPSG | ASPIE+FRPSG | IQQQ+FRPSG | AAAAVN+FRPSG |
| VNQR+FRPSG | APVTE+FRPSG | GAIQQ+FRPSG | SSPII+FRPSG |
| CGVQR+FRPSG | AVVVE+FRPSG | AAVQQ+FRPSG | SPVTI+FRPSG |
| AAAQR+FRPSG | GSPKK+FRPSG | AAINQ+FRPSG | GGGGGVI+FRPSG |
| IIDR+FRPSG | IQQK+FRPSG | GVVNQ+FRPSG | GGGAAAAI+FRPSG |
| INM+FRPSG | GAIQK+FRPSG | GGAAIQ+FRPSG | PPTTT+FRPSG |
| GGINR+FRPSG | AAVQK+FRPSG | GGGVVQ+FRPSG | PVVTT+FRPSG |
| GAVNR+FRPSG | GSPQK+FRPSG | AAAVQ+FRPSG | GGGGAVV+FRPSG |
| GGGGIR+FRPSG | AAINY+FRPSG | GVIID+FRPSG | GGAAAAV+FRPSG |
| GGGAVR+FRPSG | GPTNK+FRPSG | APTID+FRPSG | AAAAAAA+FRPSG |

These combinations constitute the allowed set of amino acid combinations for Peptide Z.

In addition, Peptide Z was obtained by a tryptic cleavage, and, from the accepted specificity of trypsin, Peptide Z must have lysine or arginine as its carboxy terminal amino acid. With this constraint, the allowed library of linear peptides for Peptide Z is constructed from all individual linear permutations of the combinations above. The allowed library includes over 2,000,000 peptides, and is thus not shown.

Figure 11:
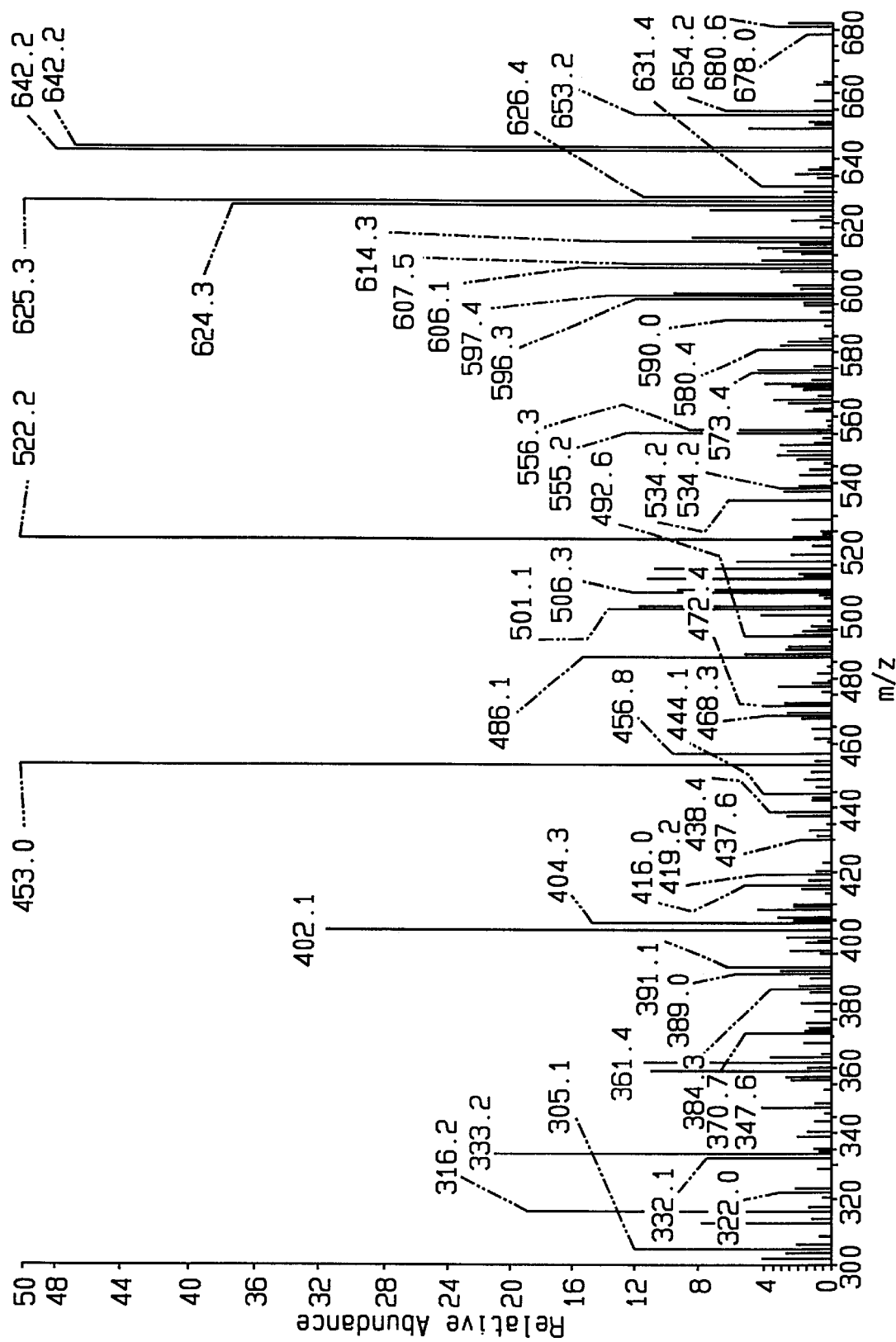
FIG. 11 is the experimental tandem mass spectrum of Peptide Z.

As with Examples 1 and 2, the method of U.S. Pat. No. 5,538,897 was then used to match Peptide Z to this library by tandem mass spectrometry. The experimental tandem mass spectrum of Peptide Z is shown in FIG. 11, and the top 10 ranking peptides matched to this spectrum provided below (SEQ ID NOS:344–353). Of these ten, the top ranking peptide, RPPGFSPFR (SEQ ID NO:344) is known to be Peptide Z.

| Rank/Sp | (M + H) | Cn | C * 10⁴ | Sp | Ions | Reference | Peptide |
|---|---|---|---|---|---|---|---|
| 1/1 | 1061.2 | 1.000 | 3.310 | 1163.5 | 19/24 | p(135) | (–)RPPGFSPFR |
| 2/2 | 1061.2 | 0.871 | 2.884 | 1126.6 | 19/24 | p(120) | (–)RPPGFPSFR |
| 3/5 | 1061.2 | 0.857 | 2.835 | 824.7 | 17/24 | p(122) | (–)RPPFGPSFR |
| 4/11 | 1061.2 | 0.849 | 2.811 | 692.8 | 16/24 | p(164) | (–)RPPGFFPSR |
| 5/4 | 1061.2 | 0.833 | 2.759 | 831.2 | 17/24 | p(189) | (–)RPPGFFSPR |
| 6/3 | 1061.2 | 0.831 | 2.749 | 872.9 | 17/24 | p(131) | (–)RPPSFGPFR |
| 7/6 | 1061.2 | 0.819 | 2.711 | 797.1 | 17/24 | p(126) | (–)RPFGPPSFR |
| 8/12 | 1061.2 | 0.806 | 2.668 | 674.0 | 16/24 | p(100) | (–)RPPGPSFFR |
| 9/13 | 1061.2 | 0.792 | 2.623 | 668.4 | 16/24 | p(137) | (–)RFPPGSPFR |
| 10/14 | 1061.2 | 0.782 | 2.588 | 656.5 | 16/24 | p(138) | (–)RFGPPSPFR |

While it is apparent that the invention disclosed herein is well calculated to fulfill the objectives stated above, it will be appreciated that numerous modifications and embodiments may be devised by those skilled in the art. Therefore, it is intended that the appended claims cover all such modifications and embodiments that fall within the true spirit and scope of the present invention.

We claim:

1. A method for determining the amino-acid sequence of a peptide of interest having a molecular mass, the method comprising:
   (a) designating a set of allowed amino acids;
   (b) determining the molecular mass of the peptide of interest;
   (c) collecting an experimental fragmentation mass spectrum for the peptide of interest using a mass spectrometer;
   (d) defining a set of allowed combinations comprising all combinations of allowed amino acids having a predicted total molecular mass consistent with the molecular mass of the peptide of interest;
   (e) defining a set of allowed peptides comprising all linear permutations of the allowed combinations;
   (f) calculating a theoretical fragmentation mass spectrum for allowed peptides in the set of allowed peptides, comprising calculating fragment-ion masses thereof and assigning an intensity value to one or more fragment ions of the theoretical fragmentation mass spectrum; and
   (g) comparing the experimental fragmentation mass spectrum of the peptide of interest to one or more theoretical fragmentation mass spectra calculated for the allowed peptides to determine the amino-acid sequence of the peptide of interest.

2. The method of claim 1, wherein the mass spectrometer is a time-of-flight mass spectrometer.

3. The method of claim 1, wherein the designated set of allowed amino acids comprises tryptophan, arginine, histidine, glutamic acid, glutamine, aspartic acid, leucine, threonine, proline, alanine, tyrosine, phenylalanine, methionine, lysine, asparagine, isoleucine, cysteine, valine, serine, and glycine.

4. The method of claim 1, wherein the molecular mass of the peptide of interest is determined with an accuracy of about 30 parts per million and the predicted total molecular mass of each allowed combination is within a range of plus or minus about 30 parts per million of the molecular mass of the peptide of interest.

5. The method of claim 1, wherein the peptide of interest has been treated to remove one or more post-translational modifications.

6. The method of claim 1, further comprising calculating an indication of closeness-of-fit between the experimental fragmentation mass spectrum of the peptide of interest and the theoretical fragmentation mass spectra.

7. The method of claim 6, wherein calculating the indication of closeness-of-fit comprises selecting peak values in the theoretical fragmentation mass spectra having an assigned intensity greater than a predetermined threshold value.

8. The method of claim 1, further comprising normalizing the experimental fragmentation mass spectrum.

9. The method of claim 1, wherein the designated set of allowed amino acids comprises carbamido cysteine.

10. The method of clam 1, wherein the peptide of interest has a molecular mass of greater than about 1,400 Daltons.

11. A method for determining the amino-acid sequence of a peptide of interest having a molecular mass, the method comprising:
    (a) designating a set of allowed amino acids;
    (b) determining the molecular mass of the peptide of interest;
    (c) collecting an experimental fragmentation mass spectrum for the peptide of interest using a mass spectrometer;
    (d) identifying one or more amino acids present in the peptide of interest;

(e) defining a set of allowed combinations comprising all combinations of allowed amino acids having a predicted total molecular mass consistent with the molecular mass of the peptide of interest, wherein every allowed combination includes the one or more identified amino acids;

(f) defining a set of allowed peptides comprising all linear permutations of the allowed combinations;

(g) calculating a theoretical fragmentation mass spectrum for allowed peptides in the set of allowed peptides, comprising calculating fragment-ion masses thereof and assigning an intensity value to one or more fragment ions of the theoretical fragmentation mass spectrum; and (h) comparing the experimental fragmentation mass spectrum of the peptide of interest to one or more theoretical fragmentation mass spectra calculated for the allowed peptides to determine the amino-acid sequence of the peptide of interest.

12. The method of claim 11, wherein the peptide of interest has a molecular mass of greater than about 1,400 Daltons.

13. The method of claim 11, further comprising analyzing an immonium region of the experimental fragmentation mass spectrum to identify one or more amino acids.

14. The method of claim 11, wherein a plurality of identified amino acids form a peptide fragment.

15. The method of claim 11, wherein the designated set of allowed amino acids comprises tryptophan, arginine, histidine, glutamic acid, glutamine, aspartic acid, leucine, threonine, proline, alanine, tyrosine, phenylalanine, methionine, lysine, asparagine, isoleucine, cysteine, valine, serine, and glycine.

16. The method of claim 11, wherein the designated set of allowed amino acids comprises carbamido cysteine.

17. The method of claim 11, wherein the peptide of interest has been treated to remove one or more post-translational modifications.

\* \* \* \* \*